(12) United States Patent
Beardsley et al.

(10) Patent No.: US 12,220,420 B2
(45) Date of Patent: ***Feb. 11, 2025

(54) COMBINATION THERAPY FOR CANCER TREATMENT

(71) Applicant: Galera Labs, LLC, Creve Coeur, MO (US)

(72) Inventors: Robert A. Beardsley, University City, MO (US); Dennis P. Riley, Chesterfield, MO (US); Jeffery L. Keene, St. Louis, MO (US); Douglas R. Spitz, Iowa City, IA (US); Melissa A. Fath, Iowa City, IA (US)

(73) Assignee: Galera Labs, LLC, Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/098,026

(22) PCT Filed: May 3, 2017

(86) PCT No.: PCT/US2017/030871
§ 371 (c)(1),
(2) Date: Oct. 31, 2018

(87) PCT Pub. No.: WO2017/192740
PCT Pub. Date: Nov. 9, 2017

(65) Prior Publication Data
US 2019/0151331 A1 May 23, 2019

Related U.S. Application Data

(60) Provisional application No. 62/331,253, filed on May 3, 2016.

(51) Int. Cl.
| | | |
|---|---|---|
| *A61K 31/555* | (2006.01) | |
| *A61K 31/198* | (2006.01) | |
| *A61K 31/4196* | (2006.01) | |
| *A61K 31/635* | (2006.01) | |
| *A61K 31/655* | (2006.01) | |
| *A61K 31/70* | (2006.01) | |
| *A61K 31/7135* | (2006.01) | |
| *A61K 33/242* | (2019.01) | |
| *A61K 33/243* | (2019.01) | |
| *A61K 45/06* | (2006.01) | |
| *A61N 5/10* | (2006.01) | |
| *A61P 35/00* | (2006.01) | |

(52) U.S. Cl.
CPC .......... *A61K 31/555* (2013.01); *A61K 31/198* (2013.01); *A61K 31/4196* (2013.01); *A61K 31/635* (2013.01); *A61K 31/655* (2013.01); *A61K 31/70* (2013.01); *A61K 31/7135* (2013.01); *A61K 33/242* (2019.01); *A61K 33/243* (2019.01); *A61K 45/06* (2013.01); *A61N 5/10* (2013.01); *A61P 35/00* (2018.01)

(58) Field of Classification Search
CPC ....... A61P 35/00; A61K 45/06; A61K 31/635; A61K 2300/00; A61K 31/70; A61K 31/555; A61K 33/24; A61K 33/32
See application file for complete search history.

(56) References Cited

U.S. PATENT DOCUMENTS

| | | |
|---|---|---|
| 3,930,867 A | 1/1976 | Bigelow |
| 4,001,212 A | 1/1977 | Richman |
| 4,702,998 A | 10/1987 | Tanaka et al. |
| 5,096,724 A | 3/1992 | Zenner et al. |
| 5,610,293 A | 3/1997 | Riley et al. |
| 5,624,677 A | 4/1997 | El-Rashidy et al. |
| 5,637,578 A | 6/1997 | Riley et al. |
| 5,874,421 A | 2/1999 | Riley et al. |

(Continued)

FOREIGN PATENT DOCUMENTS

| | | |
|---|---|---|
| CN | 1215919 | 5/1999 |
| CN | 2870352 | 2/2007 |

(Continued)

OTHER PUBLICATIONS

Du et al., Journal of Biological Chemistry, vol. 287, No. 45, pp. 38210-38219, Nov. 2, 2012.*

(Continued)

*Primary Examiner* — Alicia L Otton
(74) *Attorney, Agent, or Firm* — Bryan Cave Leighton Paisner LLP

(57) ABSTRACT

A method of treating cancer in a subject includes administering at least one active agent including one or more of a thioredoxin reductase inhibitor and a glutathione depleting agent, and administering a pentaaza macrocyclic ring complex corresponding to formula (I) below:

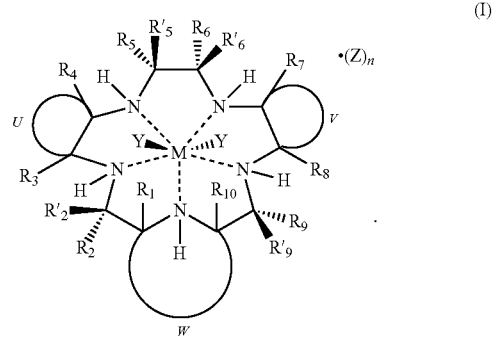

(I)

21 Claims, 22 Drawing Sheets

(56) References Cited

U.S. PATENT DOCUMENTS

| | | |
|---|---|---|
| 5,976,498 A | 11/1999 | Newumann et al. |
| 6,040,330 A | 3/2000 | Hausheer et al. |
| 6,084,093 A | 7/2000 | Riley et al. |
| 6,177,419 B1 | 1/2001 | Campbell et al. |
| 6,180,620 B1 | 1/2001 | Salvemini |
| 6,204,259 B1 | 3/2001 | Riley et al. |
| 6,214,817 B1 | 4/2001 | Riley et al. |
| 6,245,758 B1 | 6/2001 | Stern et al. |
| 6,395,725 B1 | 5/2002 | Salvemini |
| 6,525,041 B1 | 2/2003 | Neumann et al. |
| 6,552,010 B1 | 4/2003 | Bernstein |
| 6,552,040 B1 | 4/2003 | Bernstein |
| 6,781,231 B2 | 8/2004 | Minervini |
| 6,916,799 B2 | 7/2005 | Fridovich et al. |
| 7,102,214 B1 | 9/2006 | Miks et al. |
| 7,166,910 B2 | 1/2007 | Minervini |
| 7,242,089 B2 | 7/2007 | Minervini |
| 7,407,645 B2 | 8/2008 | Neumann et al. |
| 7,445,641 B1 | 11/2008 | Omberg et al. |
| 7,981,421 B2 | 7/2011 | Zhou et al. |
| 8,263,568 B2 | 9/2012 | Slomczynska et al. |
| 8,444,856 B2 | 5/2013 | Slomczynska et al. |
| 8,486,928 B2 | 7/2013 | Riley |
| 8,808,545 B2 | 8/2014 | Slomczynska et al. |
| 9,150,837 B2 | 10/2015 | Salvemini et al. |
| 9,198,893 B2 | 12/2015 | Keene et al. |
| 9,353,069 B2 | 5/2016 | Riley |
| 9,642,861 B2 | 5/2017 | Rothstein et al. |
| 9,738,669 B2 | 8/2017 | Keene et al. |
| 9,738,670 B2 | 8/2017 | Keene et al. |
| 9,855,279 B2 | 1/2018 | Rothstein et al. |
| 10,137,133 B2 | 11/2018 | Keene et al. |
| 10,350,193 B2 | 7/2019 | Riley |
| 10,493,081 B2 | 12/2019 | Keene et al. |
| 10,597,415 B2 | 3/2020 | Keene et al. |
| 10,610,533 B2 | 4/2020 | Rothstein et al. |
| 11,066,433 B2 | 4/2021 | Keene et al. |
| 11,219,614 B2 | 1/2022 | Beardsley et al. |
| 11,246,950 B2 | 2/2022 | Beardsley et al. |
| 11,612,608 B2 | 3/2023 | Rothstein et al. |
| 11,826,373 B2 | 11/2023 | Keene et al. |
| 2002/0072512 A1 | 6/2002 | Salvemini |
| 2002/0128248 A1 | 9/2002 | Salvemini |
| 2003/0050297 A1 | 3/2003 | Crapo |
| 2004/0219138 A1 | 11/2004 | Salvemini |
| 2005/0101581 A1 | 5/2005 | Reading et al. |
| 2005/0171198 A1 | 8/2005 | Salvemini |
| 2005/0175580 A1 | 8/2005 | Salvemini |
| 2005/0222250 A1 | 10/2005 | Rezvani |
| 2006/0081994 A1 | 4/2006 | Craig et al. |
| 2006/0089710 A1 | 4/2006 | Ornberg et al. |
| 2006/0140953 A1 | 6/2006 | Newell et al. |
| 2006/0199792 A1 | 9/2006 | Groves et al. |
| 2006/0223808 A1 | 10/2006 | Chackalamannil et al. |
| 2007/0148154 A1 | 6/2007 | Weill et al. |
| 2008/0161324 A1 | 7/2008 | Johansen et al. |
| 2008/0166000 A1 | 7/2008 | Hsiao |
| 2008/0269185 A1 | 10/2008 | Rothstein et al. |
| 2009/0131377 A1 | 5/2009 | Salvemini |
| 2009/0221622 A1 | 9/2009 | Teja et al. |
| 2009/0257979 A1 | 10/2009 | Beigelman et al. |
| 2010/0304415 A1 | 12/2010 | Slomczynska et al. |
| 2011/0136756 A1 | 6/2011 | Keene et al. |
| 2013/0079317 A1 | 3/2013 | Keene et al. |
| 2014/0142065 A1 | 5/2014 | Che et al. |
| 2018/0237462 A1 | 8/2018 | Keene et al. |
| 2019/0151331 A1 | 5/2019 | Beardsley et al. |
| 2019/0209524 A1 | 7/2019 | Beardsley et al. |
| 2019/0350867 A1 | 11/2019 | Hahn |
| 2020/0000793 A1 | 1/2020 | Falo, Jr. et al. |
| 2020/0215077 A1 | 7/2020 | Rothstein et al. |
| 2020/0376148 A1 | 12/2020 | Beardsley et al. |
| 2021/0338686 A1 | 11/2021 | Keene et al. |
| 2021/0347796 A1 | 11/2021 | Keene et al. |
| 2021/0361701 A1 | 11/2021 | Keene et al. |
| 2022/0088030 A1 | 3/2022 | Keene et al. |
| 2022/0118119 A1 | 4/2022 | Beardsley et al. |

FOREIGN PATENT DOCUMENTS

| | | |
|---|---|---|
| CN | 108350009 A | 7/2018 |
| EA | 010834 | 12/2008 |
| JP | 1996040941 | 2/1996 |
| JP | 2002506445 | 2/2002 |
| JP | 2002534382 | 10/2002 |
| JP | 2003509423 | 3/2003 |
| JP | 2004507487 | 3/2004 |
| JP | 2004517113 | 6/2004 |
| JP | 2011513333 | 4/2011 |
| JP | 2014526562 | 10/2014 |
| JP | 2018500347 | 1/2018 |
| JP | 2018193302 | 12/2018 |
| RU | 2313368 | 9/2011 |
| WO | 199110645 | 7/1991 |
| WO | 1993002090 | 2/1993 |
| WO | 1994015925 | 7/1994 |
| WO | 95028968 | 11/1995 |
| WO | 1996039396 | 12/1996 |
| WO | 97006830 | 2/1997 |
| WO | 98058636 | 12/1998 |
| WO | 00072893 | 12/2000 |
| WO | 01019823 | 3/2001 |
| WO | 200158458 | 8/2001 |
| WO | 02053142 | 7/2002 |
| WO | 2002071054 | 9/2002 |
| WO | 2002100395 | 12/2002 |
| WO | 2003024434 | 3/2003 |
| WO | 2005042718 | 5/2005 |
| WO | 2005060976 | 7/2005 |
| WO | 2006083508 | 8/2006 |
| WO | 2009111294 | 9/2009 |
| WO | 2009134616 | 11/2009 |
| WO | 2009143454 | 11/2009 |
| WO | 2011516610 | 5/2011 |
| WO | 2011113019 | 9/2011 |
| WO | 2016102543 | 6/2016 |
| WO | 2017025496 A1 | 2/2017 |
| WO | 2019152661 A1 | 8/2019 |
| WO | 2024026273 | 2/2024 |

OTHER PUBLICATIONS

Elting et al., The Burdens of Cancer Therapy, Cancer, 98(7): 1531-1539 2003.

Epperly et al., Manganese Superoxide Dismutase-Plasmid/ Liposome (MnSOD-PL) Administration Protects Mice from Esophagitis Associated with Fractionated Radiation, Int. J. Cancer (Radiat. Oncol. Invest), 96: 221-231 2001.

Epperly et al., Intraoral Manganese Superoxide Dismutase-Plasmid/ Liposome (MnSOD-PL) Radioprotective Gene Therapy Decreases Ionizing Irradiation-induced Murine Mucosal Cell Cycling and Apoptosis, In Vivo, 18:401-410 2004.

Guo et al., Gene Transfer of Human Manganese Superoxide Dismutase Protects Small Intestinal Villi From Radiation Injury, J Gastrointest Surg., 7(2): 229-235 2003.

Lalla et al., Treatment of Mucositis, Including New Medications, Palliative and Supportive Care, 12(5): 348-354 2006.

Murakami, The Chemical Society of Japan, editions, Separation of Optical Isomer quarterly journal, chemical review No. 6, Scientific Societies Press, p. 212-213 (translation) 1989.

Anderson, et al. Two-Year Tumor Outcomes of Phase 2B, Randomized, Double-Blind Trial of Avasopasem Manganese (GC4419) Versus Placebo to Reduce Severe Oral Mucositis Due to Concurrent Radiation Therapy and Cisplatin for Head and Neck Cancer Published:Jun. 17, 2022DOI:https://doi.org/10.1016/j.ijrobp.2022. 06.063.

Anderson, et al. Phase IIb, Randomized, Double-Blind Trial of GC4419 Versus Placebo to Reduce Severe Oral Mucositis Due to Concurrent Radiotherapy and Cisplatin For Head and Neck Cancer, Journal of Clinical Oncology 37, No. 34 (Dec. 1, 2019) 3256-3265.

(56) References Cited

OTHER PUBLICATIONS

Anderson et al., Phase 1b/2a Trial of Superoxide (SO) Dismutase (SOD) Mimetic GC4419 to Reduce Chemoradiation Therapy-Induced Oral Mucositis (OM) in Patients With Oral Cavity or Oropharyngeal Carcinoma (OCC), Intl. J. Rad. Oncol., vol. 100, Issue 2, p. 427-435, Feb. 1, 2018.
ASCO Abstract Effects of GC4419 (avasopasem manganese) on chronic kidney disease in head and neck cancer patients treated with radiation and cisplatin, American Society of Clinical Oncology, 2020 2 pages.
Mapuskar, et al. Mitochondrial Superoxide Dismutase in Cisplatin-Induced Kidney Injury, Antioxidants 2021, 10, 1329 16 pages.
O'Leary, et al. Loss of SOD3 (EcSOD) Expression Promotes an Aggressive Phenotype in Human Pancreatic Ductal Adenocarcinoma, Downloaded from www.clincancerres.aacrjournals.org on Jul. 17, 2020 pp. 1741-1751.
Sishc, et al. Avasopasem manganese synergizes with hypofractionated radiation to ablate tumors through the generation of hydrogen peroxide, Sci. Transl. Med. 13, May 12, 2021 pp. 1-13.
Sishc, et al. Avasopasem Manganese Protects Against Radiation Induced Oral Mucositis and Enhances the Response of Squomous Cell Carcinoma of the Head and Neck to Ionizing Radiation and Radioimmune Therapy, Astro, vol. 108, Issue 3, Suppl. S159, Nov. 1, 2020.
Sishc, et al. Abstract: The radioprotector GC4419 enhances the response of pancreatic ductal adenocarcinoma tumors to high dose per fraction radiation exposure, AACR PDAC Meeting 2019.
Steinbach, et al. Effects of GC4419 (Avasopasem Manganese) on Chronic Kidney Disease in Head and Neck Cancer Patients Treated with Radiation and Cisplatin, ASCO20 May 2020 1 pages.
Zhang et al. Thioredoxin reductase inhibitors: a patent review, Expert Opinion on Therapeutic Patents, 27(5): 547-556 2017.
Ansel, et al. Pharmaceutical Dosage Forms and Drug Delivery Systems, Published by Lippincott Williams & Wilkins p. 48-53.
Declaration under 37 C.F.R. 1.132 of Dennis P. Riley, dated Mar. 7, 2014, and filed in U.S. Appl. No. 11/871,848.
Declaration under 37 C.F.R. 1.132 of Douglas R. Spitz, dated Feb. 6, 2014, and filed in U.S. Appl. No. 11/871,848.
Du, et al. Glutathione and glutaredoxin act as backup of human thioredoxin reductatse thioredoxin 1 preventing cell death by aurothioglucose, J Biol Chem 287(45), 38210-38219 2012.
Gemzar product Sheet 1996.
Meng, et al. "Potentiation of Endogenous Nitric Oxide With Superoxide Dismutase Inhibits Platelet-Mediated Thrombosis in Injured and Stenotic Arteries," JACC vol. 25, No. 1 Jan. 1995:269-75.
Black, et al. "Inhibition of in vivo myocardial ischemic and reperfusion injury by a synthetic manganese-based superoxide dismutase mimetic," Journal of Pharmacology and Experimental Therapeutics, Sep. 1994, 270 (3) 1208-1215.
Dennis, et al. "NADPH oxidases and reactive oxygen species at different stages of chronic hypoxia-induced pulmonary hypertension in newborn piglets," Am J Physiol Lung Cell Mol Physiol 297: L596-L607, 2009.
Cuzzocrea, et al. "Superoxide: a key player in hypertension," FASEB Journal vol. Jan. 18, 2004 pp. 94-101.
Wang, et al. "Blockade of Phencyclidine-Induced Cortical Apoptosis and Deficits in Prepulse Inhibition by M40403, a Superoxide Dismutase Mimetic," JPET, vol. 304, No. 1 pp. 266-272.
Sosman & Mier, "Biological drug duo delivers one-two tumor punch," Nature Medicine, vol. 9, No. 6, Jun. 2003 pp. 649-650.
Adringa, et al. "SOD mimics as adjuvants to chemotherapy protocols involving Adriamycin," Oxygen Society Meeting, San Antonio, TX Nov. 2002.
Mapuskar, et al. "Mitochondrial Superoxide Dismutase in Cisplatin-Induced Kidney Injury," Antioxidants, vol. 10, No. 9, Aug. 24, 2021 p. 1329.
Galera Therapeutics, Inc., A Phase 1 Dose Escalation Study of GC4419 in Combination With Chemoradiation for Squamous Cell Cancer of the Head & Neck, NIH U.S. National Library of Medicine, ClinicalTrials.gov,, 8 pages 2013.
Dyck et al., Immune checkpoints and their inhibition in cancer and infectious diseases, European Journal of Immunology, 47: 765-779 2017.
Fan et al., Enhancement of auranofin-induced lung cancer cell apoptosis by selenocystine, a natural inhibitor of TrxR1 in vitro and in vivo, Cell Death & Disease, 5, e1191 2018.
Kurosawa et al., Cytotoxicity induced by inhibition of thioredoxin reductases via multiple signaling pathways: Role of cytosolic phospholipase A2alpha-dependent and -independent release of arachidonic acid, Journal of Cell Physiology, 219(3): 606-616 2009.
Li et al., Auranofin-mediated inhibition of PI3K/AKT/mTOR axis and anticancer activity in non-small cell lung cancer cells. Oncotarget, 7(3): 3548-3558 2016.
European Patent Office, Extended European Search Report for 19747505.6 publication 3746085 21 pgs. Feb. 9, 2022.
Anderson et al., Phase 1b Trial of Superoxide Dismutase Mimetic GC4419 to Reduce Chemoradiotherapy-induced Oral Mucositis in Patients with Oral Cavity or Oropharyngeal Carcinoma, Multidisciplinary Head and Neck Cancer Symposium, Scottsdale, Arizona, 17 pgs, Feb. 18, 2016.
Kelso et al., A Mitochondria-Targeted Macrocyclic Mn(II) Superoxide Dismutase Mimetic, Chemistry & Biology, 19:1237-1246, 2012.
Laurent et al. Controlling Tumor Growth by Modulating Endogenous Production of Reactive Oxygen Species, Cancer Research, 65(3): 948-956, 2005.
Tovmasyan et al., Anticancer therapeutic potential of Mn porphyrin/ascorbate system, Free Radical Biology and Medicine, 89:1231-1247, 2015.
Rawal et al., Manganoporphyrins Increase Ascorbate-Induced Cytotoxicity by Enhancing H2O2 Generation, Cancer Research, 73(16):5232-5241, 2013.
Batinic-Haberle et al., An educational overview of the chemistry, biochemistry and therapeutic aspects of Mn porphyrins—From superoxide dismutation to H2O2-driven pathways, Redox Biology, 5:43-65, 2015.
Marzano et al., Inhibition of thioredoxin reductase by auranofin induces apoptosis in cisplatin-resistant human ovarian cancer cells, Free Radical Biology & Medicine 42: 872-881, 2007.
U.S. Department of Health and Human Services, Food and Drug Administration, Center for Drug Evaluation and Research (CDER), Guidance for Industry Estimating the Maximum Safe Starting Dose in Initial Clinical Trials for Therapeutics in Adult Healthy Volunteers, 30 pages, 2005.
Qian et al., Advances in the study of effects of vitamin C on tumor prevention, Youjiang Medical Journal, 36(6): 741-743, 2008.
Ghosh et al., A novel manganese complex, Mn-(II) N-(2-hydroxy acetophenone) glycinate overcomes multidrug-resistance in cancer, European Journal of Pharmaceutical Sciences, 49: 737-747, 2013.
Serafim et al., Regulating mitochondrial respiration in cancer in: Kanner S. (eds) Tumor Metabolome Targeting and Drug Development, Cancer Drug Discovery and Development, 45 pages, 2014.
Liu et al., Mechanisms of the CDK4/6 inhibitor palbociclib (PD 0332991) and its future application in cancer treatment (Review), Oncology Reports, 36: 901-911, 2018.
Friend, D. R., Review article: Issues in oral administration of locally acting glucocorticosteroids for treatment of Inflammatory bowl disease, Aliment Pharmacol Therapy, 12: 591-603, 1998.
Shadad et al., Gastrointestinal radiation injury: Symptoms, risk factors and mechanisms, World Journal of Gastroenterology, 19(2): 185-198, 2013.
Yu et al., Intestinal stem cell injury and protection during cancer therapy, Transl Cancer Research, 2(5): 384-396, 2013.
Kim et al., Antiproliferative effect of gold(I) compound auranofin through inhibition of STAT3 and telomerase activity in MDA-MB 231 human breast cancer cells, BMB Rep., 46(1): 59-64, 2013.
Zou et al., Auranofin induces apoptosis by ROS-mediated ER stress and mitochondrial dysfunction and displayed synergistic lethality with piperlongumine in gastric cancer, Oncotarget, 6(34): 36505-36521, 2015.
European Patent Office, Extended European Search Report issued for 18785213.2, 16 pages, Feb. 8, 2021.
Mikirova, et al. CAS: 158, 290966, 2012.

(56) References Cited

OTHER PUBLICATIONS

Alexandre, et al. "Improvement of the therapeutic index of anticancer drugs by the superoxide dismutase mimic mangafodipir," Journal of the National Cancer Institute, vol. 98, No. 4, Feb. 15, 2006, pp. 236-244, Feb. 15, 2006.
Belotte, et al. "Abstract B01: Superoxide dismutase significantly reversed the development of cisplatin resistance in epithelial ovarian cancer," Acquired Resistance, Feb. 13, 2015 pp. B01-B01, Feb. 13, 2015.
Karlsson, et al. "Calmangafodipir [Ca4Mn (DPDP) 5], mangafodipir (MnDPDP) and MnPLED with special reference to their SOD mimetic and therapeutic properties," Drug Discovery Today, vol. 20, No. 4, Apr. 1, 2015.
Ahmed, et al. "Tempol, a Superoxide Dismutase Mimetic Agent, Ameliorates Cisplatin-Induced Nephrotoxicity through Alleviation of Mitochondrial Dysfunction in Mice," PLOS ONE, vol. 9, No. 10, Jan. 1, 2014.
Wangila, et al. "Prevention of cisplatin-induced kidney epithelial cell apoptosis with a Cu superoxide dismutase-mimetic [copper 2/\I/\I (3,5-ditertiarybutylsalicylate) 4(ethanol)"4], Toxicology In Vitro, Elsevier Science, vol. 20, No. 8 Dec. 1, 2006 pp. 1300-1312.
Kobayashi, et al. "Enhancement of Anti-Cancer Activity of Cisdiaminedichloroplatinum by the Protein-Bound Polysaccharide of Coriolus Versicolor Quel (PS-K) In Vitro," Cancer Biotherapy, vol. 9, No. 4 Jan. 1, 1994 pp. 351-358.
Karlsson, et al. "First clinical expeirence with the magnetic resonance imaging contrast agent and superoxide dismutase mimetic mangafodipir as an adjunct in cancer chemotherapy-a translational study," Translational Oncology, Feb. 1, 2012 pp. 32-38.
Karlsson, et al. "Superior therapeutic index of calmangafodipir in comparison to mangafodipir as a chemotherapy adjunct," Translational Oncology, Dec. 1, 2012 p. 492.
Davis, et al. "Manganese Superoxide Dismutase Attenuates Cisplatin-Induced Renal Injury: Importance of Suproxide," Journal of the American Society of Nephrology, vol. 12, No. 12, Dec. 1, 2001 pp. 2683-2690.
Mohanty, et al. "Abstract 2929: GC4419 enhances the response of non-small cell lung carcinoma cell lines to cisplatin and cisplatin plus radiation through a ROS-mediated pathway : Cancer Research," AACR Annual Meeting 2018, Jul. 1, 2018 pp. 1-4.
European Patent Office, Extended European Search Report for 20168046.96 16 pages, Oct. 16, 2020.
Zhang et al. Thioredoxin reductase inhibitors: a patent review, Expert Opinion on Therapeutic Patents, 27(5): 547-556, Published Online Dec. 26, 2016.
Wagner, B. A., et al., Myeloperoxidase is involved in H2O2-induced apoptosis of HL-60 human leukemia cells, J. Biol. Chem, 2000, 272(29), 22461-9.
Chen, Q., et al., Pharmacologic ascorbic acid concentrations selectively kill cancer cells: action as a pro-drug to deliver hydrogen peroxide to tissues, PNAS, 2005, 102(38), 13604-9.
Rodriguez, et al., Mitochondrial or cytosolic catalase reverses the MnSOD-dependent inhibition of proliferation by enhancing respiratory chain activity, net ATP production, and decreasing the steady state levels of H2O2, Free Rad. Bio. & Med, (Dec. 2000).
Alexandre, J., et al., Novel Action of Paclitaxel against Cancer Cells: Bystander Effect Mediated by Reactive Oxygen Species, Cancer Research, 2007, 67(8), 3512-3517.
Muscoli, C., et al., On the selectivity of superoxide dismutase mimetics and its importance in pharmacological studies, British Journal of Pharmacology, 2003, 140(3), 445-460.
Sawyer, D. T. et al., How super is superoxide?, Acc. Chem. Res., 1981, 14, 393-400.
Li, S., et al., The Role of Cellular Glutathione Peroxidase Redox Regulation in the Suppression of Tumor Cell Growth by Manganese Superoxide Dismutase, Cancer Res., 2000, 60(14), 3927-3939.
Buettner, G. R., et al., A New Paradigm: Manganese Superoxide Dismutase Influences the Production of H2O2 in Cells and Thereby Their Biological State, Free Radical Biology and Medicine, 2006, 41(8), 1338-50.
Day, B. J., Catalase and glutathione peroxidase mimics, Biochem Pharmacol, 2009, 77(3), 285-296.
Day, B. J. et al., Manganic Porphyrins Possess Catalase Activity and Protect Endothelial Cells against Hydrogen Peroxide-Mediated Injury, Arch. Biochem. & Biophysics, 1997, 347(2), 256-262.
Oberley, L. W., Mechanism of the tumor suppressive effect of MnSOD overexpression, Biomedicine & Pharmacotherapy, 2005, 59, 143-48 Mar. 19, 2005.
Rocklage et al., Manganese(II) N , N'-Dipyridoxylethylenediamine-N , N'-diacetate 5,5'- Bis(phosphate). Synthesis and Characterization of a Paramagnetic Chelate for Magnetic Resonance Imaging Enhancement, Inorg. Chem., 1989, 28, 477-485, Sep. 29, 1988.
European Patent Office, Extended Search Report issued for 12835035.2, dated Mar. 9, 2015.
Masini et al., Prevention of antigen-induced early obstruction reaction by inhaled M40419 in actively sensitized guinea-pigs, American Journal of Respiratory and Critical Case Medicine, American Lung Associations, New York, NY, Jan. 1, 2002.
McCarthy, A., Metaphore Pharmaceuticals, Chemistry & Biology, 2003, 10(12): 1139-1140.
Macarthur et al., Modulation of serum cytokine levels by a novel superoxide dismutase mimetic, M40401, in an *Escherichia coli* model of septic shock: Correlation with preserved circulating catecholamines, Crit. Care Med., 2003, 31(1): 237245.
Aston et al., Computer-Aided Design (CAD) of Mn(II) Complexes: Superoxide Dismutase Mimetics with Catalytic Activity Exceeding the Native Enzyme, Inorg. Chem., 2001, 40: 1779-1789.
Salvemini et al., Nonpeptidyl mimetics of superoxide dismutase in clinical therapies for diseases, Cell and Mol Life Sci, 2000, 57: 1489-1492.
Macarthur et al., Inactivation of catecholamines by superoxide gives new insights on the pathogenesis of septic shock, PNAS, 2000, 97(17): 9753-9758.
Riley, P.A., Free radicals in biology: oxidative stress and the effects of ionizing radiation, Int. J. Radiat. Biol, 1994, 65(1): 27-33.
Shimizu et al., Neuroprotection against hypoxia-ischemia in neonatal rat brain by novel superoxide dismutase mimetics, Neuroscience Letters, 2003, 346: 41-44.
Tuder et al., Oxidative Stress and Apoptosis Interact and Cause Emphysema Due to Vascular Endothelial Growth Factor Receptor Blockade, Am. J. Respir. Cell Mol. Biol., 2003, 29: 88-97.
Fike et al., Reactive oxygen species from NADPH oxidase contribute to altered pulmonary vascular responses in piglets with chronic hypoxia-induced pulmonary hypertension, 2008, 295(5): L881-L888.
Batinic-Haberle et al., The ortho effect makes manganese(III) meso-tetrakis(N-methylpyridinium-2-yl)porphyrin a powerful and potentially useful superoxide dismutase mimic, J Biol Chem, 1998, 273: 24521-24528.
Batinic-Haberle et al., Pure MnTBAP selectively scavenges peroxynitrite over superoxide: , Free Radic Biol Med, 2009, 46:192-201.
Day et al., Metalloporphyrins are potent inhibitors of lipid peroxidation, Free Radic Biol Med, 1999, 26: 730-736.
Day et al., A metalloporphyrin superoxide dismutase mimetic protects against paraquat-induced endothelial cell injury, In vitro, J Pharmacol Exp Ther, 1995, 275: 1227-1232.
Ferrer-Sueta et al., Reactions of Manganese Porphyrins with Peroxynitrite and Carbonate Radical Anion, J Biol Chem, 2003, 278: 27432-27438.
Kachadourian et al., Flavin-dependent antioxidant properties of a new series of meso-N,N'-dialkyl-imidazolium substituted manganese(III) porphyrins, Biochem Pharmacol, 2004, 67:77-85.
Szabo et al., Evaluation of the relative contribution of nitric oxide and peroxynitrite to the suppression of mitochondrial respiration in immunostimulated macrophages using a manganese, FEBS Letters, 1996, 381:82-86.
Salvemini et al., A nonpeptidyl mimic of superoxide dismutase with therapeutic activity in rats, Science, 1999, 286: 304-306.
Thompson et al., The manganese superoxide dismutase mimetic, M40403, protects adult mice from lethal total body Irradiation, Free Radical Research, 2010; 44(5): 529-540.
Patent Cooperation Treaty, International Search Report issued for PCT/US2012/056921 on Feb. 22, 2013, 5 pages.

(56) References Cited

OTHER PUBLICATIONS

Simic et al., Oxygen radicals in biology and medicine, Basic Life Sciences, 1988, vol. 49, Plenum Press, New York and London.
Weiss et al., Catalytic Efficacies of agents that dismutate superoxide, 1991, J. Cell, Biochem, Suppl. 15C, 216 Abstract C110.
Petkau, Scientific basis for the clinical use of superoxide dismutase, 1986, Cancer Treat. Rev. 13, 17.
McCord, Superoxide dismutase: Rationale for use in ruperfusion injury and inflammation, 1986, J. Free Radicals Biol. Med, 2, 307.
Bannister et al., Aspects of the structure, function, and applications of superoxide dismutase, 1987, Crit. Rev. Biochem., 22, 111.
Gryglewski et al., Superoxide anion is involved in the breakdown of endothelium-derived vascular relaxing factor, 1986, Nature, 320, 454-456.
Palmer et al., Nitric oxide release accounts for the biological activity of endothelium derived relaxing factor, 1987, Nature, 327, 523-526.
Samlowski et al., A nonpeptidyl mimic of superoxide dismutase, M40403, inhibits does-limiting hyptension associated with interleukin-2 and increases its antitumor effects, 2003, Nature Medicine, 9, 750-755.
Riley et al., Structure-activity studies and the design of synthetic superoxide dismutase (SOD) mimetics as therapeutics, 2006, Advances in Inorganic Chemistry, 59, 233-263.
Riley et al., Synthesis, characterization, and stability of manganese(II) C-Substituted 1, 4, 7, 10, 12-Pentaazacyclopentadecane complexes exhibity superoxide dismutase activity, J. Inorg. Chem. 1996, 35: 5213-5231.
Salvemini et al., M40403: Superoxied dismutase mimic, Drugs of the Future, 2000, 25(10): 1027-1033.
Salvemini et al., SOD Mimetics are coming of age, Nature Reviews, 2002, 1: 367-374.
Aykin-Burns et al., Increased levels of superoxide and H2O2 mediate the differential susceptibility of cancer cells versus normal cells to glucose deprivation, Biochem. J., 2009, 418: 29-37 2009.
Fretland et al., Superoxide Dismutase (SOD) Modulates Acetic Acid-Induced Colitis in Rodents, Gastroenterology, 1991, 100: A581 1991.
Newton et al., Synthesis and characterization of the Mn(II) complex of [15]aneN.sub.5, J. Coord. Chem., 1988, 19: 265-277 1988.
Bradshaw et al., A simple crab-like cyclization procedure to prepare polyaza-crowns and cyclams with one or two unsubstitute macroring Nitrogen atoms or with a Hydroxy group, J. Heterocyclic Chem, 1989, 26: 1431-1435 1989.
Karkowiak et al., Preparation of Triaza-, Tetraaza- and Peraza-Crown Compounds containing Aminoalkyl Side Groups or Unsubstituted Rin Nitrogen Atoms, J. Org. Chem, 1990, 55(10): 3364-3368 1990.

\* cited by examiner

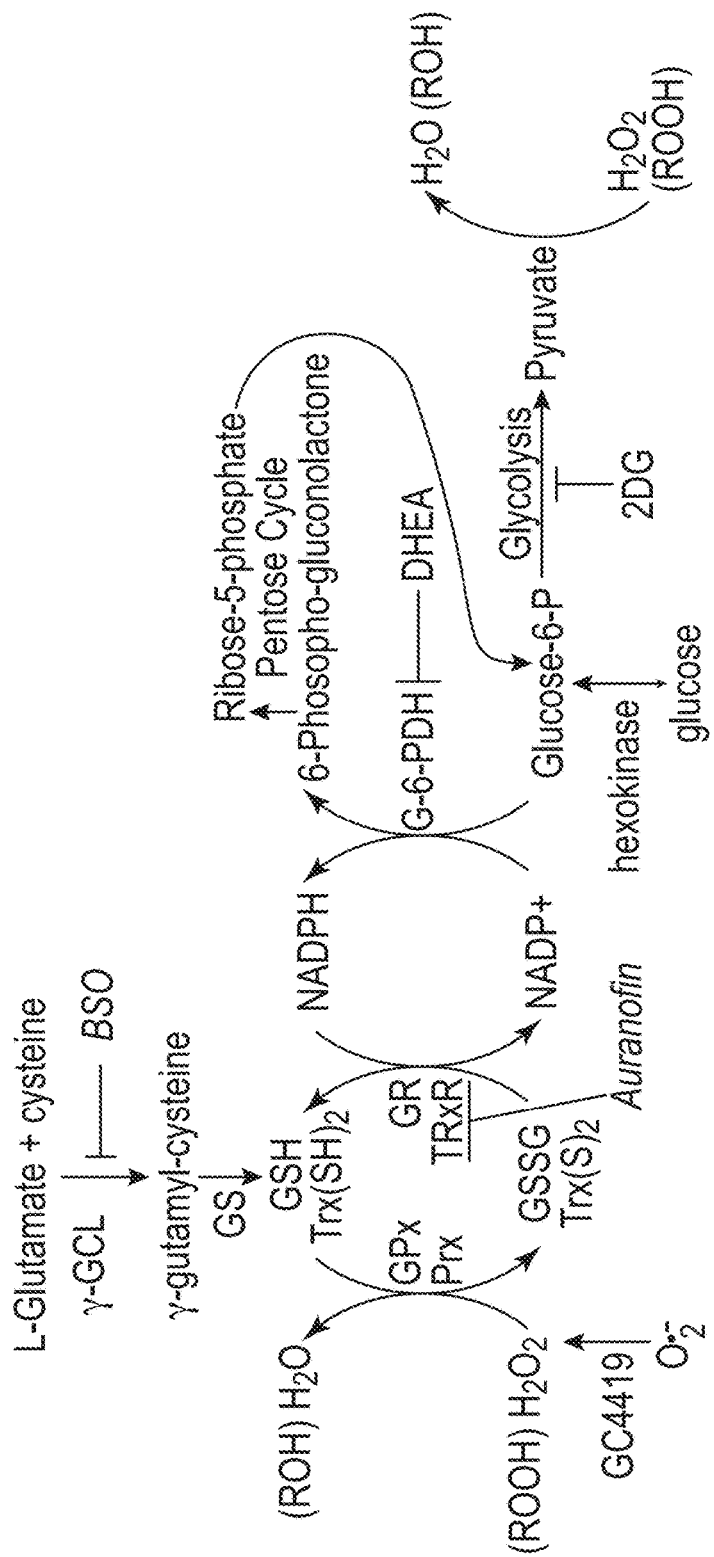
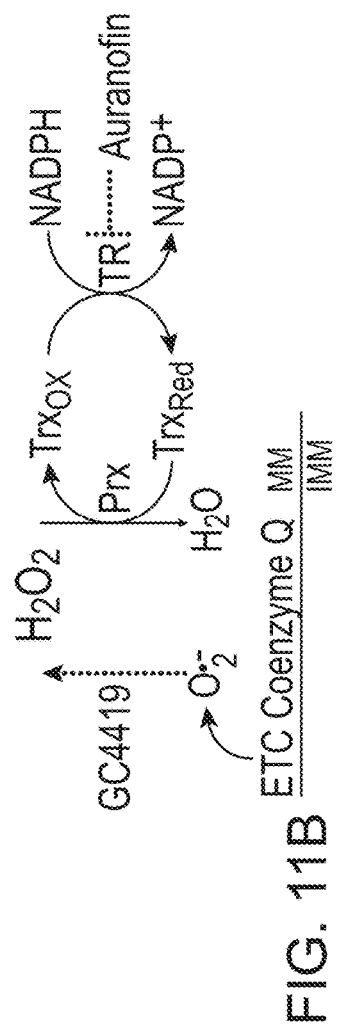
FIG. 11A
FIG. 11B

COMBINATION THERAPY FOR CANCER TREATMENT

The present disclosure generally relates to combination therapies for cancer treatment, including administration of a pentaaza macrocyclic ring complex, and active agent that is at least one of a thioredoxin reductase inhibitor and a glutathione-depleting agent.

Transition metal-containing pentaaza macrocyclic ring complexes having the macrocyclic ring system corresponding to Formula A have been shown to be effective in a number of animal and cell models of human disease, as well as in treatment of conditions afflicting human patients.

FORMULA A

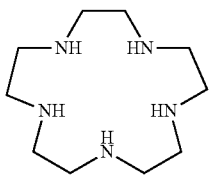

For example, in a rodent model of colitis, one such compound, GC4403, has been reported to very significantly reduce the injury to the colon of rats subjected to an experimental model of colitis (see Cuzzocrea et al., Europ. J. Pharmacol., 432, 79-89 (2001)).

(4403)

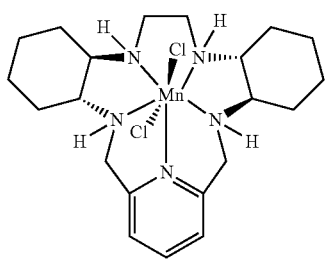

GC4403 has also been reported to attenuate the radiation damage arising both in a clinically relevant hamster model of acute, radiation-induced oral mucositis (Murphy et al., Clin. Can. Res., 14(13), 4292 (2008)), and lethal total body irradiation of adult mice (Thompson et al., Free Radical Res., 44(5), 529-40 (2010)). Similarly, another such compound, GC4419, has been shown to attenuate VEGFr inhibitor-induced pulmonary disease in a rat model (Tuder, et al., Am. J. Respir. Cell Mol. Biol., 29, 88-97 (2003)). Additionally, another such compound, GC4401 has been shown to provide protective effects in animal models of septic shock (S. Cuzzocrea, et. al., Crit. Care Med., 32(1), 157 (2004) and pancreatitis (S. Cuzzocrea, et. al., Shock, 22(3), 254-61 (2004)).

(4419)

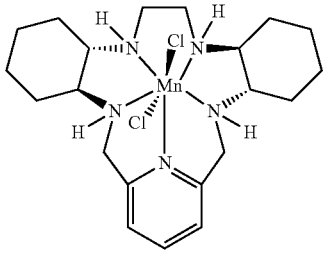

(4401)

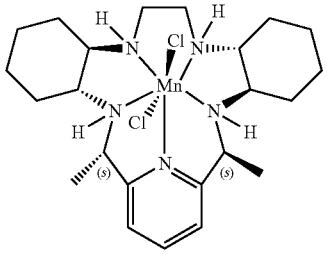

Certain of these compounds have also been shown to possess potent anti-inflammatory activity and prevent oxidative damage in vivo. For example, GC4403 has been reported to inhibit inflammation in a rat model of inflammation (Salvemini, et. al., Science, 286, 304 (1999)), and prevent joint disease in a rat model of collagen-induced arthritis (Salvemini et al., Arthritis & Rheumatism, 44(12), 2009-2021 (2001)). Yet others of these compounds, MdPAM and MnBAM, have shown in vivo activity in the inhibition of colonic tissue injury and neutrophil accumulation into colonic tissue (Weiss et al., The Journal of Biological Chemistry, 271(42), 26149-26156 (1996)). In addition, these compounds have been reported to possess analgesic activity and to reduce inflammation and edema in the rat-paw carrageenan hyperalgesia model, see, e.g., U.S. Pat. No. 6,180,620. Furthermore, certain of these compounds may variously be considered anti-oxidants, or to reduce oxidative stress.

Compounds of this class have also been shown to be safe and effective in the prevention and treatment of disease in human subjects. For example, GC4419 has been shown to reduce oral mucositis in head-and-neck cancer patients undergoing chemoradiation therapy (Anderson, C., Phase 1 Trial of Superoxide Dismutase (SOD) Mimetic GC4419 to Reduce Chemoradiotherapy (CRT)-Induced Mucositis (OM) in Patients (pts) with Mouth or Oropharyngeal Carcinoma (OCC), Oral Mucositis Research Workshop, MASCC/ISOO Annual Meeting on Supportive Care in Cancer, Copenhagen, Denmark (Jun. 25, 2015)).

In addition, transition metal-containing pentaaza macrocyclic ring complexes corresponding to this class have shown efficacy in the treatment of various cancers. For example, certain compounds corresponding to this class have been provided in combination with agents such as paclitaxel and gemcitabine to enhance cancer therapies, such as in the treatment of colorectal cancer and lung cancer (non-small cell lung cancer) (see, e.g., U.S. Pat. No. 9,998, 893). The GC4403 compound above has also been used for treatment in in vivo models of Meth A spindle cell spindle cell ascites tumor and renal carcinoma (Samlowski et al., Madame Curie Bioscience Database (Internet), 230-249 (2006)), and has also been used for treatment in in vivo models of spindle-cell squamous carcinoma (Samlowski et al., *Nature Medicine,* 9(6), 750-755 (2003)).

However, a need remains for enhanced methods for cancer treatment that provide improved efficacy in the killing of cancer cells, while also providing good selectivity in the killing of cancer cells as compared to normal cells. There also remains a need for enhanced methods of treatment to supplement cancer treatments such as radiation therapy and chemotherapy, to improve outcomes for patients receiving these treatments.

Among the various aspects of the present disclosure, therefore, is method of treating a cancer in a mammalian subject afflicted therewith. The method includes administering to the subject at least one active agent including one or more of a thioredoxin reductase inhibitor and a glutathione depleting agent, and administering to the subject a pentaaza macrocyclic ring complex corresponding to formula (I) below:

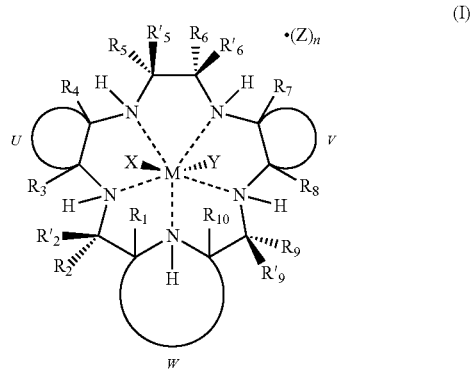

(I)

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Among the various aspects of the present disclosure, therefore, is a method of treating a cancer in a mammalian subject afflicted therewith, the method including administering to the subject at least one active agent including one or more of a thioredoxin reductase inhibitor and a glutathione-depleting agent, administering to the subject a pentaaza macrocyclic ring complex, and further administering to the subject a cancer therapy that is at least one of radiation therapy and chemotherapy. The pentaaza macrocyclic ring complex can correspond to the formula (I) below:

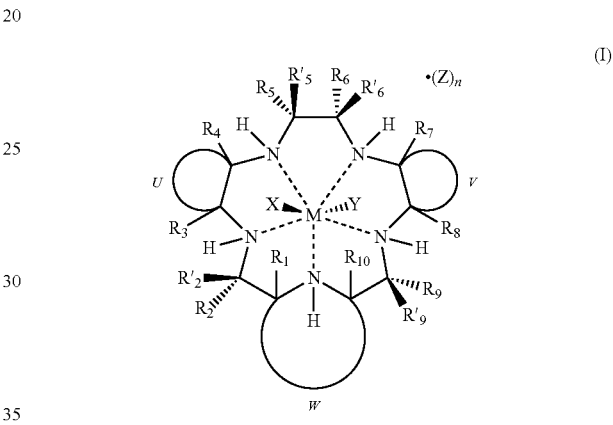

(I)

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Other objects and features will be in part apparent and in part pointed out hereinafter.

BRIEF DESCRIPTION OF THE DRAWINGS

FIGS. 11A-11B are schematic diagrams showing mechanisms by which intracellular levels of $H_2O_2$ can be increased with pentaaza macrocyclic ring complexes, thioredoxon reductase inhibitors and/or glutathione depleting agents.

ABBREVIATIONS AND DEFINITIONS

Figure 1:
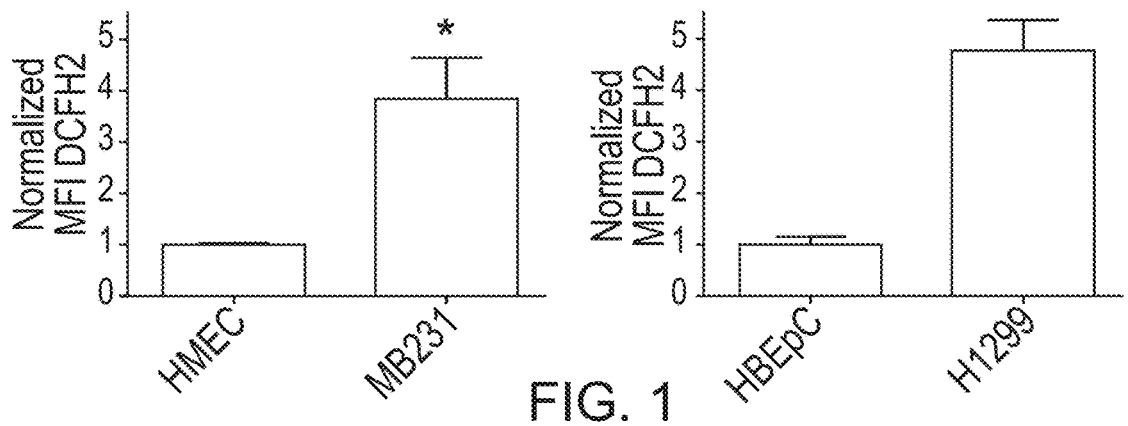
FIG. 1 shows the normalized mean fluorescence intensity (MFI) of 5- (and 6) carboxy-2',7' dichlorodihydrofluorescein diacetate (DCFH2) in cancer cells MB231 and H1299, as compared to normal HMEC or HBEpC cells, using the DCFH2 fluorescent probe as a non-specific oxidation sensitive probe.

The following definitions and methods are provided to better define the present invention and to guide those of ordinary skill in the art in the practice of the present invention. Unless otherwise noted, terms are to be understood according to conventional usage by those of ordinary skill in the relevant art.

"Acyl" means a —COR moiety where R is alkyl, haloalkyl, optionally substituted aryl, or optionally substituted heteroaryl as defined herein, e.g., acetyl, trifluoroacetyl, benzoyl, and the like.

"Acyloxy" means a —OCOR moiety where R is alkyl, haloalkyl, optionally substituted aryl, or optionally substituted heteroaryl as defined herein, e.g., acetyl, trifluoroacetyl, benzoyl, and the like.

"Alkoxy" means a —OR moiety where R is alkyl as defined above, e.g., methoxy, ethoxy, propoxy, or 2-propoxy, n-, iso-, or tert-butoxy, and the like.

"Alkyl" means a linear saturated monovalent hydrocarbon moiety such as of one to six carbon atoms, or a branched saturated monovalent hydrocarbon moiety, such as of three to six carbon atoms, e.g., $C_1$-$C_6$ alkyl groups such as methyl, ethyl, propyl, 2-propyl, butyl (including all isomeric forms), pentyl (including all isomeric forms), and the like.

Moreover, unless otherwise indicated, the term "alkyl" as used herein is intended to include both "unsubstituted alkyls" and "substituted alkyls," the latter of which refers to alkyl moieties having substituents replacing a hydrogen on one or more carbons of the hydrocarbon backbone. Indeed, unless otherwise indicated, all groups recited herein are intended to include both substituted and unsubstituted options.

The term "$C_{x-y}$" when used in conjunction with a chemical moiety, such as alkyl and aralkyl, is meant to include groups that contain from x to y carbons in the chain. For example, the term $C_{x-y}$ alkyl refers to substituted or unsubstituted saturated hydrocarbon groups, including straight chain alkyl and branched chain alkyl groups that contain from x to y carbon atoms in the chain.

"Alkylene" means a linear saturated divalent hydrocarbon moiety, such as of one to six carbon atoms, or a branched saturated divalent hydrocarbon moiety, such as of three to six carbon atoms, unless otherwise stated, e.g., methylene, ethylene, propylene, 1-methylpropylene, 2-methylpropylene, butylene, pentylene, and the like.

"Alkenyl" a linear unsaturated monovalent hydrocarbon moiety, such as of two to six carbon atoms, or a branched saturated monovalent hydrocarbon moiety, such as of three to six carbon atoms, e.g., ethenyl (vinyl), propenyl, 2-propenyl, butenyl (including all isomeric forms), pentenyl (including all isomeric forms), and the like.

"Alkaryl" means a monovalent moiety derived from an aryl moiety by replacing one or more hydrogen atoms with an alkyl group.

"Alkenylcycloalkenyl" means a monovalent moiety derived from an alkenyl moiety by replacing one or more hydrogen atoms with a cycloalkenyl group.

"Alkenylcycloalkyl" means a monovalent moiety derived from a cycloalkyl moiety by replacing one or more hydrogen atoms with an alkenyl group.

"Alkylcycloalkenyl" means a monovalent moiety derived from a cycloalkenyl moiety by replacing one or more hydrogen atoms with an alkyl group.

"Alkylcycloalkyl" means a monovalent moiety derived from a cycloalkyl moiety by replacing one or more hydrogen atoms with an alkyl group.

"Alkynyl" means a linear unsaturated monovalent hydrocarbon moiety, such of two to six carbon atoms, or a branched saturated monovalent hydrocarbon moiety, such as of three to six carbon atoms, e.g., ethynyl, propynyl, butynyl, isobutynyl, hexynyl, and the like.

"Alkoxy" means a monovalent moiety derived from an alkyl moiety by replacing one or more hydrogen atoms with a hydroxy group.

"Amino" means a —$NR^aR^b$ group where $R^a$ and $R^b$ are independently hydrogen, alkyl or aryl.

"Aralkyl" means a monovalent moiety derived from an alkyl moiety by replacing one or more hydrogen atoms with an aryl group. The term "arylalkyl" may also be used equivalently herein to refer to "aralkyl."

"Aryl" means a monovalent monocyclic or bicyclic aromatic hydrocarbon moiety of 6 to 10 ring atoms e.g., phenyl or naphthyl.

"Cycle" means a carbocyclic saturated monovalent hydrocarbon moiety of three to ten carbon atoms.

"Cycloalkyl" means a cyclic saturated monovalent hydrocarbon moiety of three to ten carbon atoms, e.g., cyclopropyl, cyclobutyl, cyclopentyl, or cyclohexyl, and the like.

"Cycloalkylalkyl" means a monovalent moiety derived from an alkyl moiety by replacing one or more hydrogen atoms with a cycloalkyl group, e.g., cyclopropylmethyl, cyclobutylmethyl, cyclopentylethyl, or cyclohexylethyl, and the like.

"Cycloalkylcycloalkyl" means a monovalent moiety derived from a cycloalkyl moiety by replacing one or more hydrogen atoms with a cycloalkyl group.

"Cycloalkenyl" means a cyclic monounsaturated monovalent hydrocarbon moiety of three to ten carbon atoms, e.g., cyclopropenyl, cyclobutenyl, cyclopentenyl, or cyclohexenyl, and the like.

"Cycloalkenylalkyl" means a monovalent moiety derived from an alkyl moiety by replacing one or more hydrogen atoms with a cycloalkenyl group, e.g., cyclopropenylmethyl, cyclobutenylmethyl, cyclopentenylethyl, or cyclohexenylethyl, and the like.

"Ether" means a monovalent moiety derived from an alkyl moiety by replacing one or more hydrogen atoms with an alkoxy group.

"Halo" means fluoro, chloro, bromo, or iodo, preferably fluoro or chloro.

"Heterocycle" or "heterocyclyl" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group is a saturated ring and is not fused to aryl or heteroaryl ring as stated above, it is also referred to herein as saturated monocyclic heterocyclyl.

"Heteroaryl" means a monovalent monocyclic or bicyclic aromatic moiety of 5 to 10 ring atoms where one or more, preferably one, two, or three, ring atoms are heteroatom selected from N, O, or S, the remaining ring atoms being carbon. Representative examples include, but are not limited to, pyrrolyl, pyrazolyl, thienyl, thiazolyl, imidazolyl, furanyl, indolyl, isoindolyl, oxazolyl, isoxazolyl, benzothiazolyl, benzoxazolyl, benzimidazolyl, quinolinyl, isoquinolinyl, pyridinyl, pyrimidinyl, pyrazinyl, pyridazinyl, triazolyl, tetrazolyl, and the like.

"Nitro" means —$NO_2$.

"Organosulfur" means a monovalent moiety a —SR group where R is hydrogen, alkyl or aryl.

"Substituted alkyl," "substituted cycle," "substituted phenyl," "substituted aryl," "substituted heterocycle," and "substituted nitrogen heterocycles" means an alkyl, cycle, aryl, phenyl, heterocycle or nitrogen-containing heterocycle, respectively, optionally substituted with one, two, or three substituents, such as those independently selected from alkyl, alkoxy, alkoxyalkyl, halo, hydroxy, hydroxyalkyl, or organosulfur.

"Thioether" means a monovalent moiety derived from an alkyl moiety by replacing one or more hydrogen atoms with an —SR group wherein R is alkyl.

As used herein, (i) the compound referred to herein and in the Figures as compound 401, 4401 or GC4401 is a reference to the same compound, (ii) the compound referred to herein and in the Figures as compound 403, 4403 or GC4403 is a reference to the same compound, (iii) the compound referred to herein and in the Figures as compound 419, 4419 or GC4419 is a reference to the same compound, and (iv) the compound referred to herein and in the Figures as compound 444, 4444 or GC4444 is a reference to the same compound.

DETAILED DESCRIPTION

Aspects of the present disclosure are directed to the treatment of cancer by administration of a pentaaza macrocyclic ring complex according to Formula (I) with at least one active agent that is at least one of a thioredoxin reductase inhibitor and a glutathione depleting agent. Embodiments of the treatment can provide for the enhanced killing of cancerous cells in patients in need thereof, as well as improved selectivity in the killing of cancer cells versus normal cells. The combinations of these compounds may also be administered as a supplement to another cancer therapy, such as a radiation therapy and/or chemotherapy, to improve the efficacy thereof.

Without being limited to any particular theory, it is believed that the combination of the pentaaza macrocyclic ring complex of Formula (I) with the active agent that is at least one of a thioredoxin reductase inhibitor and a glutathione depleting agent may result in an increase in intracellular $H_2O_2$ levels in cancer cells, thereby leading to increased cytotoxicity. In particular, differences in mitochondrial oxidative metabolism between cancer and normal cells lead to increased levels of reactive oxygen species (ROS) such as $O_2^-$ (superoxide anion) and $H_2O_2$. Glutathione and thioredoxin pathways are thus upregulated in cancer cells to compensate for this difference, by providing reducing agents to remove the reactive oxygen species. (Zhou et al., *Adv. Cancer Res.* 122, 1-67 (2014); Aykin-Burns et al., *Biochem J.*, 418 (1), 29-37 (2009); Aykin-Burns et al., *J. Biol. Chem.*, 280(6), 4254-4263 (2005); Spitz et al., *Ann. NY Acad. Sci.*, 899, 349-362 (2000); Fath et al. *Clin Cancer Res.*, 17(19), 6206-6217 (2011); Hadzic et al., *Free Radic. Biol. Med.*, 48(8), 1024-1033 (2010); Scarbrough et al., *Free Radic Biol Med.*, 52 (2), 436-443 (2012)).

Accordingly, embodiments of the invention are directed to exploiting this difference in oxygen metabolism between cancer and normal cells to provide enhanced cancer treatment, with a combination of compounds that unexpectedly exhibits synergistic effects. In particular, embodiments of the invention provide for the administration of an active agent that reduces that ability of cells to regulate $H_2O_2$, which may selectively impact cancer cells that exhibit increased levels of reactive oxygen species. Synergistic effects in cancer cell cytotoxicity are then unexpectedly achieved via administration of a compound that removes one reactive oxygen species, superoxide anion, and converts it into another, $H_2O_2$, with two superoxide equivalents being removed for each $H_2O_2$ equivalent created. The combined administration of the compounds both attacks the mechanism by which $H_2O_2$ is eliminated from cancer cells, and also promotes the formation of new $H_2O_2$, resulting in a synergistic increase in $H_2O_2$ and cytotoxicity for the cancer cells.

In one embodiment, to inhibit one or more of the glutathione and/or thioredoxin-dependent metabolism of $H_2O_2$, at least one of a thiorexodin reductase inhibitor and a glutathione-depleting agent can be provided. Furthermore, the compound to promote $H_2O_2$ formation is a pentaaza macrocyclic ring complex according to Formula (I), which may increases the production of $H_2O_2$ from superoxide in cells. (Buettner et al., *Free Radic Biol. Med.*, 41(8), 1338-1350 (2006). Embodiments of a mechanism by which intracellular levels or fluxes of $H_2O_2$ may be increased by the combined administration of the compounds are shown in FIGS. 11A-11B, where GC4419 is used as the pentaaza macrocyclic ring complex, and auranofin is provided as a thioredoxin reductase inhibitor. The mechanism as shown thus results in an overall increase in the $H_2O_2$ levels in cancer cells by promotion of $H_2O_2$ formation from superoxide by the GC4419, and simultaneous inhibition of thioredoxin reductase by auranofin to reduce metabolism of the $H_2O_2$. Similarly, a glutathione depleting agent can be provided to inhibit glutathione-dependent $H_2O_2$ metabolism pathways. An embodiment of a mechanism by which glutathione depletion can contribute to increased intracellular levels of $H_2O_2$, with BSO as a glutathione depleting agent provided as a part of a combination therapy, is also shown in FIGS. 11A-11B.

Accordingly, by providing a combination of the pentaaza macrocyclic ring complex according to Formula (1) and the active agent that is at least one of a thioredoxin reductase inhibitor and a glutathione-depleting agent, it has been unexpectedly discovered that synergistic effects in the killing of cancer cells can be provided. The combination can thus be administered for the treatment of cancer, as well as to supplement conventional cancer treatment therapies, with improved treatment efficacy.

Transition Metal Pentaaza Macrocyclic Ring Complex

In one embodiment, the pentaaza macrocyclic ring complex corresponds to the complex of Formula (I):

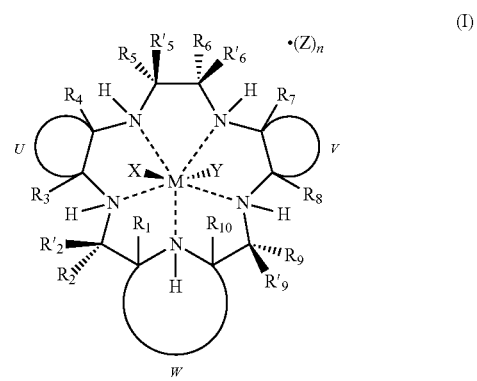

wherein
M is $Mn^{2+}$ or $Mn^{3+}$;
$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl;
U, together with the adjacent carbon atoms of the macrocycle, forms a fused substituted or unsubstituted, saturated, partially saturated or unsaturated, cycle or heterocycle having 3 to 20 ring carbon atoms;
V, together with the adjacent carbon atoms of the macrocycle, forms a fused substituted or unsubstituted, saturated, partially saturated or unsaturated, cycle or heterocycle having 3 to 20 ring carbon atoms;
W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;
X and Y represent suitable ligands which are derived from any monodentate or polydentate coordinating ligand or ligand system or the corresponding anion thereof;
Z is a counterion;
n is an integer from 0 to 3; and
the dashed lines represent coordinating bonds between the nitrogen atoms of the macrocycle and the transition metal, manganese.

As noted above in connection with the pentaaza macrocyclic ring complex of Formula (I), M is $Mn^{2+}$ or $Mn^{3+}$. In one particular embodiment in which the pentaaza macrocyclic ring complex corresponds to Formula (I), M is $Mn^{2+}$. In another particular embodiment in which the pentaaza macrocyclic ring complex corresponds to Formula (I), M is $Mn^{3+}$.

In the embodiments in which one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are hydrocarbyl, for example, suitable hydrocarbyl moieties include, but are not limited to alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and aralkyl. In one embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, or heterocyclyl. More preferably in this embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or lower alkyl (e.g., $C_1$-$C_6$ alkyl, more typically $C_1$-$C_4$ alkyl). Thus, for example, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ may be independently hydrogen, methyl, ethyl, propyl, or butyl (straight, branched, or cyclic). In one preferred embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or methyl.

In one preferred embodiment in which the pentaaza macrocyclic ring complex corresponds to Formula (I), $R_1$, $R_2$, $R'_2$, $R_3$, $R_4$, $R_5$, $R'_5$, $R_7$, $R_8$, $R_9$, $R'_9$, and $R_{10}$ are each hydrogen and one of $R_6$ and $R'_6$ is hydrogen and the other of $R_6$ and $R'_6$ is methyl. In this embodiment, for example, $R_1$, $R_2$, $R'_2$, $R_3$, $R_4$, $R_5$, $R'_5$, $R_6$, $R_7$, $R_8$, $R_9$, $R'_9$, and $R_{10}$ may each be hydrogen while $R'_6$ is methyl. Alternatively, for example, $R_1$, $R_2$, $R'_2$, $R_3$, $R_4$, $R_5$, $R'_5$, $R'_6$, $R_7$, $R_8$, $R_9$, $R'_9$, and $R_{10}$ may each be hydrogen while $R_6$ is methyl. In another preferred embodiment in which the pentaaza macrocyclic ring complex corresponds to Formula (I), $R_1$, $R_3$, $R_4$, $R_5$, $R'_5$, $R'_6$, $R_7$, $R_8$, and $R_{10}$ are each hydrogen, one of $R_2$ and $R'_2$ is hydrogen and the other of $R_2$ and $R'_2$ is methyl, and one of $R_9$ and $R'_9$ is hydrogen and the other of $R_9$ and $R'_9$ is methyl. In this embodiment, for example, $R_1$, $R'_2$, $R_3$, $R_4$, $R_5$, $R'_5$, $R_7$, $R_8$, $R_9$, and $R_{10}$ may each be hydrogen while $R_2$ and $R'_9$ are methyl. Alternatively, for example, $R_1$, $R_2$, $R_3$, $R_4$, $R_5$, $R'_5$, $R_7$, $R_8$, $R'_9$, and $R_{10}$ may each be hydrogen while $R'_2$ and $R_9$ are methyl. In another embodiment in which the pentaaza macrocyclic ring complex corresponds to Formula (I), $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are each hydrogen.

In certain embodiments the U and V moieties are independently substituted or unsubstituted fused cycloalkyl moieties having 3 to 20 ring carbon atoms, more preferably 4 to 10 ring carbon atoms. In a particular embodiment, the U and V moieties are each trans-cyclohexanyl fused rings.

In certain embodiments the W moiety is a substituted or unsubstituted fused heteroaromatic moiety. In a particular embodiment, the W moiety is a substituted or unsubstituted fused pyridino moiety. Where W is a substituted fused pyridino moiety, for example, the W moiety is typically substituted with a hydrocarbyl or substituted hydrocarbyl moiety (e.g., alkyl, substituted alkyl) at the ring carbon atom positioned para to the nitrogen atom of the heterocycle. In a one preferred embodiment, the W moiety is an unsubstituted fused pyridino moiety.

As noted above, X and Y represent suitable ligands which are derived from any monodentate or polydentate coordinating ligand or ligand system or the corresponding anion thereof (for example benzoic acid or benzoate anion, phenol or phenoxide anion, alcohol or alkoxide anion). For example, X and Y may be selected from the group consisting of halo, oxo, aquo, hydroxo, alcohol, phenol, dioxygen, peroxo, hydroperoxo, alkylperoxo, arylperoxo, ammonia, alkylamino, arylamino, heterocycloalkyl amino, heterocyloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof, among other possibilities. In one embodiment, X and Y if present, are independently selected from the group consisting of halo, nitrate, and bicarbonate ligands. For example, in this embodiment, X and Y, if present, are halo ligands, such as chloro ligands.

Furthermore, in one embodiment X and Y correspond to —O—C(O)—$X_1$, where each $X_1$ is —C($X_2$)($X_3$)($X_4$), and each $X_1$ is independently substituted or unsubstituted phenyl or —C(—$X_2$)(—$X_3$)(—$X_4$);

each $X_2$ is independently substituted or unsubstituted phenyl, methyl, ethyl or propyl;

each $X_3$ is independently hydrogen, hydroxyl, methyl, ethyl, propyl, amino, —$X_5$C(=O)$R_{13}$ where $X_5$ is NH or O, and $R_{13}$ is C1-C18 alkyl, substituted or unsubstituted aryl or C1-C18 aralkyl, or —O$R_{14}$, where $R_{14}$ is C1-C18 alkyl, substituted or unsubstituted aryl or C1-C18 aralkyl, or together with $X_4$ is (=O); and each $X_4$ is independently hydrogen or together with $X_3$ is (=O).

In yet another embodiment, X and Y are independently selected from the group consisting of charge-neutralizing anions which are derived from any monodentate or polydentate coordinating ligand and a ligand system and the corresponding anion thereof; or X and Y are independently attached to one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$.

In the pentaaza macrocyclic ring complex corresponding to Formula (I), Z is a counterion (e.g., a charge-neutralizing anion), wherein n is an integer from 0 to 3. In general, Z may correspond to counterions of the moieties recited above in connection for X and Y.

In combination, among certain preferred embodiments are pentaaza macrocyclic ring complexes corresponding to Formula (I) wherein M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or lower alkyl;

U and V are each trans-cyclohexanyl fused rings;

W is a substituted or unsubstituted fused pyridino moiety;

X and Y are ligands; and

Z, if present, is a charge-neutralizing anion.

More preferably in these embodiments, M is $Mn^{2+}$; $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or methyl; U and V are each trans-cyclohexanyl fused rings; W is an unsubstituted fused pyridino moiety; and X and Y are independently halo ligands (e.g., fluoro, chloro, bromo, iodo). Z, if present, may be a halide anion (e.g., fluoride, chloride, bromide, iodide).

In yet another embodiment, the pentaaza macrocyclic ring complex is represented by formula (II) below:

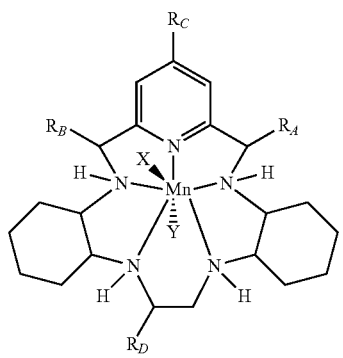

(II)

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, $CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl.

Furthermore, in one embodiment, the pentaaza macrocyclic ring complex is represented by formula (III) or formula (IV):

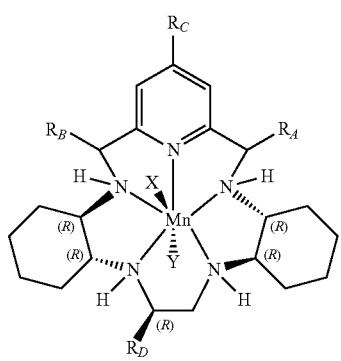

(III)

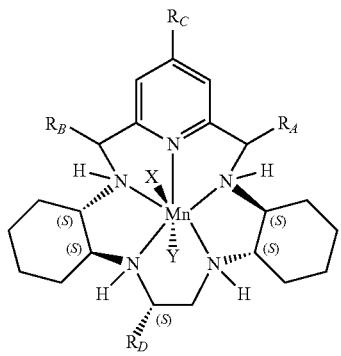

(IV)

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SOR_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl.

Certain particularly preferred pentaaza macrocyclic ring complexes for use in the methods and compositions described herein include those corresponding to Formulae (V)-(XVI):

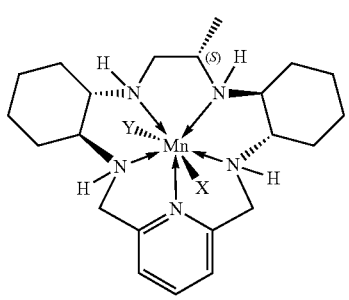

(V)

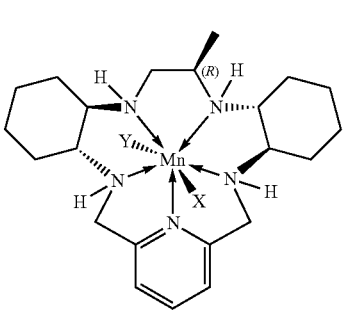

(VI)

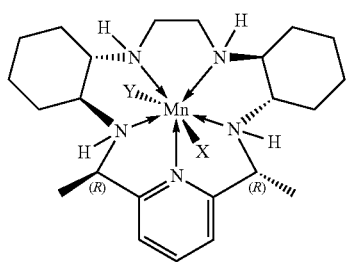
(VII)
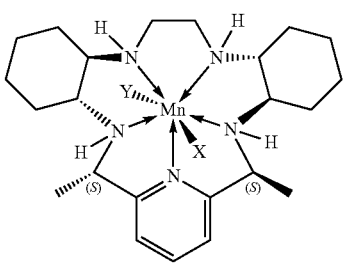
(VIII)
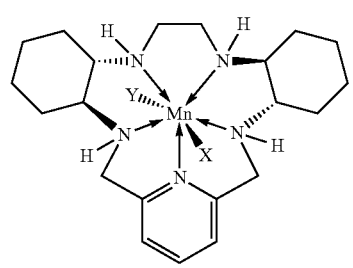
(IX)
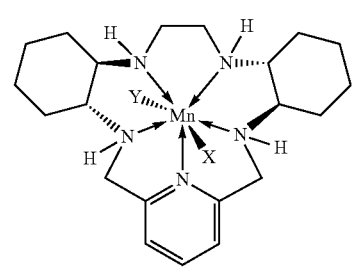
(X)
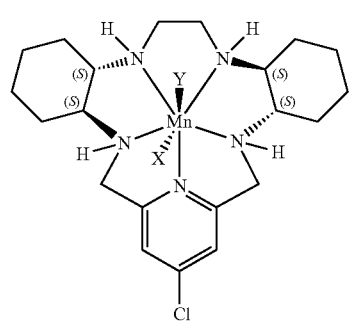
(XI)
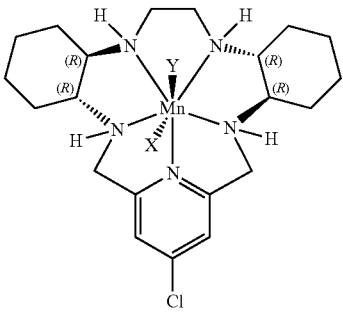
(XII)
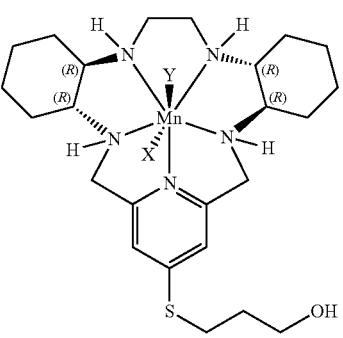
(XIII)
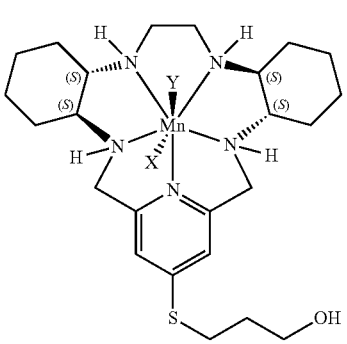
(XIV)
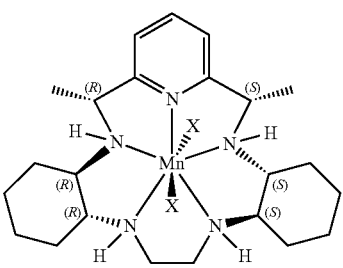
(XV)
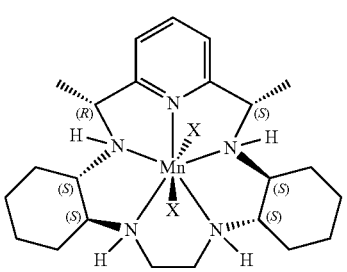
(XVI)
wherein X and Y in each of Formulae are independently ligands. For example, according to one embodiment, the pentaaza macrocyclic ring complex for use in the methods and compositions described herein include those corresponding to the Formulae above, with X and Y in each of these formulae being halo, such as chloro. Alternatively, X and Y may be ligands other than chloro.

In one embodiment, X and Y in any of the formulas herein are independently selected from the group consisting of fluoro, chloro, bromo and iodo anions. In yet another embodiment, X and Y in any of the formulas herein are independently selected from the group consisting of alkyl carboxylates, aryl carboxylates and arylalkyl carboxylates. In yet another embodiment, X and Y in any of the formulas herein are independently amino acids.

In one embodiment, the pentaaza macrocyclic ring complex has the following Formula (IA):

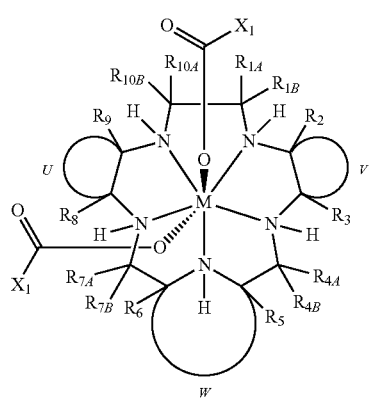

(IA)

wherein
M is $Mn^{2+}$ or $Mn^{3+}$;
$R_{1A}$, $R_{1B}$, $R_2$, $R_3$, $R_{4A}$, $R_{4B}$, $R_5$, $R_6$, $R_{7A}$, $R_{7B}$, $R_8$, $R_9$, $R_{10A}$, and $R_{10B}$ are independently hydrogen, hydrocarbyl, substituted hydrocarbyl, heterocyclyl, an amino acid side chain moiety, or a moiety independently selected from the group consisting of $-OR_{11}$, $-NR_{11}R_{12}$, $-COR_{11}$, $-CO_2R_{11}$, $-C(=O)(NR_{11}R_{12}$, $-SR_{11}$, $-SOR_{11}$, $-SO_2R_{11}$, $-SO_2NR_{11}R_{12}$, $-N(OR_{11})(R_{12})$, $-P(=O)(OR_{11})(OR_{12})$, $-P(=O)(OR_{11})(R_{12})$, and $-OP(=O)(OR_{11})(OR_{12})$, wherein $R_{11}$ and $R_{12}$ are independently hydrogen or alkyl;
U, together with the adjacent carbon atoms of the macrocycle, forms a fused substituted or unsubstituted, saturated, partially saturated or unsaturated, cycle or heterocycle having 3 to 20 ring carbon atoms;
V, together with the adjacent carbon atoms of the macrocycle, forms a fused substituted or unsubstituted, saturated, partially saturated or unsaturated, cycle or heterocycle having 3 to 20 ring carbon atoms;
W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_5$ and $R_6$ attached to the carbon atoms which are both part of the heterocycle and the macrocycle are absent; wherein
each $X_1$ is independently substituted or unsubstituted phenyl or $-C(-X_2)(-X_3)(-X_4)$;
each $X_2$ is independently substituted or unsubstituted phenyl or alkyl;

each $X_3$ is independently hydrogen, hydroxyl, alkyl, amino, $-X_5C(=O)R_{13}$ where $X_5$ is NH or O, and $R_{13}$ is $C_1$-$C_{18}$ alkyl, substituted or unsubstituted aryl or $C_1$-$C_{18}$ aralkyl, or $-OR_{14}$, where $R_{14}$ is $C_1$-$C_{18}$alkyl, substituted or unsubstituted aryl or $C_1$-$C_{18}$ aralkyl, or together with $X_4$ is (=O);
each $X_4$ is independently hydrogen or together with $X_3$ is (=O); and
the bonds between the transition metal M and the macrocyclic nitrogen atoms and the bonds between the transition metal M and the oxygen atoms of the axial ligands $-OC(=O)X_1$ are coordinate covalent bonds.

In one embodiment, within Formula (IA), and groups contained therein, in one group of compounds $X_1$ is $-C(-X_2)(-X_3)(-X_4)$ and each $X_2$, $X_3$, and $X_4$, in combination, corresponds to any of the combinations identified in the following table:

| Combination | $X_2$ | $X_3$ | $X_4$ |
|---|---|---|---|
| 1 | Ph | H | H |
| 2 | Ph | OH | H |
| 3 | Ph | $NH_2$ | H |
| 4 | Ph | | =O |
| | | ($X_3$ and $X_4$ in combination) | |
| 5 | Ph | $CH_3$ | H |
| 6 | $CH_3$ | H | H |
| 7 | $CH_3$ | OH | H |
| 8 | $CH_3$ | $NH_2$ | H |
| 9 | $CH_3$ | | =O |
| | | ($X_3$ and $X_4$ in combination) | |

Furthermore, within embodiment (IA), and groups contained therein, in one group of compounds $X_1$ is $C(-X_2)(-X_3)(-X_4)$, and $X_3$ is $-X_5C(=O)R_{13}$, such that the combinations of $X_2$, $X_3$ and $X_4$ include any of the combinations identified in the following table:

| Combination | $X_2$ | $X_3$ | $X_4$ |
|---|---|---|---|
| 1 | Ph | $NHC(=O)R_{13}$ | H |
| 2 | Ph | $OC(=O)R_{13}$ | H |
| 3 | $CH_3$ | $NHC(=O)R_{13}$ | H |
| 4 | $CH_3$ | $OC(=O)R_{13}$ | H | where $R_{13}$ is $C_1$-$C_{18}$ alkyl, substituted or unsubstituted aryl or $C_1$-$C_{18}$ aralkyl, or $-OR_{14}$, where $R_{14}$ is $C_1$-$C_{18}$ alkyl, substituted or unsubstituted aryl or $C_1$-$C_{18}$ aralkyl.

In one embodiment, the pentaaza macrocyclic ring complex corresponding to Formula (IA) is one of the complexes Formula (IE), such as $(IE_{R1})$, $(IE_{S1})$, $(IE_{R2})$, $(IE_{S2})$, $(IE_{R3})$, or $(IE_{S3})$:

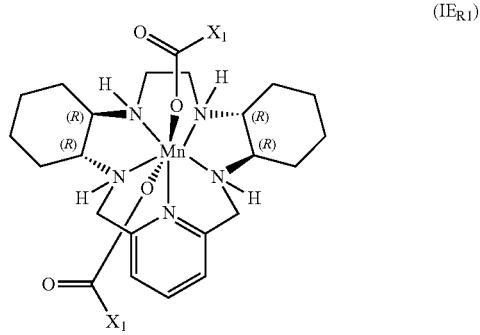

$(IE_{R1})$ (IE<sub>S1</sub>)

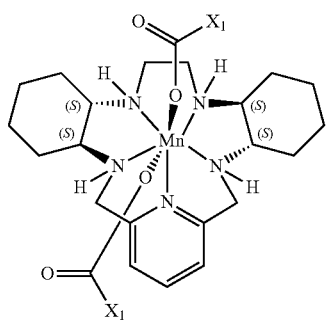

(IE<sub>R2</sub>)

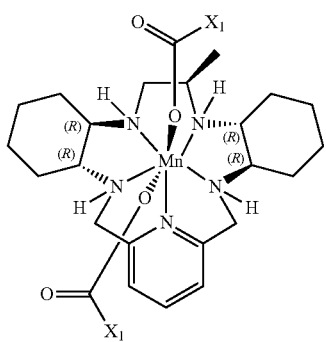

(IE<sub>S2</sub>)

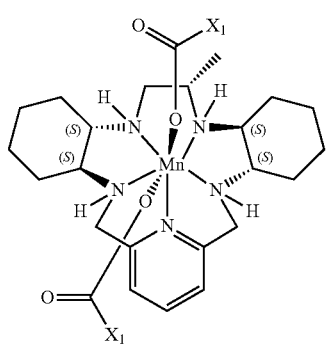

(IE<sub>R3</sub>)

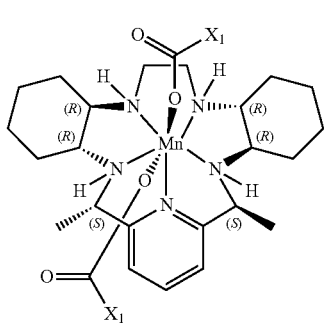

(IE<sub>S3</sub>)

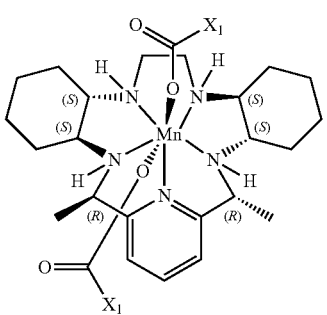

wherein
M is $Mn^{+2}$ or $Mn^{+3}$;
each $X_1$ is independently substituted or unsubstituted phenyl or —C($X_2$)($X_3$)($X_4$);
each $X_2$ is independently substituted or unsubstituted phenyl, methyl, ethyl, or propyl;
each $X_3$ is independently hydrogen, hydroxyl, methyl, ethyl, propyl, amino, or together with $X_4$ is =O;
each $X_4$ is independently hydrogen or together with $X_3$ is =O; and
the bonds between the manganese and the macrocyclic nitrogen atoms and the bonds between the manganese and the oxygen atoms of the axial ligands —OC(O)$X_1$ are coordinate covalent bonds.

In one embodiment, each $X_1$ is —C($X_2$)($X_3$)($X_4$) and each —C($X_2$)($X_3$)($X_4$) corresponds to any of combinations 1 to 9 appearing in the table for Formula (IA) above.

In yet another embodiment, the X and Y in pentaaza macrocyclic ring complex of Formula (I) correspond to the ligands in Formulas (IA) or (IE). For example, X and Y in the complex of Formula (I) may correspond to —O—C(O)—$X_1$, where $X_1$ is as defined for the complex of Formula (IA) and (IE) above.

In one embodiment, pentaaza macrocyclic ring complexes corresponding to Formula (I) (e.g., of Formula (I) or any of the subsets of Formula (I) corresponding to Formula (II)-(XIV), (IA and (IE) and others described herein), can comprise any of the following structures:

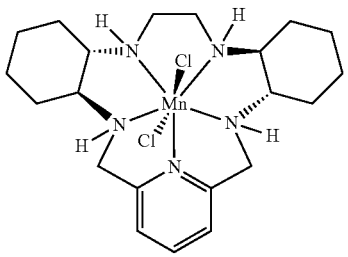

(4419)

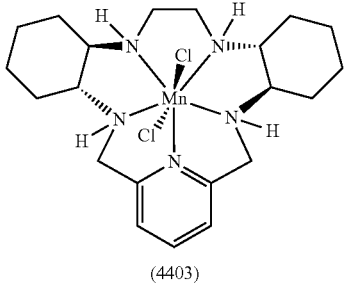

(4403)

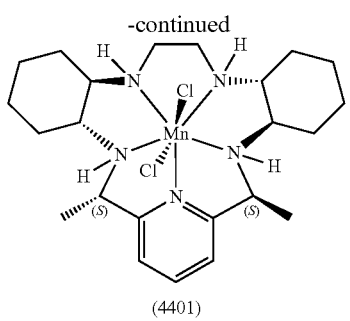

(4401)

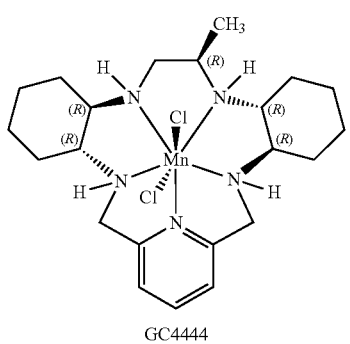

GC4444

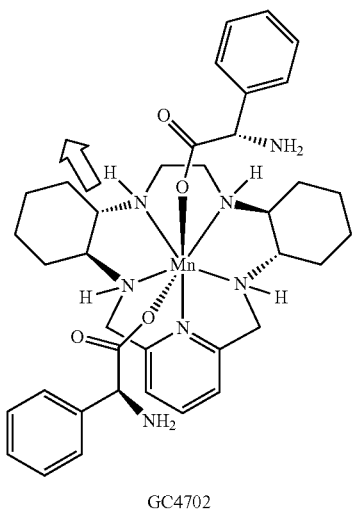

GC4702

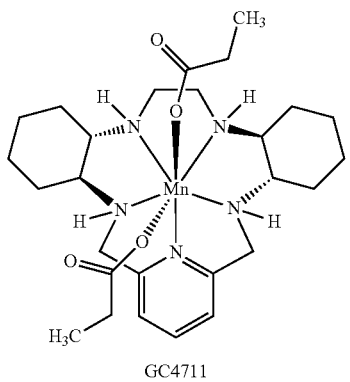

GC4711

In a particularly preferred embodiment, the pentaaza macrocyclic complex corresponds to Formula (XVII) or Formula (XVIII):

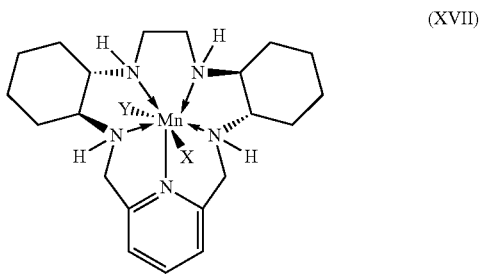

(XVII)

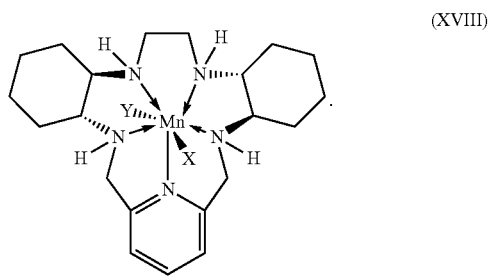

(XVIII)

For example, the pentaaza macrocyclic ring complex may correspond to at least one of the complexes below:

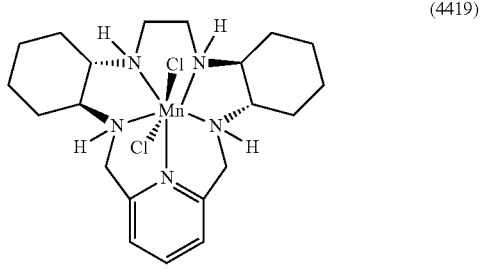

(4419)

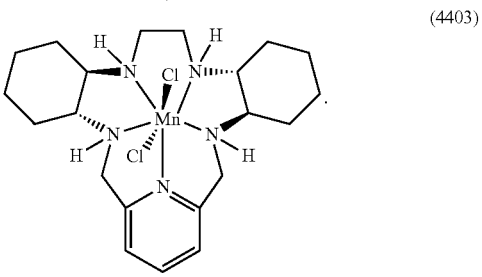

(4403)

The chemical structures of 4403 (dichloro complex form of XVII described, for example, in Riley, D. P., Schall, O. F., 2007, *Advances in Inorganic Chemistry*, 59: 233-263) and of 4419 herein (such as the dichloro complex form of XVIII), are identical except that they possess mirror image chirality; that is, the enantiomeric structures are non-superimposable.

In yet another embodiment, the pentaaza macrocyclic ring complex may correspond to at least one of the complexes below, and/or an enantiomer thereof:

(4432)

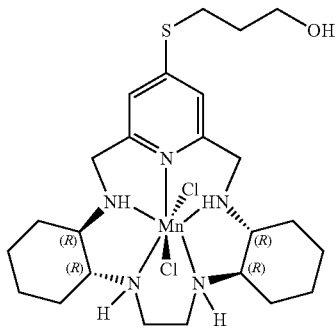

(4409)

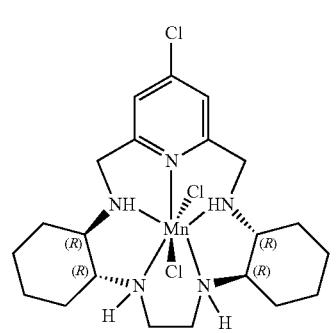

In yet another embodiment, the pentaaza macrocyclic ring complex corresponds to Formula (XIX):

(XIX)

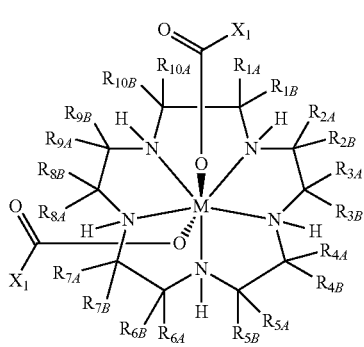

wherein
M is a transition metal (e.g., $Mn^{2+}$, $Mn^{3+}$);
$R_{1A}$, $R_{1B}$, $R_{2A}$, $R_{2B}$, $R_{3A}$, $R_{3B}$, $R_{4A}$, $R_{4B}$, $R_{5A}$, $R_{5B}$, $R_{6A}$, $R_{6B}$, $R_{7A}$, $R_{7B}$, $R_{8A}$, $R_{8B}$, $R_{9A}$, $R_{9B}$, $R_{10A}$, and $R_{10B}$ are independently:
 (i) hydrogen;
 (ii) a moiety independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, heterocyclyl, and aralkyl radicals and radicals attached to the α-carbon of amino acids (i.e., α-amino acids); or
 (iii) a moiety independently selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, —$OP(O)(OR_{11})(OR_{12})$, and substituents attached to the α-carbon of amino acids (i.e., α-amino acids), wherein $R_{11}$ and $R_{12}$ are independently hydrogen or alkyl;
 (iv) a member of a substituted or unsubstituted, saturated, partially saturated, or unsaturated cycle or heterocycle containing 3 to 20 carbon ring atoms comprising
  (a) $R_{1A}$ or $R_{1B}$ and $R_{2A}$ or $R_{2B}$; $R_{3A}$ or $R_{3B}$ and $R_{4A}$ or $R_{4B}$; $R_{5A}$ or $R_{5B}$ and $R_{6A}$ or $R_{6B}$; $R_{7A}$ or $R_{7B}$ and $R_{8A}$ or $R_{8B}$; $R_{9A}$ or $R_{9B}$ and $R_{10A}$ or $R_{10B}$ together with the carbon atoms to which they are respectively attached;
  (b) $R_{10A}$ or $R_{10B}$ and $R_{1A}$ or $R_{1B}$; $R_{2A}$ or $R_{2B}$ and $R_{3A}$ or $R_{3B}$; $R_{4A}$ or $R_{4B}$ and $R_{5A}$ or $R_{5B}$; $R_{6A}$ or $R_{6B}$ and $R_{7A}$ or $R_{7B}$, or $R_{8A}$ or $R_{8B}$ and $R_{9A}$ or $R_{9B}$ together with the carbon atoms to which they are respectively attached; or
  (c) $R_{1A}$ and $R_{1B}$; $R_{2A}$ and $R_{2B}$; $R_{3A}$ and $R_{3B}$; $R_{4A}$ and $R_{4B}$; $R_{5A}$ and $R_{5B}$; $R_{6A}$ and $R_{6B}$; $R_{7A}$ and $R_{8B}$; $R_{8A}$ and $R_{8B}$; $R_{9A}$ and $R_{9B}$; or $R_{10A}$ and $R_{10B}$ together with the carbon atoms to which they are respectively attached; or
 (v) a combination of any of (i) through (iv) above;
each $X_1$ is independently substituted or unsubstituted phenyl or —$C(—X_2)(—X_3)(—X_4)$;
each $X_2$ is independently substituted or unsubstituted phenyl or substituted or unsubstituted alkyl;
each $X_3$ is independently hydrogen, hydroxyl, alkyl, amino, or together with $X_4$ is =O;
each $X_4$ is independently hydrogen or together with $X_3$ is =O; and
the bonds between the transition metal, manganese, and the macrocyclic nitrogen atoms and the bonds between the transition metal, manganese, and the oxygen atoms of the axial ligands —$OC(O)X_1$ are coordinate covalent bonds.

In one embodiment, the pentaaza macrocyclic ring complex corresponding to Formula (XIX) is one of the complexes Formulae ($IE_{R1}$), ($IE_{S1}$), ($IE_{R2}$), ($IE_{S2}$), ($IE_{R3}$), or ($IE_{S3}$) described above.

In one embodiment, each $X_1$ is —$C(X_2)(X_3)(X_4)$ and each —$C(X_2)(X_3)(X_4)$ corresponds to any of combinations 1 to 7 appearing in the following table:

| Combination | $X_2$ | $X_3$ | $X_4$ |
|---|---|---|---|
| 1 | Ph | H | H |
| 2 | Ph | OH | H |
| 3 | Ph | $NH_2$ | H |
| 4 | Ph | =O ($X_3$ and $X_4$ in combination) | |
| 5 | Ph | $CH_3$ | H |
| 6 | $CH_3$ | H | H |
| 7 | $CH_3$ | OH | H |

In yet another embodiment, the X and Y in pentaaza macrocyclic ring complex of formula (1) correspond to the ligands in formula (XIX). For example, X and Y in the complex of formula (1) may correspond to —O—C(O)—$X_1$, where $X_1$ is as defined for the complex of Formula (XIX) above.

In one embodiment, the enantiomeric purity of the pentaaza macrocyclic ring complex is greater than 95%, more preferably greater than 98%, more preferably greater than 99%, and most preferably greater than 99.5%. As used herein, the term "enantiomeric purity" refers to the amount of a compound having the depicted absolute stereochemistry, expressed as a percentage of the total amount of the depicted compound and its enantiomer. In one embodiment, the diastereomeric purity of the pentaaza macrocyclic ring complex is greater than 98%, more preferably greater than 99%, and most preferably greater than 99.5%. As used herein, the term "diastereomeric purity" refers to the amount of a compound having the depicted absolute stereochemistry, expressed as a percentage of the total amount of the depicted compound and its diastereomers. Methods for determining diastereomeric and enantiomeric purity are well-known in the art. Diastereomeric purity can be determined by any analytical method capable of quantitatively distinguishing between a compound and its diastereomers, such as high performance liquid chromatography (HPLC). Similarly, enantiomeric purity can be determined by any analytical method capable of quantitatively distinguishing between a compound and its enantiomer. Examples of suitable analytical methods for determining enantiomeric purity include, without limitation, optical rotation of plane-polarized light using a polarimeter, and HPLC using a chiral column packing material.

In one embodiment, a therapeutically effective amount of the pentaaza macrocyclic ring complex may be an amount sufficient to provide a peak plasma concentration of at least 0.1 µM when administered to a patient. For example, in one embodiment, the pentaaza macrocyclic ring complex may be administered in an amount sufficient to provide a peak plasma concentration of at least 1 µM when administered to a patient. In yet another embodiment, the pentaaza macrocyclic ring complex may be administered in an amount sufficient to provide a peak plasma concentration of at least 10 µM when administered to a patient. Generally, the pentaaza macrocyclic ring complex will not be administered in an amount that would provide a peak plasma concentration greater than 40 µM when administered to a patient. For example, the pentaaza macrocyclic ring complex may be administered in an amount sufficient to provide a peak plasma concentration in the range of from 0.1 µM to 40 µM in a patient. As another example, the pentaaza macrocyclic ring complex may be administered in an amount sufficient to provide a peak plasma concentration in the range of from 0.5 µM to 20 µM in a patient. As another example, the pentaaza macrocyclic ring complex may be administered in an amount sufficient to provide a peak plasma concentration in the range of from 1 µM to 10 µM in a patient.

In yet another embodiment, a dose of the pentaaza macrocyclic ring complex that is administered per kg body weight of the patient may be at least 0.1 mg/kg, such as at least 0.2 mg/kg. For example, the dose of the pentaaza macrocyclic ring complex that is administered per kg body weight of the patient may be at least 0.5 mg/kg. As another example, the dose of the pentaaza macrocyclic ring complex that is administered per kg body weight of the patient may be at least 1 mg/kg. In another example, the pentaaza macrocyclic ring complex that is administered per kg body weight may be at least 2 mg/kg, such as at least 3 mg/kg, and even at least about 15 mg/kg, such as at least 24 mg/kg and even at least 40 mg/kg. Generally, the dose of the pentaaza macrocyclic ring complex that is administered per kg body weight of the patient will not exceed 1000 mg/kg. For example the dose of the pentaaza macrocyclic ring complex that is administered per kg body weight of the patient may be in the range of from 0.1 to 1000 mg/kg, such as from 0.2 mg/kg to 40 mg/kg, such as 0.2 mg/kg to 24 mg/kg, and even 0.2 mg/kg to 10 mg/kg. As another example, the dose of the pentaaza macrocyclic ring complex that is administered per kg body weight may be in a range of from 1 mg/kg to 1000 mg/kg, such as from 3 mg/kg to 1000 mg/kg, and even from 5 mg/kg to 1000 mg/kg, such as 10 mg/kg to 1000 mg/kg. As another example, the dose of the pentaaza macrocyclic ring complex that is administered per kg body weight may be in a range of from 2 mg/kg to 15 mg/kg. As yet another example, the dose of the pentaaza macrocyclic ring complex that is administered per kg body weight may be in a range of from 3 mg/kg to 10 mg/kg. As another example, the dose of the pentaaza macrocyclic ring complex that is administered per kg body weight of the patient may be in the range of from 0.5 to 5 mg/kg. As yet a further example, the dose of the pentaaza macrocyclic ring complex that is administered per kg body weight of the patient may be in the range of from 1 to 5 mg/kg.

In one embodiment, the dosages and/or plasma concentrations discussed above may be particularly suitable for the pentaaza macrocyclic ring complex corresponding to GC4419, although they may also be suitable for other pentaaza macrocyclic ring complexes. In addition, one or ordinary skill in the art would recognize how to adjust the dosages and/or plasma concentrations based on factors such as the molecular weight and/or activity of the particular compound being used. For example, for a pentaaza macrocyclic ring complex having an activity twice that of GC4419, the dosage and/or plasma concentration may be halved, or for a pentaaza macrocyclic ring complex having a higher molecular weight that GC4419, a correspondingly higher dosage may be used.

The dosing schedule of the pentaaza macrocyclic ring complex can similarly be selected according to the intended treatment. For example, in one embodiment, a suitable dosing schedule can comprise dosing a patient at least once per week, such as at least 2, 3, 4, 5, 6 or 7 days per week (e.g., daily), during a course of treatment. As another example, in one embodiment, the dosing may be at least once a day (qd), or even at least twice a day (bid). In one embodiment, the course of treatment with the pentaaza macrocyclic ring complex may last at least as long as a course of treatment with one or more other agents, such as at least one of the thioredoxin reductase inhibitor and glutathione-depleting agent, and may even exceed the duration during which the at least one other agent is provided. The course of therapy with the pentaaza macrocyclic ring complex may also start on the same date as treatment with the other agent, such as on a same date as treatment with at least one of the thioredoxin reductase inhibitor and glutathione-depleting agent, or may start sometime after initial dosing with at least one of the other agents.

Thioredoxin Reductase Inhibitor

In one embodiment, the thioredoxin reductase inhibitor is a compound that inhibits thioredoxin reductase, the enzyme that catalyzes the reduction of thioredoxin. Thioredoxin can act as a reducing agent to reduce levels of reactive oxygen species, such as $H_2O_2$. Accordingly, the inhibition of thioredoxin reductase maintains thioredoxin in its reduced state, thereby decreasing the ability of thioredoxin to remove reactive oxygen species such as $H_2O_2$. In one embodiment, a thioredoxin reductase inhibitor selected for combination with the pentaaza macrocyclic ring complex is a compound that exhibits the thioredoxin reductase inhibition effect while also being therapeutically acceptable to the patient receiving the compound. For example, the thioredoxin reductase inhibitor may be at least one of auranofin, auro-thio-glucose, chloro(triethylphosphine)gold(I) (TEPAu), aurothiomalate, gold sodium thiomalate, sodium aurothiosulfate, gold acetate, 1,2,5-selenadiazole and derivatives thereof (e.g., as described in Liang et al, *Eur. J. Med. Chem.*, 84, 335-342 (2014)), metal complexes with 2-acetylpyridine-N(4)-ortho-chlorophenylthiosemicarbazone, such as palladium (II), platinum (II), bismuth (III), antimony (III) and gold (III) metal complexes (e.g., as described in Parillha et al, *Eur. J. Med. Chem.*, 84, 537-544 (2014)), and/or a pharmaceutically acceptable salt thereof. By way of further example, the thioredoxin reductase inhibitor may be at least one of auranofin (gold(+1)cation; 3,4,5-triacetyloxy-6-(acetyloxymethyl)oxane-2-thiolate; triethylphosphanium) and auro-thio-glucose gold(1) (2S,3S,4R,5S)-3,4,5-trihydroxy-6-(hydroxymethyl)-oxane-2-thiolate).

In one embodiment, a therapeutically effective amount of the thioredoxin reductase inhibitor, such as auranofin, may be an amount sufficient to provide a peak plasma concentration of at least 0.5 µM when administered to a patient. For example, in one embodiment, the thioredoxin reductase inhibitor, such as auranofin, may be administered in an amount sufficient to provide a peak plasma concentration of at least 0.8 µM when administered to a patient. In yet another embodiment, the thioredoxin reductase inhibitor, such as auranofin, may be administered in an amount sufficient to provide a peak plasma concentration of at least 1 µM when administered to a patient. Generally, the thioredoxin reductase inhibitor, such as auranofin, will not be administered in an amount that would provide a peak plasma concentration greater than 8 µM when administered to a patient, and may even provide a peak plasma concentration of less than 5 µM, and even less than 2 µM. For example, the thioredoxin reductase inhibitor, such as auranofin, may be administered in an amount sufficient to provide a peak plasma concentration in the range of from 0.5 µM to 5 µM in a patient, such as in a range of from 0.5 µM to 2 µM. In yet another embodiment, a thioredoxin reductase inhibitor, such as auranofin, may be administered in an amount sufficient to provide a peak plasma concentration in the range of from 2.5 µM to 3.5 µM.

In yet another embodiment, a dose of the thioredoxin reductase inhibitor, such as auranofin, that is administered per kg body weight of the patient may be at least 0.05 mg/kg, such as at least 0.1 mg/kg, and even at least 0.2 mg/kg. For example, the dose of the thioredoxin reductase inhibitor, such as auranofin, that is administered per kg body weight of the patient may be at least 0.5 mg/kg. As another example, the dose of the thioredoxin reductase inhibitor, such as auranofin, that is administered per kg body weight of the patient may be at least 1 mg/kg. In another example, the thioredoxin reductase inhibitor, such as auranofin, that is administered per kg body weight may be at least 1.5 mg/kg, such as at least 3 mg/kg, and even at least about 5 mg/kg. Generally, the dose of the thioredoxin reductase inhibitor, such as auranofin that is administered per kg body weight of the patient will not exceed 300 mg/kg. For example the dose of the thioredoxin reductase inhibitor, such as auranofin, that is administered per kg body weight of the patient may be in the range of from 0.1 to 300 mg/kg, such as from 0.2 mg/kg to 40 mg/kg, and even from 1 mg/kg to 5 mg/kg.

Furthermore, it is noted that the dosage of the thioredoxin reductase inhibitor may vary according to the particular inhibitor selected, as well as according to the route of administration, etc. For example, for thioredoxin reductase inhibitors having high potency, a lower dosage may be used to provide the same treatment effect, as compared to thioredoxin reductase inhibitors having less potency. Accordingly, while exemplary dosage ranges for the particular thioredoxin reductase inhibitor auranofin are being provided herein, the exemplary ranges are not limiting, and auranofin and/or other thioredoxin reductase inhibitors may be provided in different dosages, administration routes, or administration frequencies, other than those specifically exemplified herein, according to the particular thioredoxin reductase inhibitor to be administered and the therapeutic effect to be achieved.

The dosing schedule of the thioredoxin reductase inhibitor, such as auranofin, can similarly be selected according to the intended treatment. For example, in one embodiment, a suitable dosing schedule can comprise dosing a patient at least once per week, such as at least 2, 3, 4, 5, 6 or 7 days per week (e.g., daily), during a course of treatment. As another example, in one embodiment, the dosing may be at least once a day (qd), or even at least twice a day (bid). In one embodiment, the course of treatment with the thioredoxin reductase inhibitor, such as auranofin, may last at least as long as a course of treatment with one or more other agents, such as least one of the pentaaza macrocyclic ring complex and glutathione-depleting agent, and may even exceed the duration during which the at least one other agent is provided. The course of therapy with the thioredoxin reductase inhibitor, such as auranofin, may also start on the same date as treatment with the other agent, such as on a same date as treatment with at least one of the pentaaza macrocyclic ring complex and glutathione-depleting agent, or may start sometime after initial dosing with at least one of the other agents.

Glutathione Depleting Agent

In one embodiment, the glutathione depleting agent is an agent that decreases levels of glutathione in the cancerous cells. The glutathione depleting agent may be a compound that acts to deplete glutathione by any of a number of different mechanisms. For example, in one embodiment, the glutathione depleting agent is a glutathione synthesis inhibitor, such as buthionine sulfoximine. In another embodiment, the glutathione depleting agent is an inhibitor of $x_c^-$ cysteine/glutamate antiporter, such as sulfasalazine. In yet another embodiment, the glutathione depleting agent is a glutathione reductase inhibitor, such as 2-acetylamino-3-[4-(2-acetylamino-2-carboxyethylsulfanylthiocarbonyamino) phenylthiocarbamolylsulfanyl] propionic acid (2-AAPA). In one embodiment, the glutathione depleting agent can comprise at least one of buthionine sulfoximine, sulfasalazine, piperlongumine, N-ethylmaleimide, N-pyrenylmaleimide, 2-AAPA, erastin, sorafenib, 1S,3R-RSL3, DPI19, DPI18, DPI17, DPI13, DPI12, DPI10 (ML210), DPI7(ML162) (Cao et al., *Cell Mol. Life Sci.*, (2016)), and altretamine, and/or pharmaceutically acceptable salts thereof. Structures of some of these suitable glutathione depleting agents are as follows:

-continued
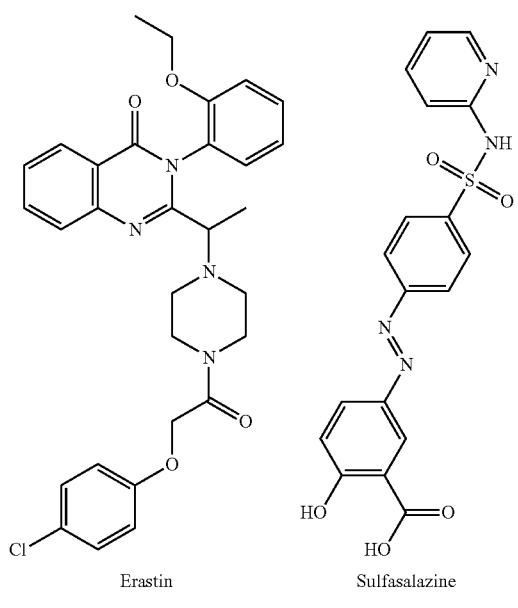
Erastin
Sulfasalazine
Soralenib
1S,3R-RSL3
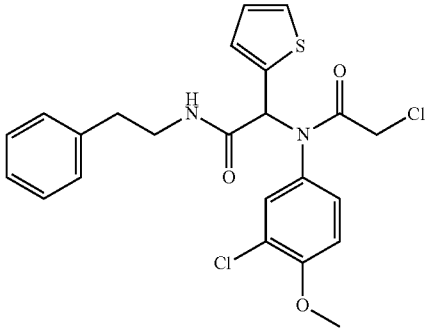
ML162 (DPI7)
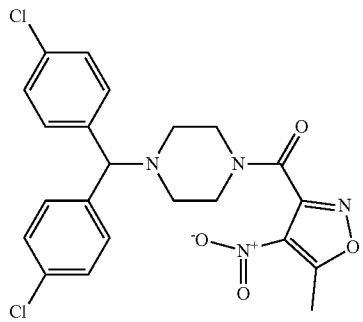
ML210 (DPI10)
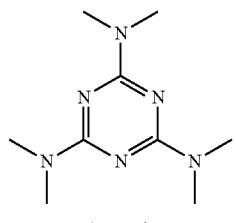
Altretamine
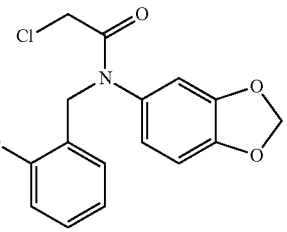
DPI13 = N-[2-(allyloxy)benzyl]-N-1,3-benzodioxol-5-yl-2-chloroacetamide
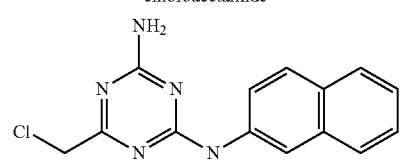
DPI17 = 6-(chloromethyl)-N-(2-naphthyl)-1,3,5-triazine-2,4-diamine
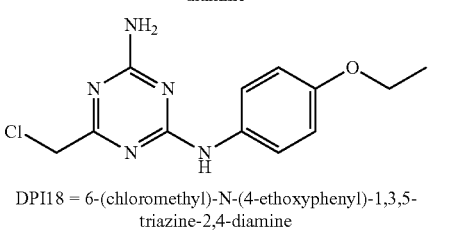
DPI18 = 6-(chloromethyl)-N-(4-ethoxyphenyl)-1,3,5-triazine-2,4-diamine
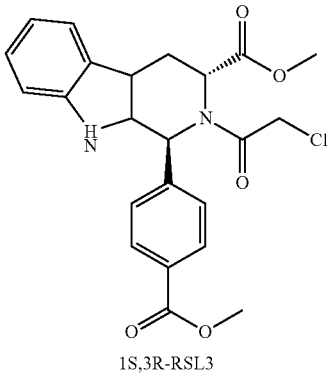

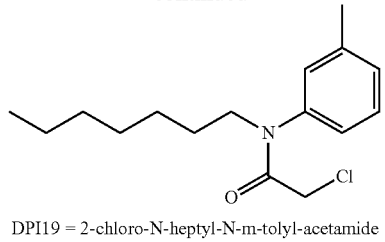

DPI19 = 2-chloro-N-heptyl-N-m-tolyl-acetamide

In one embodiment, the glutathione depleting agent comprises at least one of buthionine sulfoximine (BSO) and sulfasalazine, and/or a pharmaceutically acceptable salt thereof.

In one embodiment, a therapeutically effective amount of the glutathione-depleting agent, such as sulfasalazine, may be an amount sufficient to provide a peak plasma concentration of at least 200 µM when administered to a patient. For example, in one embodiment, the glutathione-depleting agent, such as sulfasalazine, may be administered in an amount sufficient to provide a peak plasma concentration of at least 250 µM when administered to a patient. In yet another embodiment, the glutathione-depleting agent, sulfasalazine, may be administered in an amount sufficient to provide a peak plasma concentration of at least 300 µM when administered to a patient. Generally, the glutathione-depleting agent, such as sulfasalazine, will not be administered in an amount that would provide a peak plasma concentration greater than 600 µM when administered to a patient. For example, the glutathione-depleting agent, such as sulfasalazine, may be administered in an amount sufficient to provide a peak plasma concentration in the range of from 200 µM to 600 µM in a patient.

In yet another embodiment, a dose of the glutathione-depleting agent, such as sulfasalazine, that is administered per kg body weight of the patient (e.g., administered intravenously) may be at least 3 mg/kg, such as at least 5 mg/kg, and even at least 8 mg/kg. Generally, the dose of the glutathione-depleting agent, such as sulfasalazine, that is administered per kg body weight of the patient will not exceed 40 mg/kg. For example the dose of the glutathione-depleting agent, such sulfasalazine, that is administered per kg body weight of the patient may be in the range of from 3 mg/kg to 40 mg/kg, such as from 4 mg/kg to 10 mg/kg.

In one embodiment, a therapeutically effective amount of the glutathione-depleting agent, such as BSO, may be an amount sufficient to provide a peak plasma concentration of at least 100 µM when administered to a patient. For example, in one embodiment, the glutathione-depleting agent, such as BSO, may be administered in an amount sufficient to provide a peak plasma concentration of at least 200 µM when administered to a patient. In yet another embodiment, the glutathione-depleting agent, such as BSO, may be administered in an amount sufficient to provide a peak plasma concentration of at least 250 µM when administered to a patient. Generally, the glutathione-depleting agent, such as BSO, will not be administered in an amount that would provide a peak plasma concentration greater than 9000 µM when administered to a patient, and may even provide a peak plasma concentration equal to or less than 1000 µM in a patient. For example, the glutathione-depleting agent, such as BSO, may be administered in an amount sufficient to provide a peak plasma concentration in the range of from 100 µM to 1000 µM in a patient.

In yet another embodiment, a dose of the glutathione-depleting agent, such as BSO, that is administered per $m^2$ of the patient (e.g., administered intravenously) may be at least 8 g/$m^2$, such as at least 10 g/$m^2$, and even at least 13 g/$m^2$. Generally, the dose of the glutathione-depleting agent, such as BSO, that is administered per $m^2$ of the patient will not exceed 40 g/$m^2$. For example the dose of the glutathione-depleting agent, such as BSO, that is administered per $m^2$ of the patient may be in the range of from 8 g/$m^2$ to 40 g/$m^2$, such as from 10 g/$m^2$ to 17 g/$m^2$.

Furthermore, it is noted that the dosage of the glutathione-depleting agent may vary according to the particular agent selected, as well as according to the route of administration, etc. For example, for glutathione-depleting agents having high potency, a lower dosage may be used to provide the same treatment effect, as compared to glutathione-depleting agents having less potency. Accordingly, while exemplary dosage ranges for the particular glutathione-depleting agents BSO and sulfasalazine are being provided herein, the exemplary ranges are not limiting, and BSO, sulfasalazine and/or other glutathione-depleting agents may be provided in different dosages, administration routes, or administration frequencies, other than those specifically exemplified herein, according to the particular glutathione-depleting agent to be administered and the therapeutic effect to be achieved.

The dosing schedule of the glutathione-depleting agent, such as BSO or sulfasalazine, can similarly be selected according to the intended treatment. For example, in one embodiment, a suitable dosing schedule can comprise dosing a patient at least once per week, such as at least 2, 3, 4, 5, 6 or 7 days per week (e.g., daily), during a course of treatment. As another example, in one embodiment, the dosing may be at least once a day (qd), or even at least twice a day (bid). In one embodiment, the course of treatment with the glutathione-depleting agent, such as BSO or sulfasalazine, may last at least as long as a course of treatment with one or more other agents, such as least one of the pentaaza macrocyclic ring complex and thioredoxin reductase inhibitor agent, and may even exceed the duration during which the at least one other agent is provided. The course of therapy with the glutathione-depleting agent, such as BSO or sulfasalazine, may also start on the same date as treatment with the other agent, such as on a same date as treatment with at least one of the pentaaza macrocyclic ring complex and thioredoxin reductase inhibitor, or may start sometime after initial dosing with at least one of the other agents.

Methods of Administration

According to one embodiment, the at least one active agent that is at least one of a thioredoxin reductase inhibitor and a glutathione depleting agent, is administered as a co-therapy or combination therapy with the pentaaza macrocyclic ring complex. Co-therapy or combination therapy according to the methods described herein is intended to embrace administration of each compound in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent, or single or multiple parenteral administrations, or other routes of administration and dosage forms. When administered in combination, therefore, the therapeutic agents (i.e., the pentaaza macrocyclic ring complex, the thioredoxin reductase inhibitor, and/or the glutathione-depleting agent) can be formulated as separate compositions that are administered at the same time or sequentially at different times, or the therapeutic agents can be given as a single composition. Pharmaceutical compositions and formulations are discussed elsewhere herein. Furthermore, while the at least one "active agent" is referred to herein as being at least one of the thioredoxin reductase inhibitor and glutathione depleting agent, it is noted that all combinations of these are also explicitly included herein, including administration of thioredoxin reductase inhibitor without a glutathione depleting agent, administration of a glutathione-depleting agent without a thioredoxin reductase inhibitor, and administration of both a thioredoxin reductase inhibitor and a glutathione-depleting agent.

It is not necessary that the pentaaza macrocyclic ring complex, thioredoxin reductase inhibitor, and/or glutathione-depleting agent, be administered simultaneously or essentially simultaneously; the agents and compounds may be administered in sequence. The advantage of a simultaneous or essentially simultaneous administration, or sequential administration, is well within the determination of the skilled clinician. For instance, while a pharmaceutical composition or formulation comprising a pentaaza macrocyclic ring complex may be advantageous for administering first in the combination for one particular treatment, prior administration of the thioredoxin reductase inhibitor and/or glutathione depleting agent(s) (or prior administration of the pentaaza macrocyclic ring complex) may be advantageous in another treatment. It is also understood that the instant combination of pentaaza macrocyclic ring complex, thioredoxin reductase inhibitor, and glutathione depleting agent may be used in conjunction with other methods of treating cancer (typically cancerous tumors) including, but not limited to, radiation therapy and surgery, or other chemotherapy. It is further understood that a cytostatic or quiescent agent, or antiemetic agent, or hematopoietic growth factor, if any, may be administered sequentially or simultaneously with any or all of the other synergistic therapies.

Thus, embodiment of the therapeutic method include wherein a pentaaza macrocyclic ring complex and at least one active agent selected from thioredoxin reductase inhibitor, glutathione-depleting agent, and combinations thereof, are administered simultaneously or sequentially. For instance, the present disclosure encompasses a method for the treatment of cancer wherein a pentaaza macrocyclic ring complex and a thioredoxin reductase inhibitor are administered simultaneously or sequentially. By way of another example, the present disclosure encompasses a method for the treatment of cancer wherein a pentaaza macrocyclic ring complex and a glutathione depleting agent are administered simultaneously or sequentially. Further, the present disclosure encompasses a method for the treatment of cancer wherein a pentaaza macrocyclic ring complex, a thioredoxin reductase inhibitor, and a glutathione inhibiting agent are administered simultaneously or sequentially.

As noted above, if the pentaaza macrocyclic ring complex, thioredoxin reductase inhibitor, and glutathione depleting agent are not administered simultaneously or essentially simultaneously, then the initial order of administration of the components may be varied.

Thus, for example, a pentaaza macrocyclic ring complex may be administered first, followed by the administration of a thioredoxin reductase inhibitor; or a thioredoxin reductase may be administered first, followed by the administration of a pentaaza macrocyclic ring complex. Similarly, a pentaaza macrocyclic ring complex may be administered first, followed by the administration of a glutathione depleting agent; or a glutathione depleting agent may be administered first, followed by the administration of a pentaaza macrocyclic ring complex. Where a pentaaza macrocyclic ring complex, a thioredoxin reductase inhibitor, and a glutathione-depleting agent are administered in sequence, the sequence may vary accordingly. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. By way of another example, at least one of the thioredoxin reductase inhibitor and/or glutathione depleting agent may be administered initially (e.g., to decrease hydrogen peroxide metabolism). The treatment is then continued with the administration of the pentaaza macrocyclic ring complex (e.g., to produce new to hydrogen peroxide from superoxide), until the treatment protocol is complete. Other sequences of administration to exploit the effects described herein are contemplated.

In one embodiment, the subject is pre-treated with the pentaaza macrocyclic ring complex (i.e., the pentaaza macrocyclic ring complex is pre-administered), followed by administration of at least one of the other active agents (i.e., the thioredoxin reductase inhibitor and/or the glutathione depleting agent), or vice versa. In accordance with such embodiments, the other active agents is/are preferably administered at least 1 hour, but no more than 3 days, after administration of the pentaaza macrocyclic ring complex, or vice versa. For example, in one embodiment, the other active agents is/are administered between 1 hour and 2 days after administration of the pentaaza macrocyclic ring complex, or vice versa. In another embodiment, for example, the other active agents is/are administered between 1 hour and 1 day after administration of the pentaaza macrocyclic ring complex, or vice versa. For example, the other active agent may be administered within 1 hour, 2 hours, 3 hours, 4 hours, 5 hours, 6 hours, 12 hours, 18 hours, 24 hours, 36 hours, or 48 hours after administration of the pentaaza macrocyclic ring complex, or vice versa. In one particular embodiment, for example, the active agents is/are administered within 24 hours after administration of the pentaaza macrocyclic ring complex, or vice versa. In these and other embodiments, the pentaaza macrocyclic ring complex may be administered in multiple doses leading up to administration of the other active agent.

Alternatively, the subject may be pre-treated with the active agents (i.e., the thioredoxin reductase inhibitor(s) and/or the glutathione depleting agent(s)), followed by administration of the pentaaza macrocyclic ring complex, or vice versa. In accordance with such embodiments, the pentaaza macrocyclic ring complex is preferably administered within at least 1 plasma half-life of the other active agents, but no more than 4 plasma half-lives of the other active agents, or vice versa. For example, the pentaaza macrocyclic ring complex may be administered within 1, 2, or 3 plasma half-lives of the other active agents, or vice versa.

In other alternative embodiments, the subject may be pre-treated with the pentaaza macrocyclic ring complex, followed by administration of at least one of the other active agent, which is further followed by an additional administration of the pentaaza macrocyclic ring complex. In accordance with this embodiment, for example, the standard pentaaza macrocyclic ring complex dose may be separated into two (or more) portions, one portion of which is administered prior to administration of the other active agent, and the second portion of which is administered after administration of the other active agent. This staggered therapy regime could also be employed where the active agents is/are administered first. In addition, the subject could be pre-treated with a partial or full dose of pentaaza macrocyclic ring complex, followed by administration of a first active agent (e.g., one of the thioredoxin reductase inhibitor), which is then followed by the administration of additional (or partial) dose of pentaaza macrocyclic ring complex, which may be further followed by administration of a second active agent (e.g., the other of the thioredoxin reductase inhibitor and glutathione depleting agent).

As described in further detail below, the combinations of the disclosure may also be co-administered with other well known therapeutic agents that are selected for their particular usefulness against the condition that is being treated. Combinations may alternatively be used sequentially with known pharmaceutically acceptable agent(s) when a multiple combination formulation is inappropriate.

The pentaaza macrocyclic ring complex, thioredoxin reductase inhibitor, and glutathione depleting agent are generally administered according to therapeutic protocols well known in the art. It will be apparent to those skilled in the art that the administration of the various components can be varied depending on the disease being treated and the known effects of pentaaza macrocyclic ring complex, thioredoxin reductase inhibitor, and/or glutathione depleting agent on that disease. Also, in accordance with the knowledge of the skilled clinician, the therapeutic protocols (e.g., dosage amounts and times of administration) can be varied in view of the observed effects of the administered therapeutic agents (i.e., pentaaza macrocyclic ring complex, thioredoxin reductase inhibitor, and glutathione depleting agent) on the patient, and in view of the observed responses of the disease to the administered therapeutic agents.

Also, in general, pentaaza macrocyclic ring complex, thioredoxin reductase inhibitor, and/or glutathione depleting agent do not have to be administered in the same pharmaceutical composition, and may, because of different physical and chemical characteristics, have to be administered by different routes. For example, the pentaaza macrocyclic ring complex may be administered orally to generate and maintain good blood levels thereof, while the thioredoxin reductase inhibitor and/or glutathione depleting agent may be administered intravenously, or vice versa. The determination of the mode of administration and the advisability of administration, where possible, in the same pharmaceutical composition, or in separate pharmaceutical compositions (e.g., two or three separate compositions) is well within the knowledge of the skilled clinician. The initial administration can be made according to established protocols known in the art, and then, based upon the observed effects, the dosage, modes of administration and times of administration can be modified by the skilled clinician.

The particular choice of pentaaza macrocyclic ring complex, thioredoxin reductase inhibitor, and glutathione depleting agent (each of which are described in detail herein), and other related therapies (such as chemotherapy or radiation), will depend upon the diagnosis of the attending physicians and their judgment of the condition of the patient and the appropriate treatment protocol.

Thus, in accordance with experience and knowledge, the practicing physician can modify each protocol for the administration of a component (pentaaza macrocyclic ring complex, thioredoxin reductase inhibitor, and/or glutathione depleting agent) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The products of which the combination are composed may be administered simultaneously, separately or spaced out over a period of time so as to obtain the maximum efficacy of the combination; it being possible for each administration to vary in its duration from a rapid administration to a relatively continuous perfusion of either component (in separate formulations or in a single formulation). As a result, for the purposes of the present disclosure, the combinations are not exclusively limited to those which are obtained by physical association of the constituents, but also to those which permit a separate administration, which can be simultaneous or spaced out over a period of time.

Accordingly, administration of the components described herein can occur as a single event or over a time course of treatment. For example, one or more of the pentaaza macrocyclic ring complex, thioredoxin reductase inhibitor, and/or glutathione depleting agent can be administered (simultaneously or in sequence) hourly (e.g., every hour, every two hours, every three hours, every four hours, every five hours, every six hours, and so on), daily, weekly, bi-weekly, or monthly. For treatment of acute conditions, the time course of treatment may be at least several hours or days. Certain conditions could extend treatment from several days to several weeks. For example, treatment could extend over one week, two weeks, or three weeks. For more chronic conditions, treatment could extend from several weeks to several months, a year or more, or the lifetime of the patient in need of such treatment. Alternatively, the compounds and agents can be administered hourly, daily, weekly, bi-weekly, or monthly, for a period of several weeks, months, years, or over the lifetime of the patient as a prophylactic measure.

The dose or amount of pharmaceutical compositions including the pentaaza macrocyclic ring complex, thioredoxin reductase inhibitor, and/or glutathione depleting agent administered to the patient should be an effective amount for the intended purpose, i.e., treatment or prophylaxis of one or more of the diseases, pathological disorders, and medical conditions discussed herein, particularly cancer. Generally speaking, the effective amount of the composition administered can vary according to a variety of factors such as, for example, the age, weight, sex, diet, route of administration, and the medical condition of the patient in need of the treatment. Specifically preferred doses are discussed more fully below. It will be understood, however, that the total daily usage of the compositions described herein will be decided by the attending physician or veterinarian within the scope of sound medical judgment.

As noted above, the combinations can be co-administered (via a co-formulated dosage form or in separate dosage forms administered at about the same time). The combinations can also be administered separately, at different times, with each agent in a separate unit dosage form. Numerous approaches for administering anti-cancer drugs and pentaaza macrocyclic ring complex are known in the art, and can readily be adapted for use in the present disclosure. The pharmaceutical compositions may be delivered orally, e.g., in a tablet or capsule unit dosage form, or parenterally, e.g., in an injectable unit dosage form, or by some other route.

For systemic administration, for example, the drugs can be administered by, for example, intravenous infusion (continuous or bolus). The compositions can be used for any therapeutic or prophylactic treatment where the patient benefits from treatment with the combination.

The specific therapeutically effective dose level for any particular patient will depend upon a variety of factors including the disorder being treated and the severity of the disorder; activity of the specific compound(s) employed; the age, body weight, general health, sex and diet of the patient; the time of administration; the route of administration; the rate of excretion of the specific compound(s) employed; the duration of the treatment; drugs used in combination or coincidental with the specific compound(s) employed and like factors well known in the medical and/or veterinary arts. For example, it is well within the skill of the art to start doses of the compound(s) at levels lower than those required to achieve the desired therapeutic effect and to gradually increase the dosage until the desired effect is achieved. If desired, the effective daily doses may be divided into multiple doses for purposes of administration. Consequently, single dose compositions may contain such amounts or submultiples to make up the daily dose.

Suitable or preferred doses for each of the components employed in the methods or included in the compositions described herein are generally known in the art. Preferred dosages for the pentaaza macrocyclic ring complex, for instance, may be within the range of 10 to 500 mg per patient per day. A typical dose of auranofin, a thioredoxin reductase inhibitor, can be a dose that results in blood levels of 0.5 µM to 5 µM, such as 0.5 µM to 2 µM. For buthionine sulfoximine, a glutathione-depleting agent, a suitable dose range may be one that provides a blood level of 100 µM to 9000 µM, such as from 100 µM to 1000 µM. For sulfasalazine, a glutathione-depleting agent, a suitable dose range may be one that provides a blood level of 200 µM to 600 µM. However, the dosage may vary depending on the dosing schedule, which can be adjusted as necessary to achieve the desired therapeutic effect. It should be noted that the ranges of effective doses provided herein are not intended to limit the disclosure and represent exemplary dose ranges. The most preferred dosage will be tailored to the individual subject, taking into account, among other things, the particular combinations employed, and the patient's age, sex, weight, physical condition, diet, etc., as is understood and determinable by one of ordinary skill in the art without undue experimentation.

Treatment of cancer, or cancer therapies, described herein includes achieving a therapeutic benefit and/or a prophylactic benefit. Therapeutic benefits generally refer to at least a partial eradication or amelioration of the underlying disorder being treated. For example, in a cancer patient, therapeutic benefit includes (partial or complete) eradication or amelioration of the underlying cancer. Also, a therapeutic benefit is achieved with at least partial, or complete, eradication or amelioration of one or more of the physiological symptoms associated with the underlying disorder such that an improvement is observed in the patient, notwithstanding the fact that the patient may still be afflicted with the underlying disorder. For prophylactic benefit, a method of the disclosure may be performed on, or a composition of the invention administered to, a patient at risk of developing cancer, or to a patient reporting one or more of the physiological symptoms of such conditions, even though a diagnosis of the condition may not have been made.

Other Cancer Therapies

In one embodiment, the treatment provided herein can further comprise treatment with another therapy other than those specifically described above, such as for example a radiation therapy, a chemotherapy, or other treatment. For example, in one embodiment, one or more of radiation therapy and chemotherapy is administered to the subject prior to, concomitantly with, or after administration of one or more of at least one of the thioredoxin reductase inhibitor and glutathione-depleting agent, and the pentaaza macrocyclic ring complex. Further detailed description of radiation therapies and chemotherapies suitable for the treatment of cancer are provided below.

In one embodiment, one or more of radiation therapy and chemotherapy can be administered concomitantly with administration of at least one of the thioredoxin reductase inhibitor and glutathione-depleting agent, and pentaaza macrocyclic ring complex. For example, one or more of the agent(s) and pentaaza macrocyclic ring complexes may be administered during a course of radiation therapy and/or chemotherapy, such as in between, before or after, or on the same day as dosing with radiation and/or chemotherapy.

In yet another embodiment, the combination therapy of the pentaaza macrocyclic ring complex and agents(s) (e.g. thioredoxin reductase inhibitor, glutathione-depleting agent), can be administered in the absence of any other cancer treatment. As demonstrated further in the examples below, it has been unexpectedly discovered that the pentaaza macrocyclic ring complexes exhibit synergistic results when combined with at least one of the thioredoxin reductase inhibitor and glutathione-depleting agent, even when administered without radiation therapy or chemotherapy. Accordingly, in one embodiment, the cancer treatment provided to the subject may consist essentially of the pentaaza macrocyclic ring complex and one or more of the agents, without the administration of a chemotherapeutic agent or radiation exposure (i.e. without administering a radiation dose or dose fraction). For example, the combination of the pentaaza macrocyclic ring complex and at least one agent may be administered to a subject that is not receiving radiation therapy, and/or that is not receiving chemotherapy. In one embodiment, the treatment comprises administering the pentaaza macrocyclic ring complex to a subject that is not receiving radiation therapy. In yet another embodiment, the treatment comprises administering both (i) at least one of the agents, and (ii) the pentaaza macrocyclic ring complex, to a subject that is not receiving radiation therapy. In yet another embodiment, where a course of therapy comprises administration of the pentaaza macrocyclic ring complex and at least one of the agents (e.g., thioredoxin reductase inhibitor, glutathione-depleting agent), they are administered to a subject that does not receive radiation therapy during the course of therapy.

In one embodiment, the subject receiving the combination of pentaaza macrocyclic ring complex and the at least one agent (e.g. thioredoxin reductase inhibitor, glutathione-depleting agent), may be one that has not been exposed to radiation (i.e., received a dose or dose fraction of radiation) and/or has not received a dose of chemotherapeutic agent for at least one day, such as at least one week, and even at least one month, and even at least 6 months, and/or that has not ever received such treatment at all before initial treatment with one or more of the pentaaza macrocyclic ring complex and agent(s) (e.g., thioredoxin reductase inhibitor, glutathione-depleting agent). In yet another embodiment, any radiation therapy and/or chemotherapy that is administered to the subject after the combination treatment with the pentaaza macrocyclic ring complex and agent(s) (e.g., thioredoxin reductase inhibitor, glutathione-depleting agent) is delayed by at least one day, such as at least one week, and even at least one month, such as at least 6 months, after a final dose of one or more of the pentaaza macrocyclic ring complex and agent(s) provided during the course of the combination therapy treatment. That is, the combination therapy of the pentaaza macrocyclic ring complex and agent(s) (e.g., thioredoxin reductase inhibitor, glutathione-depleting agent) can be administered to a subject that has never before received radiation therapy and/or chemotherapy, or that has received such therapy only in the distant past. Furthermore, the combination therapy of the pentaaza macrocyclic ring complex and agent(s) (e.g., thioredoxin reductase inhibitor, glutathione-depleting agent) can be administered to provide a course of treatment that does not include any exposure to radiation or doses of chemotherapeutic agent. As yet a further embodiment, the combination therapy of the pentaaza macrocyclic ring complex and agent(s) (e.g., thioredoxin reductase inhibitor, glutathione-depleting agent) can be provided to form a course of treatment substantially without performing any radiation therapy or chemotherapy after the course of treatment, or with such radiation or chemotherapeutic treatment being performed only after a significant period of time has elapsed after the course of combination treatment has ended. In one embodiment, the treatment comprises administering one or more of the pentaaza macrocyclic ring complex agent(s) (e.g., thioredoxin reductase inhibitor, glutathione-depleting agent) to the subject on a day other than a day that the subject is receiving radiation therapy.

Cancer Treatment Methods

In general, any subject having, or suspected of having, a cancer or other proliferative disorder may be treated using the compositions and methods of the present disclosure. Subjects receiving treatment according to the methods described herein are mammalian subjects, and typically human patients. Other mammals that may be treated according to the present disclosure include companion animals such as dogs and cats, farm animals such as cows, horses, and swine, as well as birds and more exotic animals (e.g., those found in zoos or nature preserves). In one embodiment of the disclosure, a method is provided for the treatment of cancerous tumors, particularly solid tumors. Advantageously, the methods described herein may reduce the development of tumors, reduce tumor burden, or produce tumor regression in a mammalian host. Cancer patients and individuals desiring cancer prophylaxis can be treated with the combinations described herein.

Cancer and tumors generally refer to or describe the physiological condition in mammals that is typically characterized by unregulated cell growth. By means of the pharmaceutical combinations, co-formulations, and combination therapies of the present disclosure, various tumors can be treated such as tumors of the breast, heart, lung, small intestine, colon, spleen, kidney, bladder, head and neck, ovary, prostate, brain, pancreas, skin, bone, bone marrow, blood, thymus, uterus, testicles, cervix, and liver.

In one embodiment, the tumor or cancer is chosen from adenoma, angio-sarcoma, astrocytoma, epithelial carcinoma, germinoma, glioblastoma, glioma, hamartoma, hemangioendothelioma, hemangiosarcoma, hematoma, hepato-blastoma, leukemia, lymphoma, medulloblastoma, melanoma, neuroblastoma, osteosarcoma, retinoblastoma, rhabdomyosarcoma, sarcoma, and teratoma. The tumor can be chosen from acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic, papillary serous adeno-carcinoma, pineal cell, pituitary tumors, plasmacytoma, pseudo-sarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.

Thus, for example, the present disclosure provides methods for the treatment of a variety of cancers, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

For example, particular leukemias that can be treated with the combinations and methods described herein include, but are not limited to, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Lymphomas can also be treated with the combinations and methods described herein. Lymphomas are generally neoplastic transformations of cells that reside primarily in lymphoid tissue. Lymphomas are tumors of the immune system and generally are present as both T cell- and as B cell-associated disease. Among lymphomas, there are two major distinct groups: non-Hodgkin's lymphoma (NHL) and Hodgkin's disease. Bone marrow, lymph nodes, spleen and circulating cells, among others, may be involved. Treatment protocols include removal of bone marrow from the patient and purging it of tumor cells, often using antibodies directed against antigens present on the tumor cell type, followed by storage. The patient is then given a toxic dose of radiation or chemotherapy and the purged bone marrow is then re-infused in order to repopulate the patient's hematopoietic system.

Other hematological malignancies that can be treated with the combinations and methods described herein include myelodysplastic syndromes (MDS), myeloproliferative syndromes (MPS) and myelomas, such as solitary myeloma and multiple myeloma. Multiple myeloma (also called plasma cell myeloma) involves the skeletal system and is characterized by multiple tumorous masses of neoplastic plasma cells scattered throughout that system. It may also spread to lymph nodes and other sites such as the skin. Solitary myeloma involves solitary lesions that tend to occur in the same locations as multiple myeloma.

In one embodiment, the methods and pharmaceutical compositions described herein are used to treat a cancer that is any of breast cancer, melanoma, oral squamous cell carcinoma, lung cancer including non-small cell lung cancer, renal cell carcinoma, colorectal cancer, prostate cancer, brain cancer, spindle cell carcinoma, urothelial cancer, bladder cancer, colorectal cancer, head and neck cancers such as squamous cell carcinoma, and pancreatic cancer. In one embodiment, the methods and pharmaceutical compositions described herein are used to treat a cancer that is any of breast cancer, lung cancer including non-small cell lung cancer, renal cell carcinoma, spindle cell carcinoma, colorectal cancer, head and neck squamous cell carcinoma, pancreatic cancer. In yet another embodiment, the methods and pharmaceutical compositions described herein are used to treat a cancer that is any of head and neck cancer and lung cancer. In yet another embodiment, the methods and pharmaceutical compositions described herein are used to treat a cancer that is any of breast cancer and lung cancer.

Pharmaceutical Formulations

Another aspect of the present disclosure relates to the pharmaceutical compositions comprising the combinations described herein, together with a pharmaceutically acceptable excipient. The pharmaceutical compositions include the pentaaza macrocyclic ring complex (e.g., those corresponding to Formula (I)), and at least one active agent selected from a thioredoxin reductase inhibitor, a glutathione depleting agent, and combinations thereof, as discussed above, typically formulated as a pharmaceutical dosage form, optionally in combination with a pharmaceutically acceptable carrier, additive or excipient. In one embodiment, for example, the pharmaceutical composition comprises a pentaaza macrocyclic ring complex, a thioredoxin reductase inhibitor, and a pharmaceutically acceptable excipient. In another embodiment, the pharmaceutical composition comprises a pentaaza macrocyclic ring complex, a glutathione depleting agent, and a pharmaceutically acceptable excipient. In yet another embodiment, the pharmaceutical composition comprises a pentaaza macrocyclic ring complex, a thioredoxin reductase inhibitor, a glutathione depleting agent, and a pharmaceutically acceptable excipient. Pharmaceutical compositions according to the present disclosure may be used in the treatment of cancer.

The pharmaceutical compositions described herein can comprise products that result from the mixing or combining of more than one active ingredients, and includes both fixed and non-fixed combinations of the active ingredients. Fixed combinations are those in which the active ingredients, e.g., a pentaaza macrocyclic ring complex, a thioredoxin reductase inhibitor, and/or a glutathione depleting agent described herein, are both administered to a patient simultaneously in the form of a single entity or dosage. Non-fixed combinations are those in which the active ingredients, e.g., a pentaaza macrocyclic ring complex, a thioredoxin reductase inhibitor, and/or a glutathione depleting agent described herein, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

The above-described a pentaaza macrocyclic ring complex, a thioredoxin reductase inhibitor, and/or a glutathione depleting agent may be dispersed in a pharmaceutically acceptable carrier prior to administration to the mammal; i.e., the components described herein are preferably co-formulated. The carrier, also known in the art as an excipient, vehicle, auxiliary, adjuvant, or diluent, is typically a substance which is pharmaceutically inert, confers a suitable consistency or form to the composition, and does not diminish the efficacy of the compound. The carrier is generally considered to be "pharmaceutically or pharmacologically acceptable" if it does not produce an unacceptably adverse, allergic or other untoward reaction when administered to a mammal, especially a human.

The selection of a pharmaceutically acceptable carrier will also, in part, be a function of the route of administration. In general, the compositions of the described herein can be formulated for any route of administration so long as the blood circulation system is available via that route, and in accordance with the conventional route of administration of the component (e.g., a pentaaza macrocyclic ring complex, a thioredoxin reductase inhibitor, and/or a glutathione depleting agent). For example, suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in combination with the compositions of the present disclosure are well known to those of ordinary skill in the art and are selected based upon a number of factors: the particular compound(s)

and agent(s) used, and its/their concentration, stability and intended bioavailability; the subject, its age, size and general condition; and the route of administration. Suitable non-aqueous, pharmaceutically-acceptable polar solvents include, but are not limited to, alcohols (e.g., a-glycerol formal, 6-glycerol formal, 1,3-butyleneglycol, aliphatic or aromatic alcohols having 2 to 30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(6-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di-, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di-, or tri-glycerides, fatty acid esters such as isopropyl myristrate, fatty acid derived PEG esters such as PEG-hydroxyoleate and PEG-hydroxystearate, N-methyl pyrrolidinone, pluronic 60, polyoxyethylene sorbitol oleic polyester, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, DE, polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $0_4$ to $0_{22}$ fatty acid(s) (e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2 to 30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3 to 30 carbon atoms (e.g., acetone, methyl ethyl ketone, methyl isobutyl ketone); aliphatic, cycloaliphatic or aromatic hydrocarbons having 4 to 30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, di methylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1 to 30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

In some embodiments, oils or non-aqueous solvents may be employed in the formulations, e.g., to bring one or more of the compounds into solution, due to, for example, the presence of large lipophilic moieties. Alternatively, emulsions, suspensions, or other preparations, for example, liposomal preparations, may be used. With respect to liposomal preparations, for example, any known methods for preparing liposomes may be used. See, for example, Bangham et al., *J. Mol. Biol,* 23: 238-252 (1965) and Szoka et al., Proc. Natl Acad. Sci 75: 4194-4198 (1978), incorporated herein by reference. Thus, in one embodiment, one or more of the compounds are administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines. Ligands may also be attached to the liposomes, for instance, to direct these compositions to particular sites of action.

Other pharmaceutically acceptable solvents for use in the pharmaceutical compositions described herein are well known to those of ordinary skill in the art, and are identified in The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.) (Marcel Dekker, Inc., New York, New York, 1995), The Pharmacological Basis of Therapeutics, (Goodman & Gilman, McGraw Hill Publishing), Pharmaceutical Dosage Forms, (H. Lieberman et al., eds.) (Marcel Dekker, Inc., New York, New York, 1980), Remington's Pharmaceutical Sciences (A. Gennaro, ed., 19th ed.) (Mack Publishing, Easton, Penn., 1995), The United States Pharmacopeia 24, The National Formulary 19, (National Publishing, Philadelphia, Penn., 2000), and A. J. Spiegel et al., Use of Nonaqueous Solvents in Parenteral Products, Journal of Pharmaceutical Sciences, Vol. 52, No. 10, pp. 917-927 (1963).

Formulations containing the pentaaza macrocyclic ring complex, a thioredoxin reductase inhibitor, and/or a glutathione depleting agent may take the form of solid, semi-solid, lyophilized powder, or liquid dosage forms such as, for instance, aerosols, capsules, creams, emulsions, foams, gels/jellies, lotions, ointments, pastes, powders, soaps, solutions, sprays, suppositories, suspensions, sustained-release formulations, tablets, tinctures, transdermal patches, and the like, preferably in unit dosage forms suitable for simple administration of precise dosages. If formulated as a fixed dose, such pharmaceutical compositions or formulation products employ the pentaaza macrocyclic ring complex, a thioredoxin reductase inhibitor, and/or a glutathione depleting agent within accepted dosage ranges.

Formulations for certain pentaaza macrocyclic ring complexes are also described in, for example, in U.S. Pat. Nos. 5,610,293, 5,637,578, 5,874,421, 5,976,498, 6,084,093, 6,180,620, 6,204,259, 6,214,817, 6,245,758, 6,395,725, and 6,525,041 (each of which is hereby incorporated herein by reference in its entirety).

It is contemplated that co-formulations of the pentaaza macrocyclic ring complex, a thioredoxin reductase inhibitor, and/or a glutathione depleting agent may employ conventional formulation techniques for these components individually, or alternative formulation routes, subject to compatibility and efficacy of the various components, in combination.

The above-described pharmaceutical compositions including the pentaaza macrocyclic ring complex, a thioredoxin reductase inhibitor, and/or a glutathione depleting agent may additionally include one or more pharmaceutically active components. Suitable pharmaceutically active agents that may be included in the compositions of the present invention include, for instance, antiemetics, anesthetics, antihypertensives, antianxiety agents, anticlotting agents, anticonvulsants, blood glucose-lowering agents, decongestants, antihistamines, antitussives, antineoplastics, beta blockers, anti-inflammatory agents, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's Disease agents, antibiotics, anti-depressants, and antiviral agents. The individual components of such combinations may be administered either sequentially or simultaneously in separate or combined pharmaceutical formulations.

Combination Treatment with Cancer Therapy

In one embodiment, the pentaaza macrocyclic ring complex, thioredoxin reductase inhibitor and/or glutathione depleting agent can be administered in combination with another cancer therapy, to provide therapeutic treatment. For example, the pentaaza macrocyclic ring complex, thioredoxin reductase inhibitor and/or glutathione depleting agent may be administered as a part of at least one of a chemotherapy treatment and radiation therapy.

In general, the temporal aspects of the administration of the pentaaza macrocyclic ring complex, thioredoxin reductase inhibitor and/or glutathione depleting agent may depend for example, on the particular compound, radiation therapy, or chemotherapy that is selected, or the type, nature, and/or duration of the radiation exposure. Other considerations may include the disease or disorder being treated and the severity of the disease or disorder; activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors. For example, the compounds may be administered in various embodiments before, during, and/or after the administration of the cancer therapy (e.g., radiation therapy or chemotherapy, or before, during or after a course of radiation therapy or chemotherapy comprising multiple exposures and/or doses). By way of another example, the compound may be administered in various embodiments before, during, and/or after an exposure to radiation.

If desired, the effective dose can be divided into multiple doses for purposes of administration; consequently, single dose compositions may contain such amounts or submultiples thereof to make up the dose.

In one embodiment, for example, the pentaaza macrocyclic ring complex, thioredoxin reductase inhibitor and/or glutathione depleting agent are administered to the patient prior to or simultaneous with the cancer therapy corresponding to at least one of radiation therapy and chemotherapy, such as prior to or simultaneous with a dose or dose fraction of such treatment, or prior to or simultaneous with a course of such treatment comprising multiple doses. In another embodiment, for example, the pentaaza macrocyclic ring complex, thioredoxin reductase inhibitor and/or glutathione depleting agent are administered to the patient prior to, but not after, the cancer therapy, such as before but nor after a cancer therapy dose or dose fraction or prior to but not after a course of cancer therapy comprising multiple doses or dose fractions. In yet another embodiment, the pentaaza macrocyclic ring complex, thioredoxin reductase inhibitor and/or glutathione depleting agent are administered to the patient at least 15 minutes, 30 minutes, 45 minutes, 60 minutes, 90 minutes, 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, prior to an initial dose or dose fraction of cancer therapy corresponding to at least one of radiation therapy and chemotherapy. In still other embodiments, for example, the pentaaza macrocyclic ring complex, thioredoxin reductase inhibitor and/or glutathione depleting agent are administered to the patient after a dose or dose fraction of the cancer therapy; thus, for example, the compound may be administered up to 15 minutes, 30 minutes, 45 minutes, 60 minutes, 90 minutes, or 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, after the cancer treatment, such as after a single dose or dose fraction and/or final dose or dose fraction in a course of cancer treatment corresponding to one or more of radiation therapy and chemotherapy.

In another embodiment, for example, the pentaaza macrocyclic ring complex, thioredoxin reductase inhibitor and/or glutathione depleting agent are administered to the patient prior to or simultaneous with the radiation exposure. In another embodiment, for example, the compounds are administered to the patient prior to, but not after, the radiation exposure. In yet another embodiment, the pentaaza macrocyclic ring complex, thioredoxin reductase inhibitor and/or glutathione depleting agent are administered to the patient at least 15 minutes, 30 minutes, 45 minutes, 60 minutes, 90 minutes, 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, prior to the radiation exposure, such as an initial radiation exposure in a course of radiation treatment, or prior to another dose or dose fraction of radiation that is one of the doses or dose fractions of radiation in the course of treatment. In still other embodiments, for example, pentaaza macrocyclic ring complex, thioredoxin reductase inhibitor and/or glutathione depleting agent are administered to the patient after the radiation exposure; thus, for example, the compound may be administered up to 15 minutes, 30 minutes, 45 minutes, 60 minutes, 90 minutes, or 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, after the radiation exposure, which may be a dose or dose fraction of radiation in a multi-dose course of radiation therapy, or may be the single or final dose or dose fraction of radiation in the radiation therapy.

In one embodiment, the pentaaza macrocyclic ring complex, thioredoxin reductase inhibitor and/or glutathione depleting agent are administered as a part of a course of therapy that includes the radiation therapy. In radiation therapy, a patient receives a dose of ionizing radiation to kill or control the growth of cancerous cells. The dose of radiation may be directed at a specific part of the body, and the beam of radiation may also be shaped according to a predetermined treatment regimen, to reduce deleterious effects on parts of the body not afflicted with cancer. A typical course of radiation therapy may include one or a plurality of doses of radiation, which can be administered over the course of days, weeks and even months. A total "dose" of radiation given during a course of radiation therapy typically refers to the amount of radiation a patient receives during the entire course of radiation therapy, which doses may be administered as dose "fractions" corresponding to multiple radiation exposures in the case where the total dose is administered over several sessions, with the sum of the fractions administered corresponding to the overall dose. As is discussed in more detail in the Examples section below, the administration of pentaaza macrocyclic ring complex with at least one of thioredoxin reductase inhibitor and glutathione depleting agent demonstrates unexpected synergistic effects in sensitizing cancer cells to radiation therapy, thereby improving the efficacy of radiation treatment.

In one embodiment, at least one of the pentaaza macrocyclic ring complex, thioredoxin compound and glutathione depleting agent are administered within a predetermined time period before or after a radiation dose is administered. For example, the pentaaza macrocyclic ring complex, thioredoxin reductase inhibitor and/or glutathione depleting agent may be administered within 1 week, 48 hours, 24 hours, 12 hours, 6, hours, 2 hours, 1 hour or even within 30 minutes of the patient receiving the radiation exposure, such as the dose or dose fraction (either before or after the radiation exposure corresponding to the radiation dose or dose fraction). Other durations between the radiation dose and administration of the compound that result in the enhanced the killing of cancer cells may also be suitable. In one embodiment, one or more of the pentaaza macrocyclic ring complex, thioredoxin reductase inhibitor and/or glutathione depleting agent may be administered before the radiation exposure (such as before a dose or dose fraction), and the remaining one or more of the pentaaza macrocyclic ring complex, thioredoxin reductase inhibitor and/or glutathione depleting agent can be administered after the exposure (such as after a dose or dose fraction). One or more of the pentaaza macrocyclic ring complex, thioredoxin reductase inhibitor and/or glutathione depleting agent may also be administered both before and after administration of a radiation exposure.

In one embodiment, a course of radiation therapy includes a plurality of radiation doses or dose fractions given over a predetermined period of time, such as over the course of hours, weeks, days and even months, with the plural doses or dose fractions being either of the same magnitude or varying. That is, course of radiation therapy can comprise the administration of a series of multiple doses or dose fractions of radiation. In one embodiment, the active agent and pentaaza macrocyclic ring complex can be administered before one or more radiation doses or dose fractions in the series, such as before each radiation dose, or before some fraction of the radiation doses. Furthermore, the administration of the pentaaza macrocyclic ring complex, thioredoxin reductase inhibitor and/or glutathione depleting agent during the course of radiation therapy can be selected to enhance the cancer treating effects of the radiation therapy, such as by sensitizing cancer cells to the radiation therapy. In one embodiment, the pentaaza macrocyclic ring complex, thioredoxin reductase inhibitor and/or glutathione depleting agent are administered within a predetermined duration before or after each dose or dose fraction, such as the predetermined duration discussed above. In another embodiment, the pentaaza macrocyclic ring complex, thioredoxin reductase inhibitor and/or glutathione depleting agent are administered within a predetermined duration of time before or after only select doses or dose fractions. In yet another embodiment, at least one of the pentaaza macrocyclic ring complex, thioredoxin reductase inhibitor and/or glutathione depleting agent is administered within a predetermined duration of time before the doses or dose fractions, while another of the pentaaza macrocyclic ring complex, thioredoxin reductase inhibitor and/or glutathione depleting agent is administered within a predetermined duration of time after the doses or dose fractions. In a further embodiment, at least one of the pentaaza macrocyclic ring complex, thioredoxin reductase inhibitor and/or glutathione depleting agent is administered only within the predetermined duration before or after select doses or dose fractions, while another of the pentaaza macrocyclic ring complex, thioredoxin reductase inhibitor and/or glutathione depleting agent is administered only within the predetermined duration before or after doses or dose fractions other than the select doses or dose fractions.

A suitable overall dose to provide during a course of therapy can be determined according to the type of treatment to be provided, the physical characteristics of the patient and other factors, and the dose fractions that are to be provided can be similarly determined. In one embodiment, a dose fraction of radiation that is administered to a patient may be at least 1.8 Gy, such as at least 2 Gy, and even at least 3 Gy, such as at least 5 Gy, and even at least 6 Gy. In yet another embodiment, a dose fraction of radiation that is administered to a patient may be at least 10 Gy, such as at least 12 Gy, and even at least 15 Gy, such as at least 18 Gy, and even at least 20 Gy, such as at least 24 Gy. In general, a dose fraction of radiation administered to a patient will not exceed 54 Gy. Furthermore, it should be noted that, in one embodiment, a dose fraction delivered to a subject may refer to an amount delivered to a specific target region of a subject, such as a target region of a tumor, whereas other regions of the tumor or surrounding tissue may be exposed to more or less radiation than that specified by the nominal dose fraction amount.

In yet another embodiment, the pentaaza macrocyclic ring complex, thioredoxin reductase inhibitor and/or glutathione depleting agent are administered as a part of a course of therapy that includes chemotherapy. In chemotherapy, chemotherapeutic agents are administered to a patient to kill or control the growth of cancerous cells. A typical course of chemotherapy may include one or a plurality of doses of one or more chemotherapeutic agents, which can be administered over the course of days, weeks and even months. Chemotherapeutic agents can include at least one of: alkylating antineoplastic agents such as nitrogen mustards (e.g. cyclophosphamide, chlorambucil), nitrosoureas (e.g. n-nitroso-n-methylurea, carmustine, semustine), tetrazines (e.g. dacarbazine, mitozolimide), aziridines (e.g. thiotepa, mytomycin), cisplatins (e.g. cisplatin, carboplatin, oxaliplatin); anti-metabolites such as anti-folates (e.g. methotrexate and pemetrexed), fluoropyrimidines (e.g., fluorouracil, capecitabine), deoxynucleoside analogs (e.g. cytarabine, gemcitabine, decitabine) and thiopurines (e.g., thioguanine, mercaptopurine); anti microtubule agents such as taxanes (e.g.

paclitaxel, docetaxel); and topoisomerase inhibitors (e.g. etoposide, doxorubicin, mitoxantrone, teniposide). For example, the chemotherapeutic agent may be selected from the group consisting of all-trans retinoic acid, azacitidine, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tiguanine, valrubicin, vinblastine, vincristine, vindesine, and vinorelbine. The administration of many of the chemotherapeutic agents is described in the "Physicians' Desk Reference" (PDR), e.g., 1996 edition (Medical Economics Company, Montvale, N.J. 07645-1742, USA).

In one embodiment, at least one of the pentaaza macrocyclic ring complex, thioredoxin compound and glutathione depleting agent are administered within a predetermined time period before or after a dose of a chemotherapeutic agent is administered. For example, the pentaaza macrocyclic ring complex, thioredoxin reductase inhibitor and/or glutathione depleting agent may be administered within 1 week, 48 hours, 24 hours, 12 hours, 6, hours, 2 hours, 1 hour or even within 30 minutes of the patient receiving the dose of chemotherapeutic agent (either before or after the dose of chemotherapeutic agent). Other durations between the chemotherapeutic agent dose and administration of the compound that result in the enhanced the killing of cancer cells may also be suitable. In one embodiment, one or more of the pentaaza macrocyclic ring complex, thioredoxin reductase inhibitor and/or glutathione depleting agent may be administered before the dose of the chemotherapeutic agent, and the remaining one or more of the pentaaza macrocyclic ring complex, thioredoxin reductase inhibitor and/or glutathione depleting agent can be administered after the dose of the chemotherapeutic agent. One or more of the pentaaza macrocyclic ring complex, thioredoxin reductase inhibitor and/ or glutathione depleting agent may also be administered both before and after administration of the dose of chemotherapeutic agent.

In one embodiment, a course of chemotherapy includes a plurality of doses of a chemotherapeutic agent given over a predetermined period of time, such as over the course of hours, weeks, days and even months. The plural doses may be either of the same magnitude or varying, and can include doses of the same or different chemotherapeutic agents and/or a combination of chemotherapeutic agents. The administration of the pentaaza macrocyclic ring complex, thioredoxin reductase inhibitor and/or glutathione depleting agent during the course of chemotherapy can be selected to enhance the cancer treating effects of the chemotherapy, such as by increasing intracellular levels of hydrogen peroxide in the cancer cells. In one embodiment, the pentaaza macrocyclic ring complex, thioredoxin reductase inhibitor and/or glutathione depleting agent are administered within a predetermined duration before or after each dose, such as the predetermined duration discussed above. In another embodiment, the pentaaza macrocyclic ring complex, thioredoxin reductase inhibitor and/or glutathione depleting agent are administered within a predetermined duration of time before or after only select doses. In yet another embodiment, at least one of the pentaaza macrocyclic ring complex, thioredoxin reductase inhibitor and/or glutathione depleting agent is administered within a predetermined duration of time before the doses, while another of the pentaaza macrocyclic ring complex, thioredoxin reductase inhibitor and/or glutathione depleting agent is administered within a predetermined duration of time after the doses. In a further embodiment, at least one of the pentaaza macrocyclic ring complex, thioredoxin reductase inhibitor and/or glutathione depleting agent is administered only within the predetermined duration before or after select doses, while another of the pentaaza macrocyclic ring complex, thioredoxin reductase inhibitor and/or glutathione depleting agent is administered only within the predetermined duration before or after doses other than the select doses.

In yet another embodiment, at least one of the pentaaza macrocyclic ring complex, thioredoxin reductase inhibitor and/or glutathione depleting agent is administered in combination with both a radiation therapy and chemotherapy.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Steady-state levels of pro-oxidants in human breast (MB231) and lung cancer (H1299) cells were investigated versus normal breast (HMEC) and lung cancer epithelial cells (HBEpC), to determine whether the cancerous cells exhibited a higher level of the pro-oxidants. The fluorescent probe 5-(and 6) carboxy-2',7' dichlorodihydrofluorescein diacetate (DCFH2) was used as a non-specific oxidation sensitive fluorescence probe. Cells were grown in culture for 48 hours, and stained with oxidation sensitive dyes at 4% $O_2$, to approximate physiologically relevant $O_2$ concentrations. The fluorescence intensity of 10,000 cells/sample were analyzed using a Becton Dickenson FACScan system. The results are shown in FIG. 1, and show that the cancer cells MB231 and H1299 have approximately 3-5 times more DCFH2 oxidation as compared to the normal HMEC or HBEpC cells. The results demonstrated that the cancer cells have higher steady-state levels of pro-oxidants at baseline than normal cells, and thus show a mechanism that can be exploited for cancer-cell selective treatment.

Example 2

Figure 2:
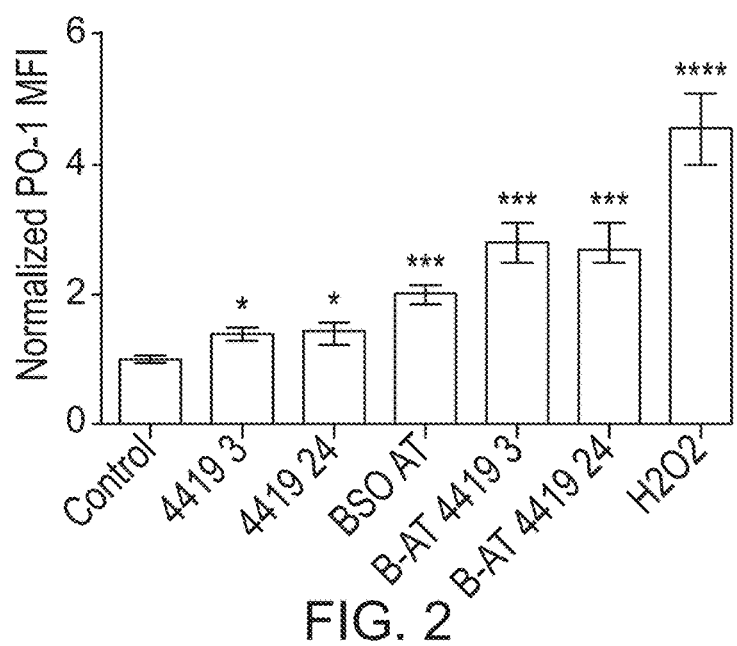
FIG. 2 shows the normalized mean fluorescence intensity (MFI) for PeroxyOrange-1 (PO-1) oxidation as a measure of steady-state $H_2O_2$ in H292 cells treated with GC4419 alone, as well as for H292 cells treated with combinations of buthionine sulfoximine (BSO) and 3-aminotriazole (AT), and combinations of BSO and AT with GC4419, as compared to a control.

The effects on $H_2O_2$ fluxes of a pentaaza macrocyclic ring complex (GC4419) provided in combination with inhibitors of $H_2O_2$ metabolism were tested in human lung cancer cells (H292). The H292 cells were treated with 20 μM GC4419 for 3 and 24 hours, and PeroxyOrange-1 (PO-1) oxidation was monitored as a measure of steady-state $H_2O_2$. The results are shown in FIG. 2. The results demonstrate that a 1.5-fold increase in PO-1 oxidation is exhibited at both 3 hours (4419 3) and 24 hours (4419 24) after exposure to the 20 μM GC4419, as compared to the control. The results also show that depletion of glutathione by treating the cells with 100 μM buthionine sulfoximine (BSO) while inhibiting catalase using 3-aminotriazole (AT) (a compound that irreversible inhibits catalase enzyme and thus inhibits the metabolism of $H_2O_2$ independently of glutathione) increases PO-1 oxidation 2-fold. Also, the combination of GC4419+ BSO+AT for 3 hours (B-AT 4419 3) and 24 hours (B-AT 4419 24) further increased PO-1 oxidation to 3-fold greater than a control. The PO-1 oxidation was also monitored in dosing the cells three times with 100 μM hydrogen peroxide ($H_2O_2$). Accordingly, the results show that the pentaaza macrocyclic ring complex GC4419 could increase intracellular steady-state levels of $H_2O_2$, with the increase being further enhanced by compounds that inhibit $H_2O_2$ metabolism pathways.

Example 3

Figure 3:
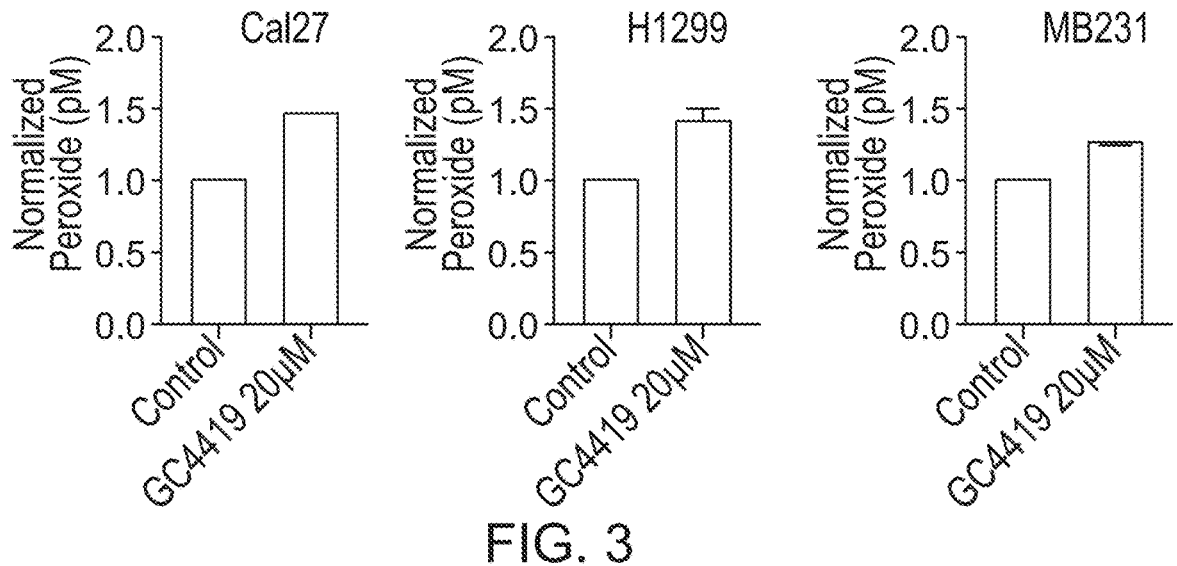
FIG. 3 shows normalized levels of peroxide flux, measured as the 3-aminotriazole inactivation of catalase, in head and neck cancer cells (Cal27), lung cancer cells (H1299) and breast cancer cells (MB231) treated with GC4419, compared to a control untreated with GC4419.

The effect of the pentaaza macrocyclic ring complex GC4419 in increasing levels of $H_2O_2$ in cancer cells was further tested by measuring the 3-aminotriazole mediated inactivation of catalase, using a method as described in Ahmad et al, *J. Biol Chem*, 280(6), 4254-4263 (2005). Briefly, head and neck cancer cells (Cal27), lung cancer cells (H1299) and breast cancer cells (MB231) were grown in 60 mm dishes, transduced with 50 MOI adCat to genetically increase catalase expression, and allowed 48 hours to recover so that the activity of catalase could increase to maximal levels. Afterwards, 50 mM AT was added for 5 minutes, which irreversibly binds to and inhibits the catalase intermediate formed in the presence of $H_2O_2$. 20 μM GC4419 was added, and cells were collected at 10 minute intervals for 60 minutes, and the inhibition of catalase was determined. A Lowry's protein assay determined the total protein concentration of individual samples. This method provides a stoichiometry of one catalase molecule being inhibited for each molecule of $H_2O_2$, thereby providing for precise measurements of changes in $H_2O_2$ flux. The results are shown in FIG. 3 (left hand side is Cal27, middle is H1299, and right hand side is MB231). The results demonstrated significant increases in steady-state levels of intracellular $H_2O_2$ flux in both the lung and breast cancer cell lines when treated with GC4419, as normalized to the control. Thus, GC4419 has been demonstrated to significantly increase the $H_2O_2$ flux in cancer cells.

Example 4

Figure 4:
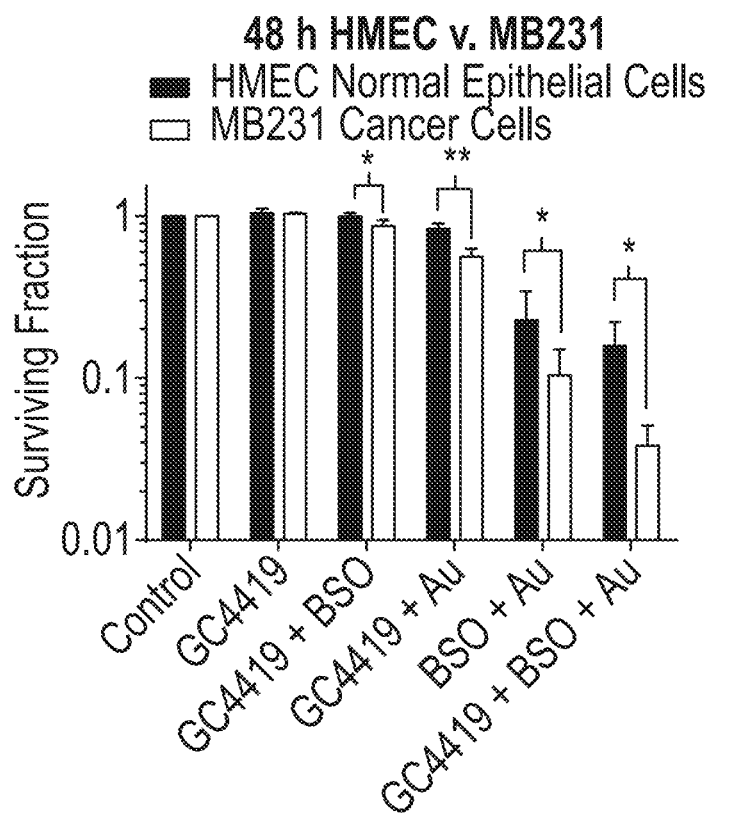
FIG. 4 shows the surviving fraction of MB231 and H1299 cancer cells as compared to HMEC and HBEpC normal epithelial cells, following treatment with (i) GC4419, (ii) GC4419 and BSO, (iii) GC4419 and auranofin (Au), (iv) BSO and Au, and (v) GC4419, BSO and Au, as compared to a control.
Figure 4:
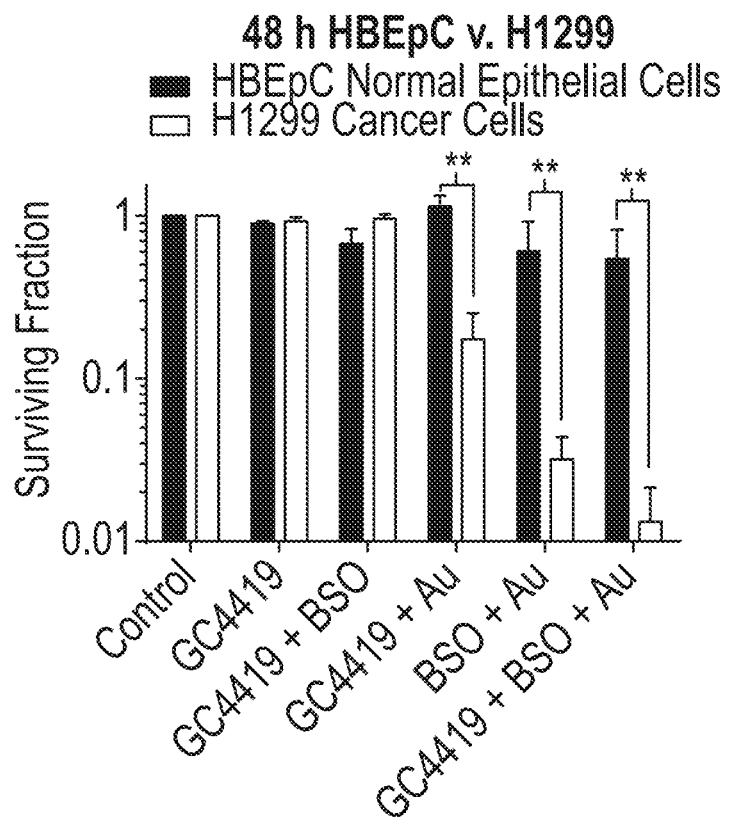

The effect of the pentaaza macrocyclic ring complex GC4419 in combination with inhibitors of hydrogen peroxide metabolism was tested on breast cancer cells (MB231) and non-small cell lung cancer cells (H1299) versus normal cells (HMEC normal mammary epithelial cells and HBEpC normal bronchial epithelial cells). The cells were plated and grown exponentially for 2 days. Either or both of 20 μM of the CG4419 compound and 100 μM BSO were added at time 0 of exposure, and 500 nM Auranofin (a thioredoxin reductase inhibitor) was added 48 hours after, for 15 minutes prior to a clonogenic assay. The results are shown in FIG. 4. The results showed that the combination of GC4419 with auranofin (Au) and/or BSO produced synergistic effects in the selective killing of cancer cells as compared to any of the compounds alone. In particular, the combination of GC4419 with auranofin provides significantly improved selective killing of cancer cells as compared to GC4419 alone. The combination of all of GC4419, BSO and AU provided the greatest killing of cancer cells, and the greatest selectivity in killing of cancer cells versus normal cells. Thus, the results demonstrate the effectiveness of inhibiting hydrogen peroxide detoxification pathways in the selective killing of cancer cells using GC4419.

Example 5

Figure 5:
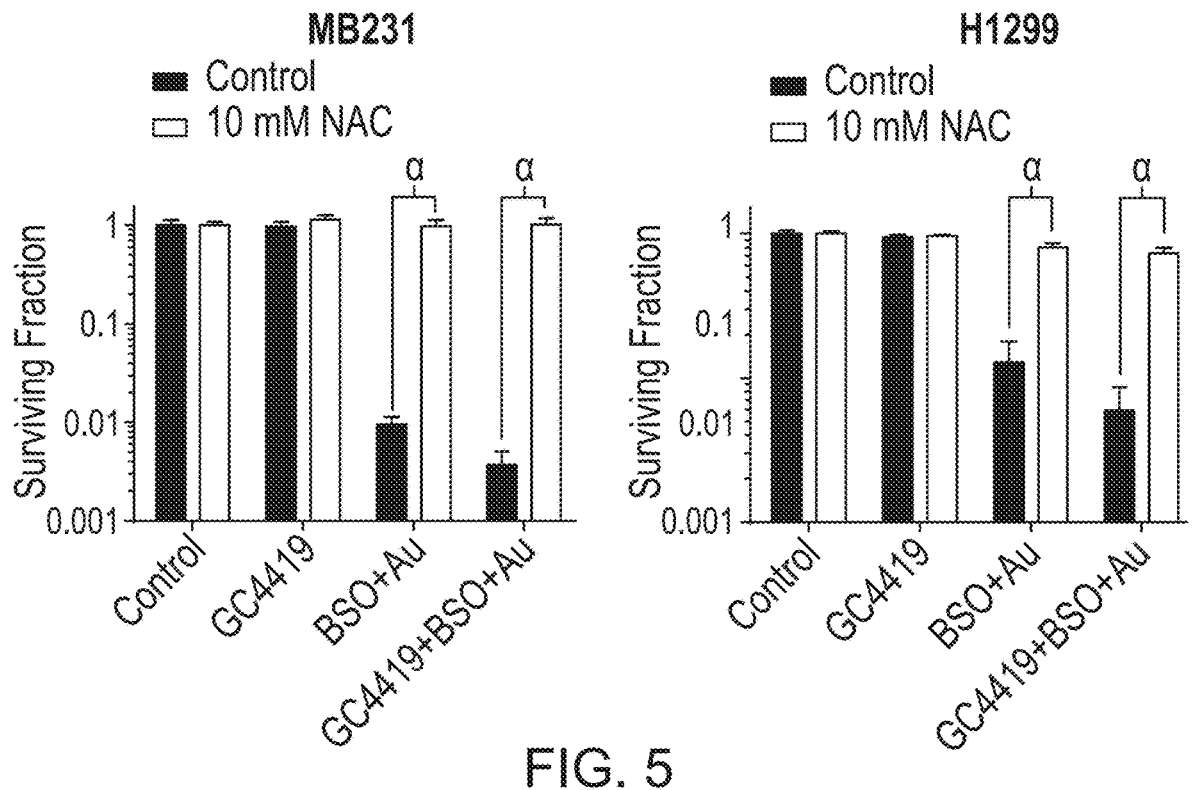
FIG. 5 shows the surviving fraction of MB231 and H1299 cancer cells, following treatment with (i) GC4419, (ii) BSO and Au, and (iii) GC4419, BSO and Au, both in the presence and in the absence of the thiol antioxidant N-acetylcysteine (NAC).

To determine whether the synergistic effects of the pentaaza macrocyclic ring complex (GC4419) with hydrogen peroxide metabolism inhibitors (BSO and/or Au) was related to oxidative stress, tests on cancer cell clonogenic killing was performed in the presence and absence of the thiol antioxidant N-acetylcysteine (NAC). Breast cancer cells (MB231) and lung cancer cells (H1299) were grown in culture to 75% confluence and treated with either 20 μM GC4419, or 100 μM BSO with 500 nM Au added after 48 hours, or all of GC4419, BSO and Au. The cancer cells were also treated with the same sets of compounds, but with the further addition of 10 mM of NAC. The results are shown in FIG. 5. Significantly, the addition of NAC nearly completely inhibited the cell killing caused by GC4419+Au and/or BSO. Thus, the results support that pentaaza macrocyclic ring complexes such as GC4419 combined with inhibitors of hydrogen peroxide metabolism can selectively kill cancer cells versus normal cells via oxidative stress correlated with increase $H_2O_2$ fluxes.

Example 6

Figure 6:
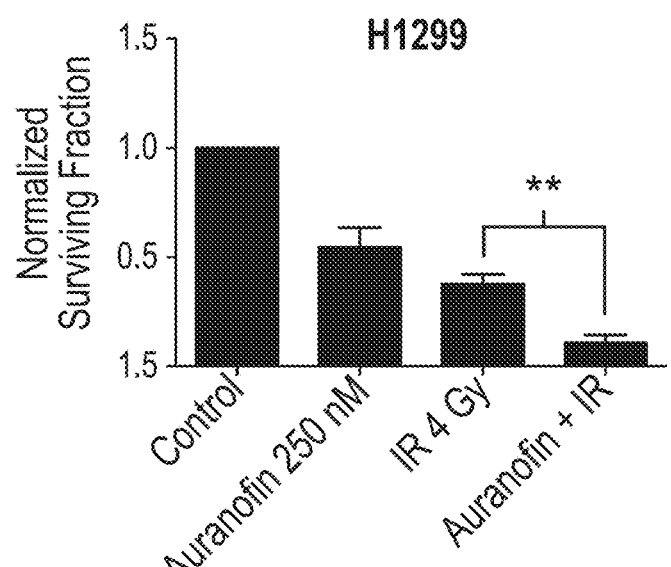
FIG. 6 shows the normalized surviving fraction of H1299 cancer cells, following treatment with (i) Au, (ii) ionizing radiation (IR), and (iii) Au in combination with IR, as compared to a control.

The effects of an inhibitor of hydrogen peroxide metabolism, auranofin (a thioredoxin reductase inhibitor), on cancer cells was tested in a clonogenic cell survival assay to determine the effects of the compound alone and in combination with ionizing radiation. Non-small cell lung cancer cells (H1299) were exponentially grown and treated with auranofin (Au) either by itself for 15 minutes, or 15 minutes prior to the first of two ionizing radiation (IR) doses (2 Gy each) spaced 24 hours apart. After the last ionizing radiation dose, the cells were trypsinized, counted, replated at varying lower densities and incubated for 12 days. Plates were stained and counted for clonogenic survival assays. The results are shown in FIG. 6. The results show that treatment with 250 nM of Au (Auranofin 250 nM) resulted in significant cell killing, as compared to a control. Furthermore, treatment with auranofin sensitized the cancer cells to radiation, thereby increasing the efficiency of the ionizing radiation in cell killing (Auranofin+IR) as compared to administration of ionizing radiation alone (IR 4 Gy). Accordingly, the results show that auranofin significantly increases the response of cancer cells to ionizing radiation.

Furthermore, comparing the results in FIG. 6 with those of FIG. 4 above, it can be seen that the combination of the thioredoxin reductase inhibitor auranofin with the pentaaza macrocyclic ring complex GC4419 (GC4419+Au in FIG. 4) provide synergistic effects in the selective killing of cancer cells, as compared to GC4419 alone (GC4419 in FIG. 4) or auranofin alone (Auranofin 250 nM in FIG. 6). In particular, while 20 μM GC4419 in FIG. 4 results in a normalized surviving cell fraction (on a log scale) of H1299 cancer cells of about 1 (with the control also being about 1), and 250 nM of auranofin in FIG. 6 results in a normalized surviving cell fraction of H1299 cancer cells of a little over 0.5, the combination of 20 μM GC4419 with 500 nM of auranofin in FIG. 6 results in a normalized survival fraction (on a log scale) of H1299 cancer cells of less than 0.2, meaning that the combination of GC4419 and auranofin provides a greater than additive effect in the selective killing of cancer cells over either the GC4419 or auranofin alone.

Example 7

Figure 7:
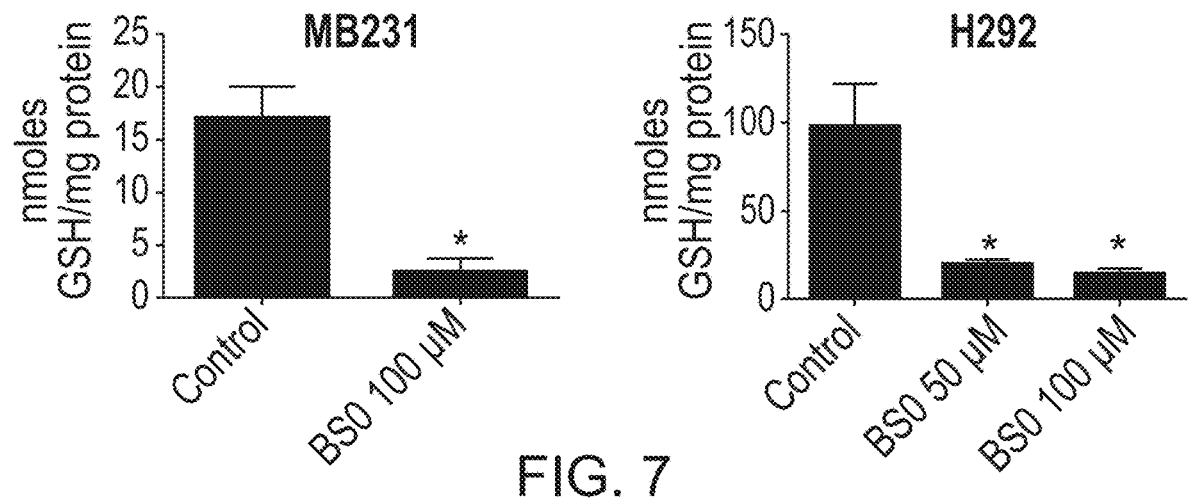
FIG. 7 shows total glutathione levels as measured using a DTNB recycling spectrophotometric assay, for breast cancer cells (MB231) and lung cancer cells (H292) treated with BSO.

The effect of buthionine sulfoximine (BSO) on reduced glutathione (GSH) levels in breast cancer cells (MB231) and lung cancer cells (H292) was examined. The cells were plated and grown to 75% confluency, then treated with either 50 μM BSO or 100 μM BSO for another 24 hours before harvesting for analysis for total glutathione levels using a DTNB recycling spectrophotometric assay. The results are shown in FIG. 7, and demonstrate that BSO significantly decreases glutathione levels in the cancer cells.

Example 8

Figure 8:
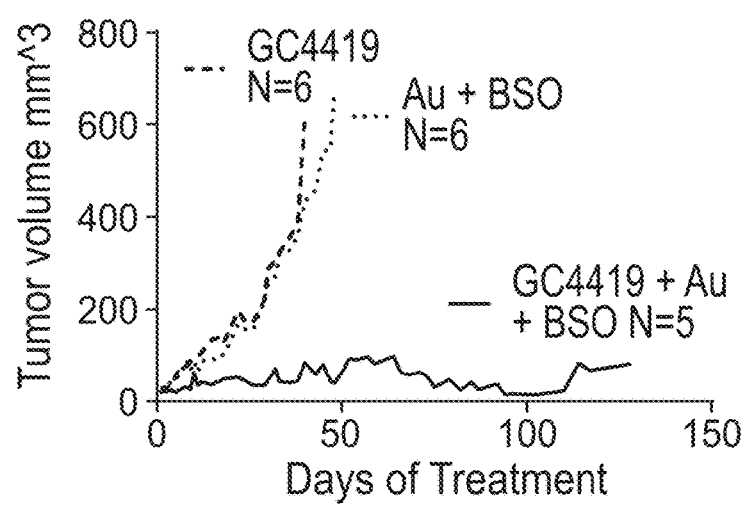
FIG. 8 shows tumor volumes over time post treatment of MB231 breast cancer xenografts in mice, where treatment included exposure to (i) GC4419 alone, (ii) combination of the Au and BSO, and (iii) the combination of GC4419, Au and BSO.

The effects of the pentaaza macrocyclic ring complex GC4419 alone, and in combination with the thioredoxin reductase inhibitor auranofin (Au) and the glutathione depleting agent BSO, were tested in an in vivo model of breast cancer. MB231 breast cancer xenografts were grown in flanks of nude mice, and once tumors reached 2-4 mm diameter, the mice were treated with either BSO at 225 mg/kg i.p and Au at 1.5 mg/kg i.p. daily (Au+BSO), GC4419 at 9 mg/kg i.p. daily (GC4419), or GC4419 given daily in combination with BSO and Au (GC4419+AU+BSO). Tumor growth averages were measured. The results are shown in FIG. 8. The results demonstrate that the combined therapy with GC4419 and Au+BSO resulted in a dramatic decrease in tumor volume as compared to GC4419 alone, or Au+BSO alone. The results thus show the synergistic effects of the combination of the pentaaza macrocyclic ring complex GC4419 with the thioredoxin reductase inhibitor auranofin and the glutathione-depleting agent BSO in an in vivo therapy regimen.

Example 9

Figure 9:
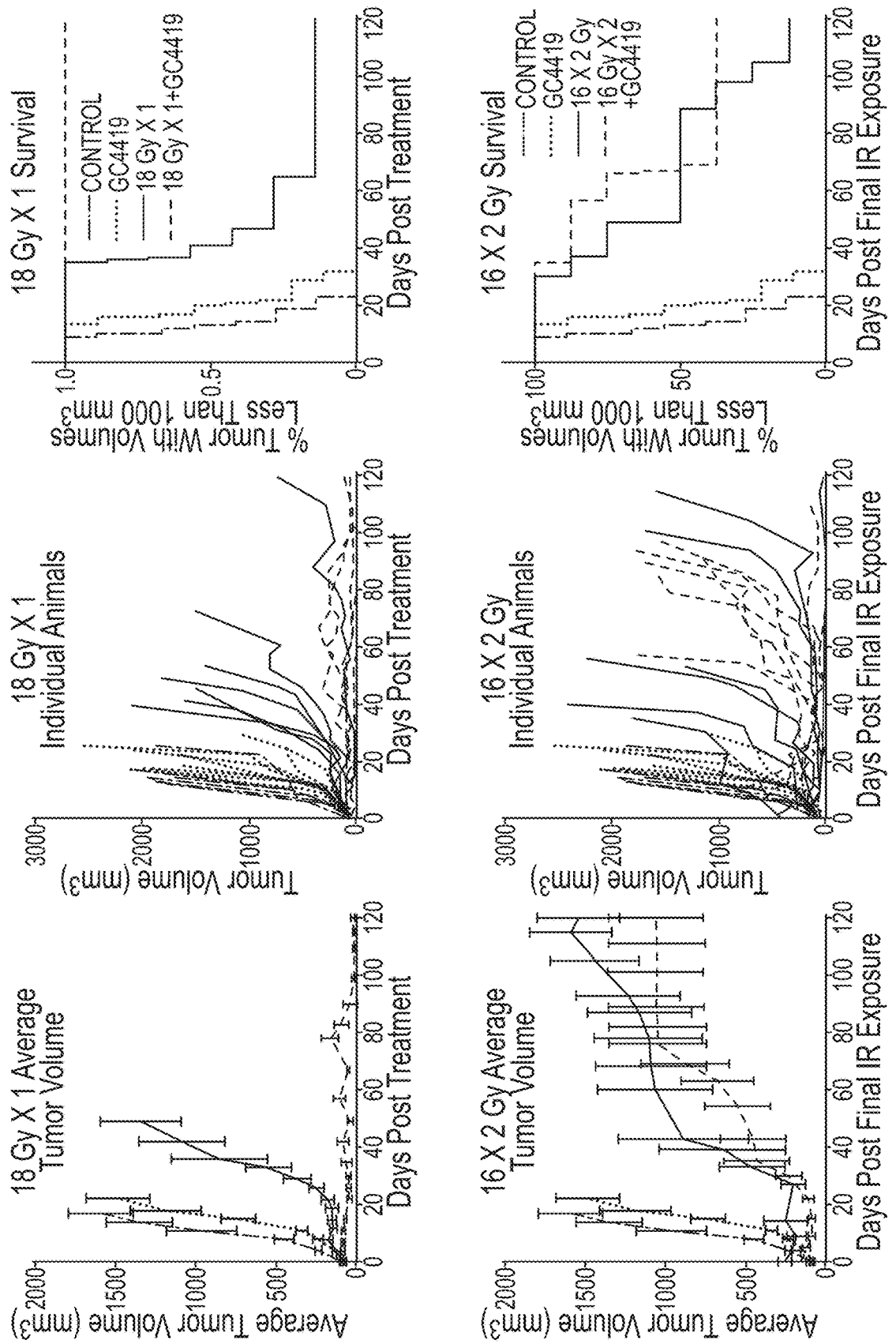
FIG. 9 shows average tumor volumes, tumor volumes for individual animals, and the percentage of tumors with volumes less than 1000 mm$^3$ for a non-small cell lung cancer tumor xenograft model, over time post treatment (post-final IR exposure), with treatment with GC4419, treatment with IR (18 Gy×1 dose or 2 GY×16 doses), and treatment with a combination of IR and GC4419, as compared to control.

The effect of the pentaaza macrocyclic ring complex GC4419 was tested in vivo on non-small cell lung cancer (NSCLC) in a tumor xenograft model. Subcutaneous H1299 tumors were subjected to biologically equivalent fractionation schemes of 18 Gy×1 dose or 2 Gy×16 doses (delivered on consecutive days), 1 hour following an initial injection of 24 mg/kg GC4419. GC4419 was also administered on the next 4 consecutive days after the first injection (given, in the case of the 2 Gy fraction dose experiment, 1 hour prior to each of those 4 days' radiation treatments). The results are shown in FIG. 9. The data demonstrate that GC4419 exhibits an anti-cancer effect in reduced cancer size as well as improved survival as compared to the control. The data also shows that GC4419 increases the response of NSCLC tumors to radiation, significantly enhancing radiation induced growth delay, and survival.

Example 10

Figure 10:
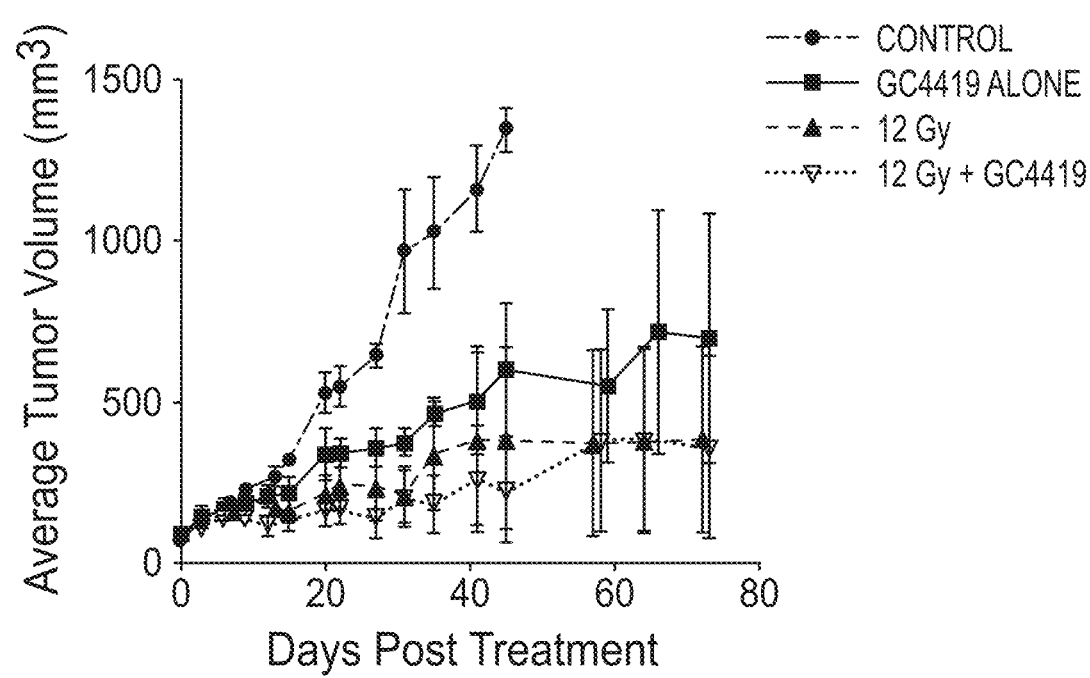
FIG. 10 shows average tumor volumes over time post treatment, in animal models of squamous cell carcinoma of the head and neck (HNSCC), for treatment with (i) GC4419, (ii) IR (12 Gy×1), and (iii) IR and GC4419, in comparison to control.
Figure 12:
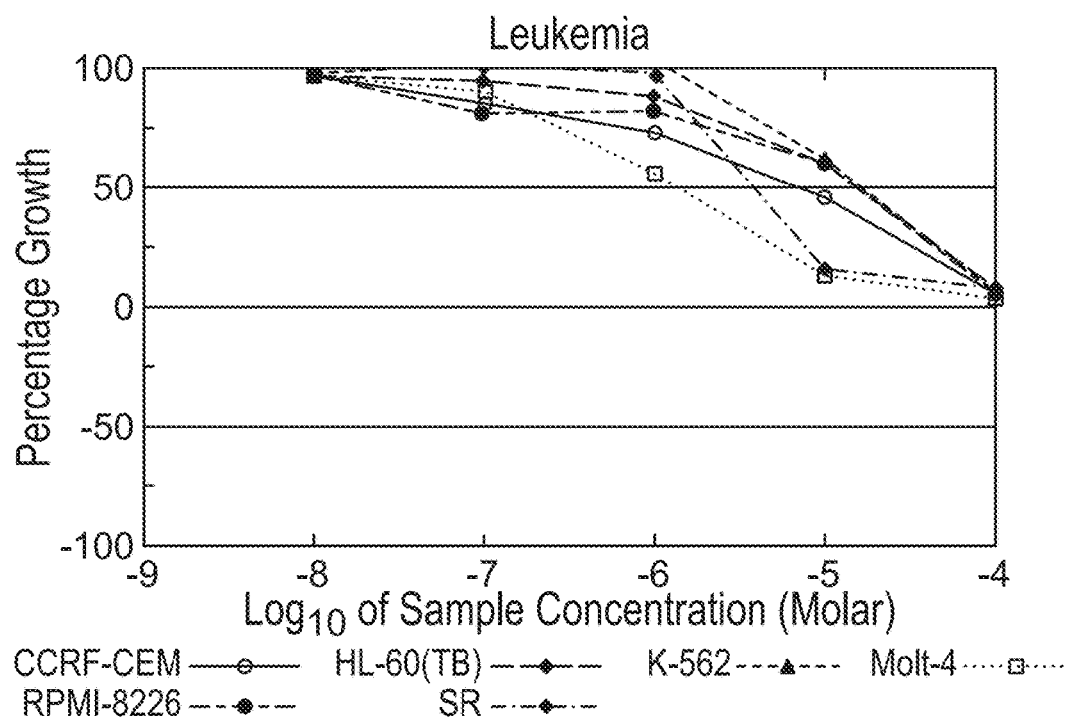
FIG. 12 shows percentage growth of leukemia cell lines incubated at different concentrations of the pentaaza macrocyclic ring complex M40401 (GC4401), to provide in vitro screening for the anti-proliferative effects of the pentaaza macrocyclic ring complex in the cancerous cell lines.
Figure 13:
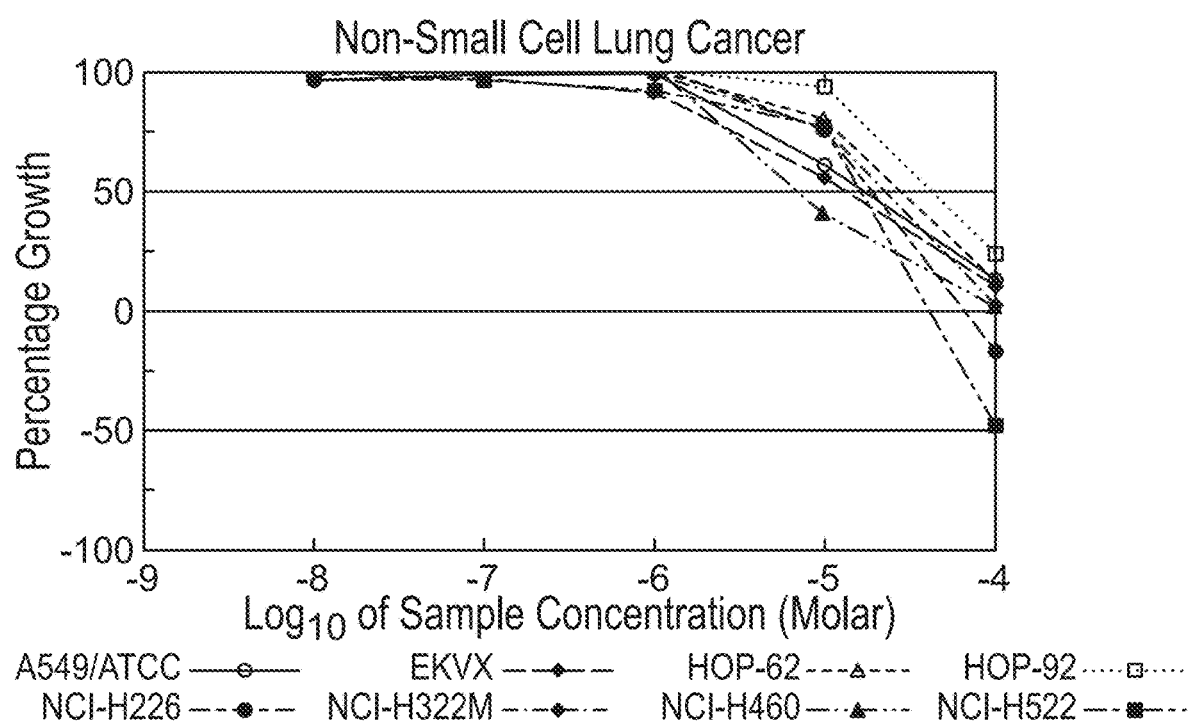
FIG. 13 shows percentage growth of non-small cell lung cancer cell lines incubated at different concentrations of the pentaaza macrocyclic ring complex M40401 (GC4401), to provide in vitro screening for the anti-proliferative effects of the pentaaza macrocyclic ring complex in the cancerous cell lines.
Figure 14:
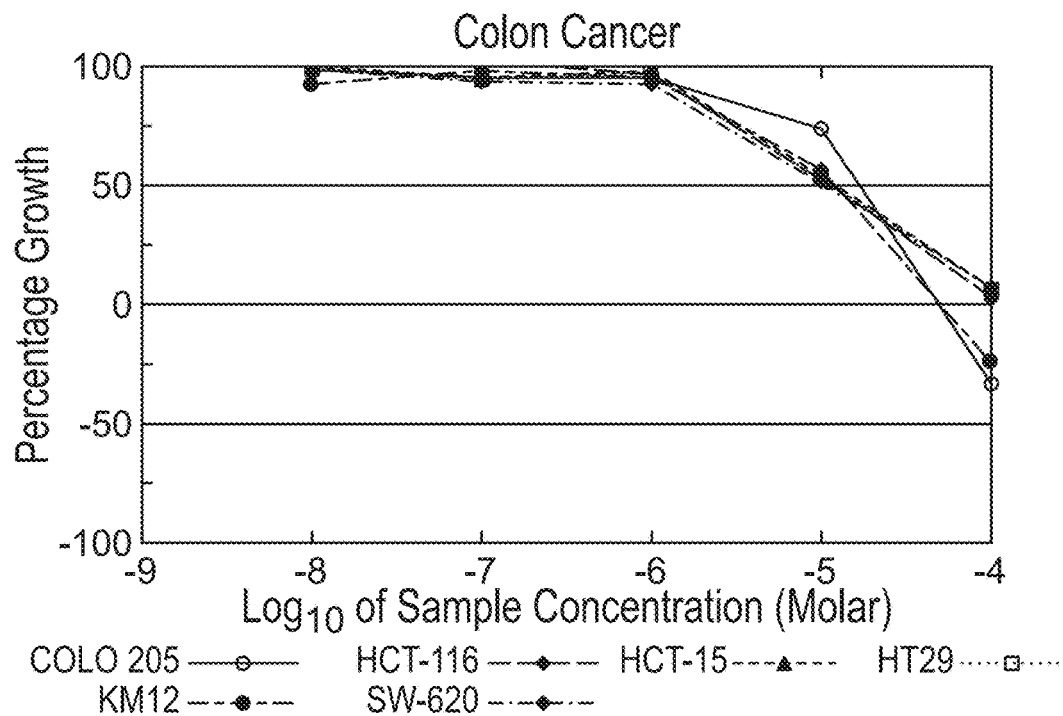
FIG. 14 shows percentage growth of colon cancer cell lines incubated at different concentrations of the pentaaza macrocyclic ring complex M40401 (GC4401), to provide in vitro screening for the anti-proliferative effects of the pentaaza macrocyclic ring complex in the cancerous cell lines.
Figure 15:
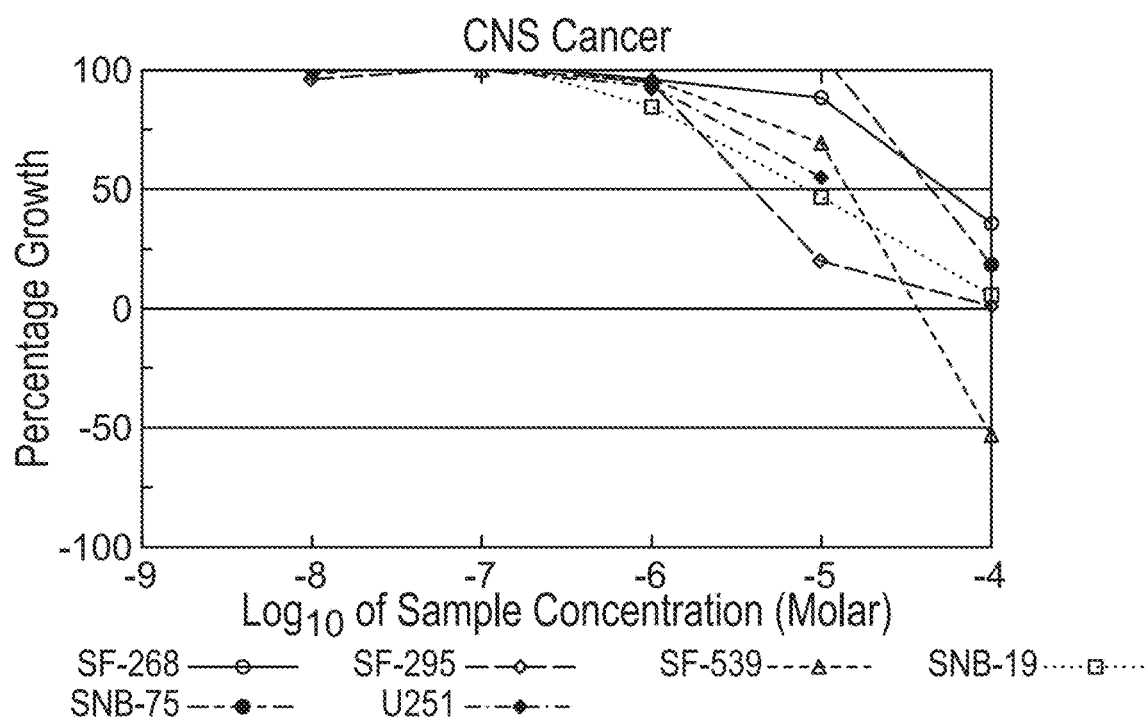
FIG. 15 shows percentage growth of CNS cancer cell lines incubated at different concentrations of the pentaaza macrocyclic ring complex M40401 (GC4401), to provide in vitro screening for the anti-proliferative effects of the pentaaza macrocyclic ring complex in the cancerous cell lines.
Figure 16:
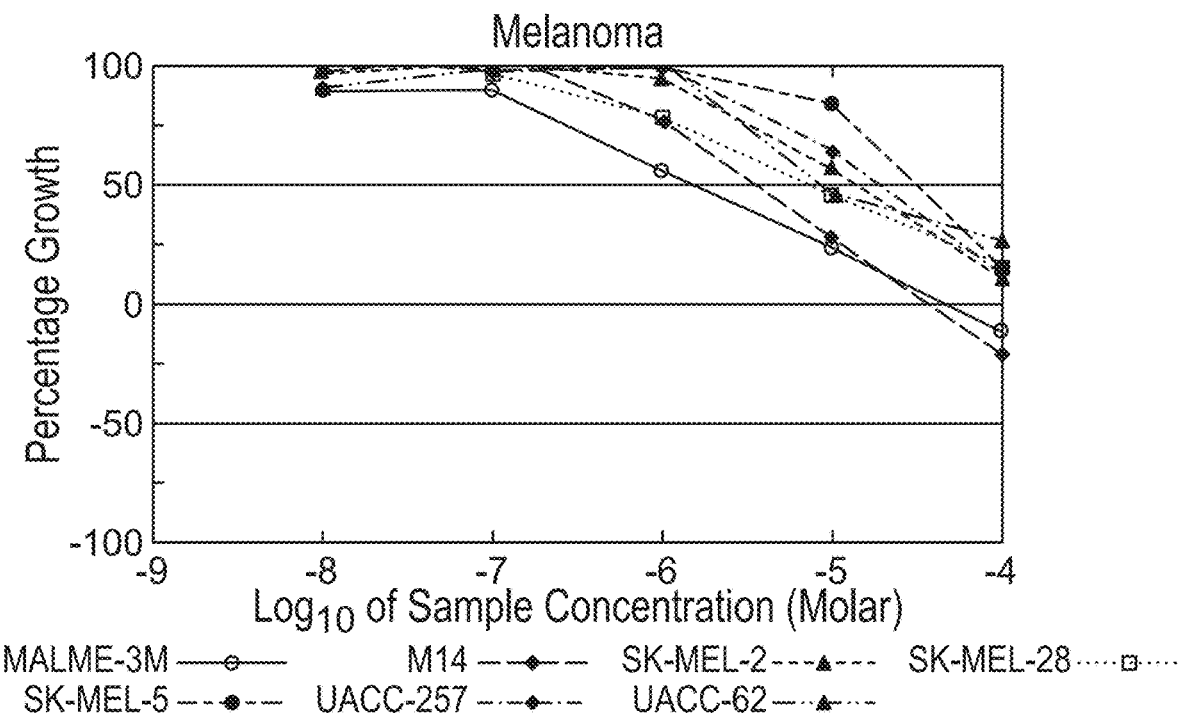
FIG. 16 shows percentage growth of melanoma cancer cell lines incubated at different concentrations of the pentaaza macrocyclic ring complex M40401 (GC4401), to provide in vitro screening for the anti-proliferative effects of the pentaaza macrocyclic ring complex in the cancerous cell lines.
Figure 17:
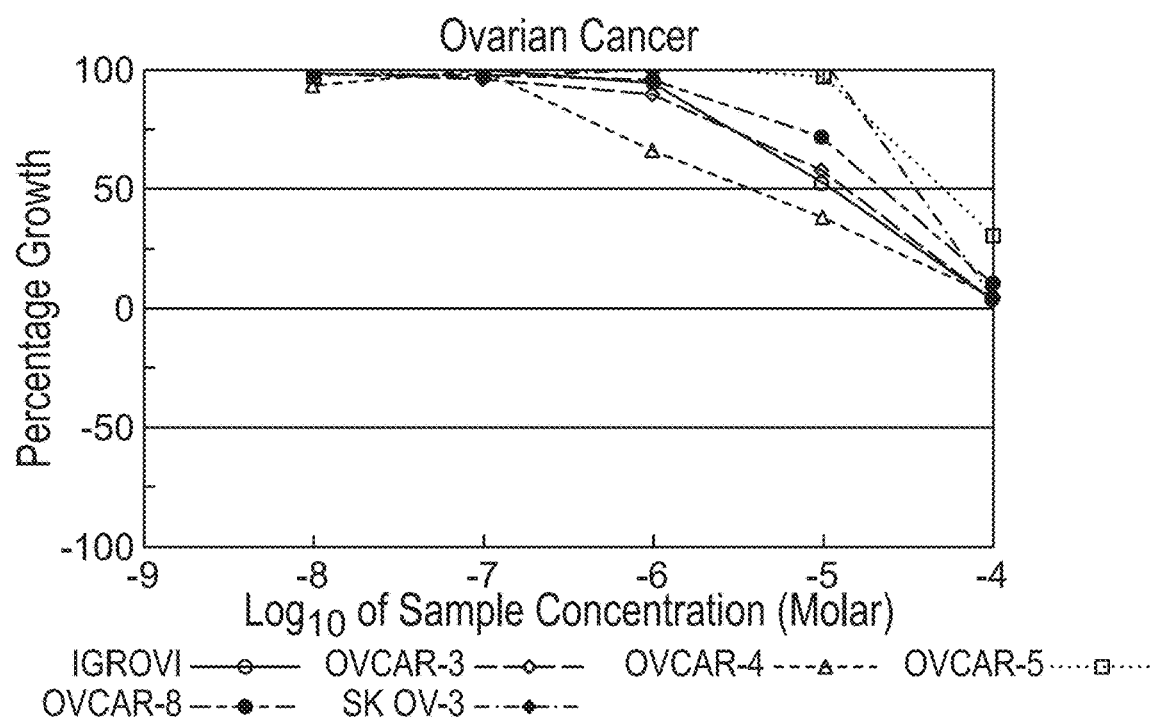
FIG. 17 shows percentage growth of ovarian cancer cell lines incubated at different concentrations of the pentaaza macrocyclic ring complex M40401 (GC4401), to provide in vitro screening for the anti-proliferative effects of the pentaaza macrocyclic ring complex in the cancerous cell lines.
Figure 18:
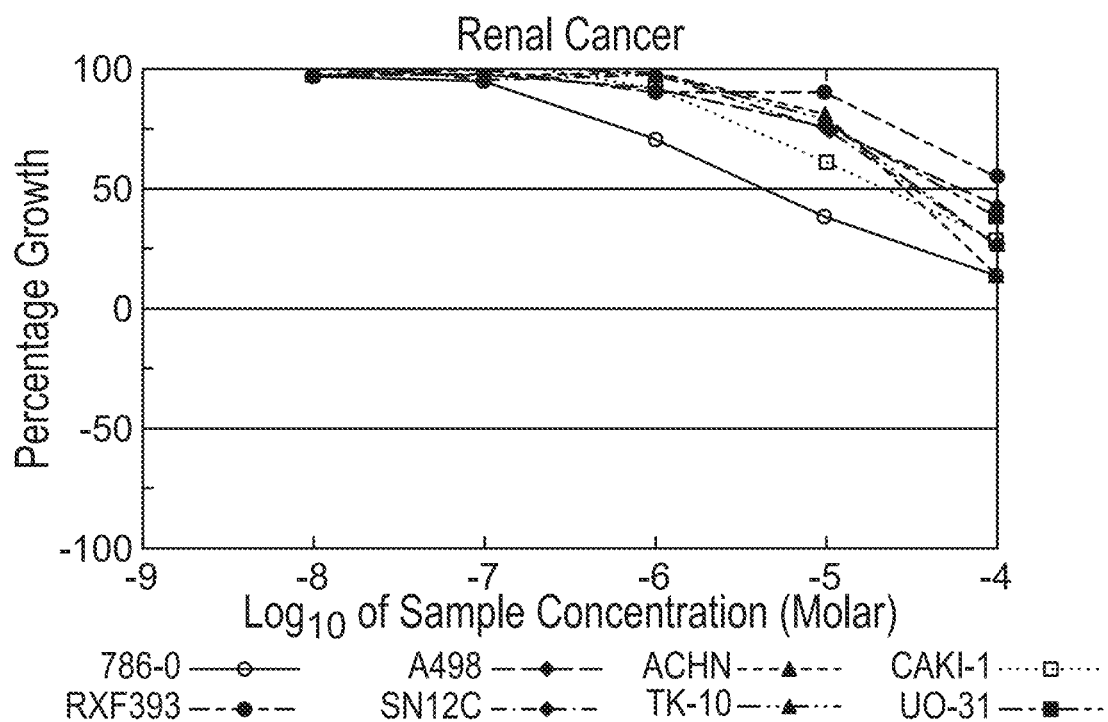
FIG. 18 shows percentage growth of renal cancer cell lines incubated at different concentrations of the pentaaza macrocyclic ring complex M40401 (GC4401), to provide in vitro screening for the anti-proliferative effects of the pentaaza macrocyclic ring complex in the cancerous cell lines.
Figure 19:
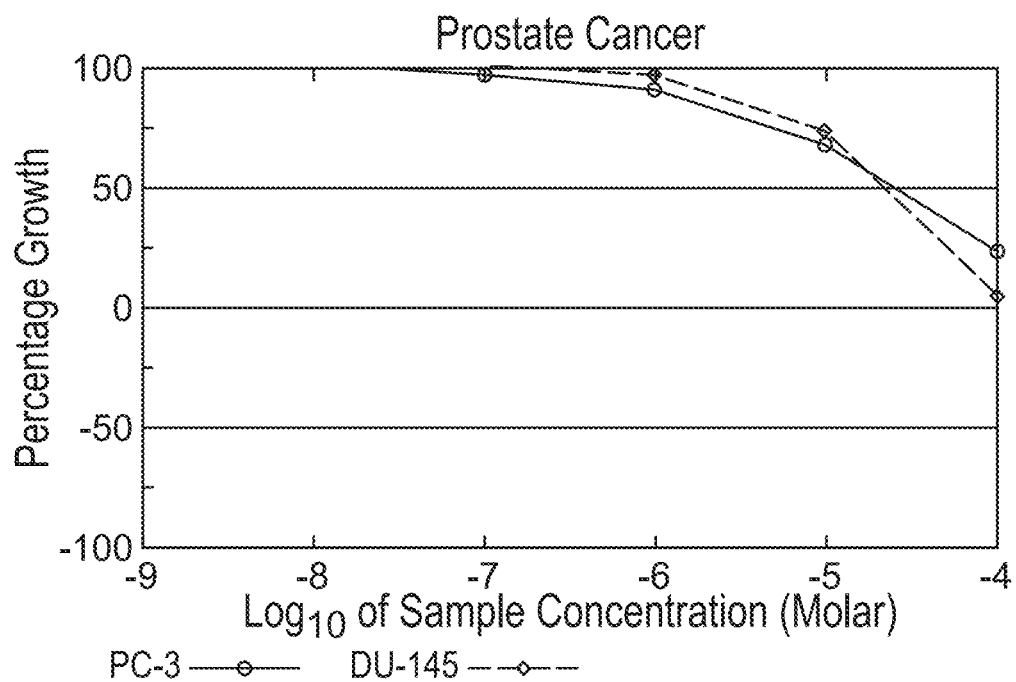
FIG. 19 shows percentage growth of prostate cancer cell lines incubated at different concentrations of the pentaaza macrocyclic ring complex M40401 (GC4401), to provide in vitro screening for the anti-proliferative effects of the pentaaza macrocyclic ring complex in the cancerous cell lines.
Figure 20:
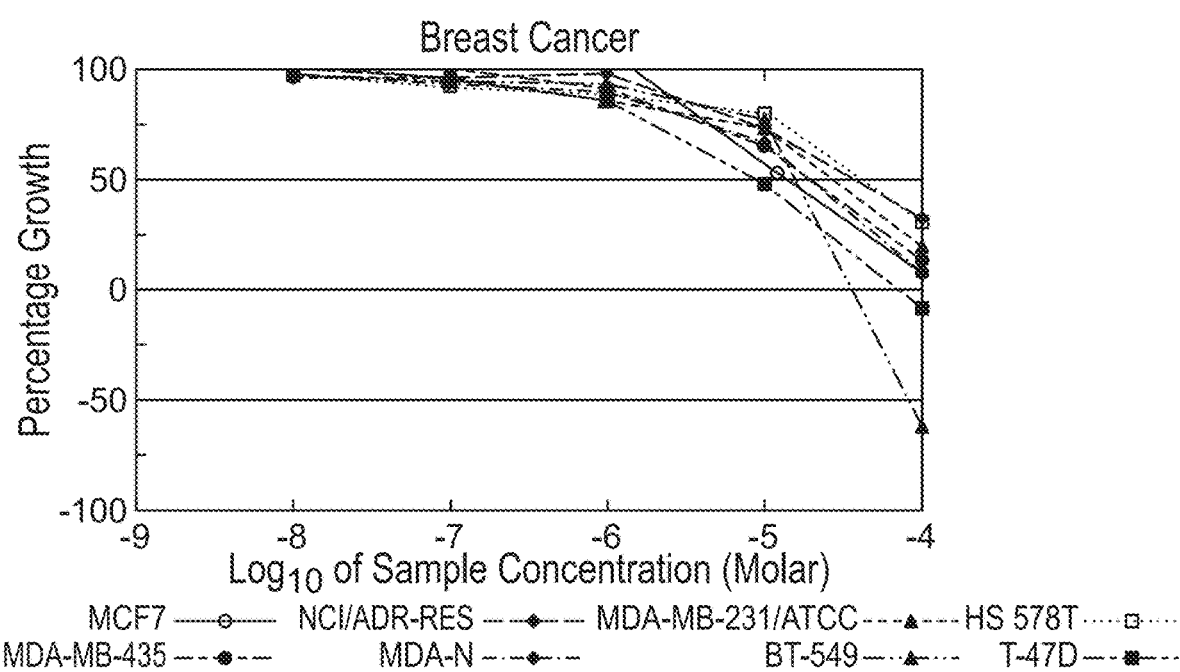
FIG. 20 shows percentage growth of breast cancer cell lines incubated at different concentrations of the pentaaza macrocyclic ring complex M40401 (GC4401), to provide in vitro screening for the anti-proliferative effects of the pentaaza macrocyclic ring complex in the cancerous cell lines.
Figure 21:
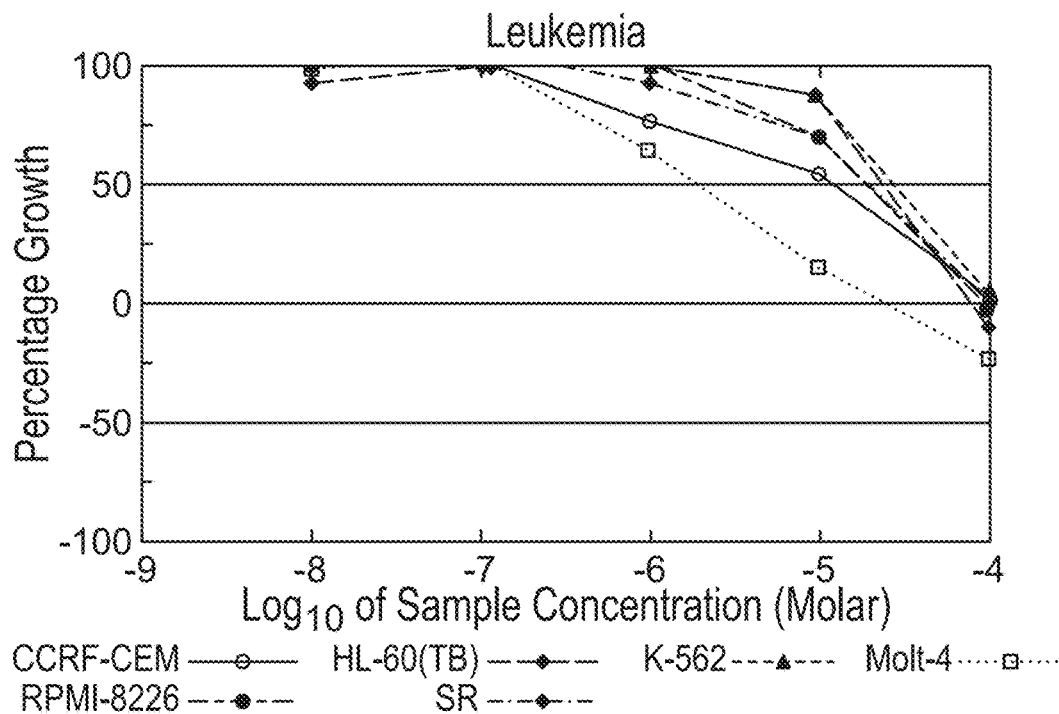
FIG. 21 shows percentage growth of leukemia cancer cell lines incubated at different concentrations of the pentaaza macrocyclic ring complex M40403 (GC4403), to provide in vitro screening for the anti-proliferative effects of the pentaaza macrocyclic ring complex in the cancerous cell lines.
Figure 22:
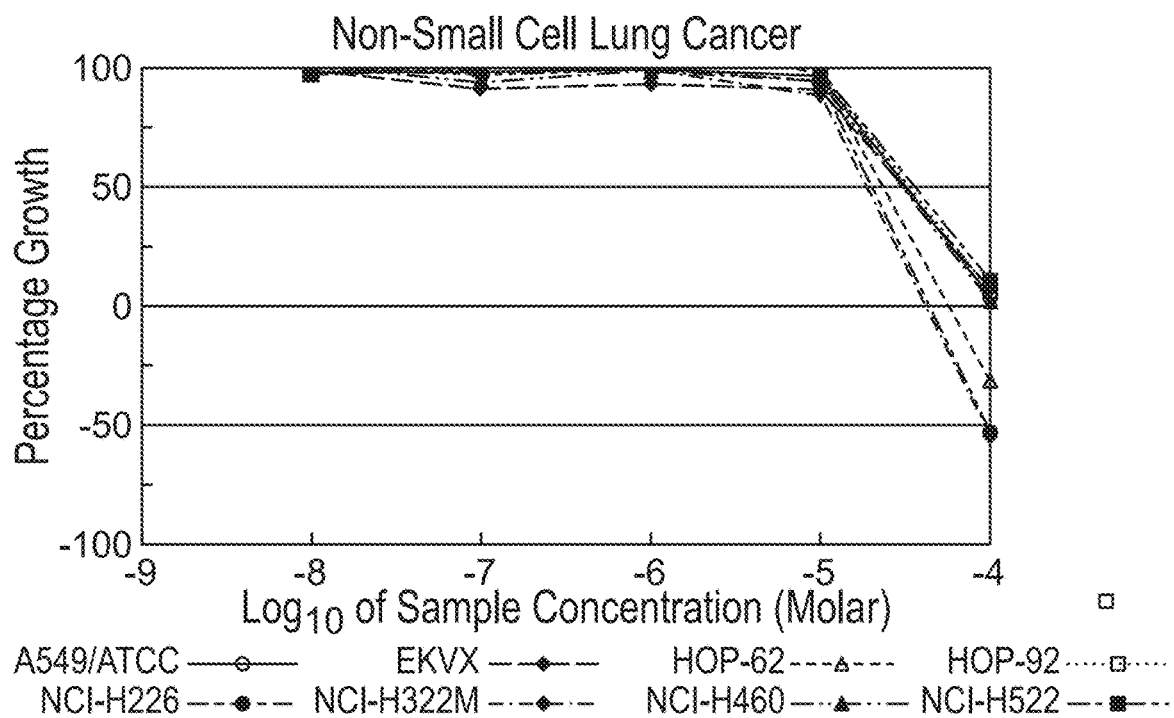
FIG. 22 shows percentage growth of non-small cell lung cancer cell lines incubated at different concentrations of the pentaaza macrocyclic ring complex M40403 (GC4403), to provide in vitro screening for the anti-proliferative effects of the pentaaza macrocyclic ring complex in the cancerous cell lines.
Figure 23:
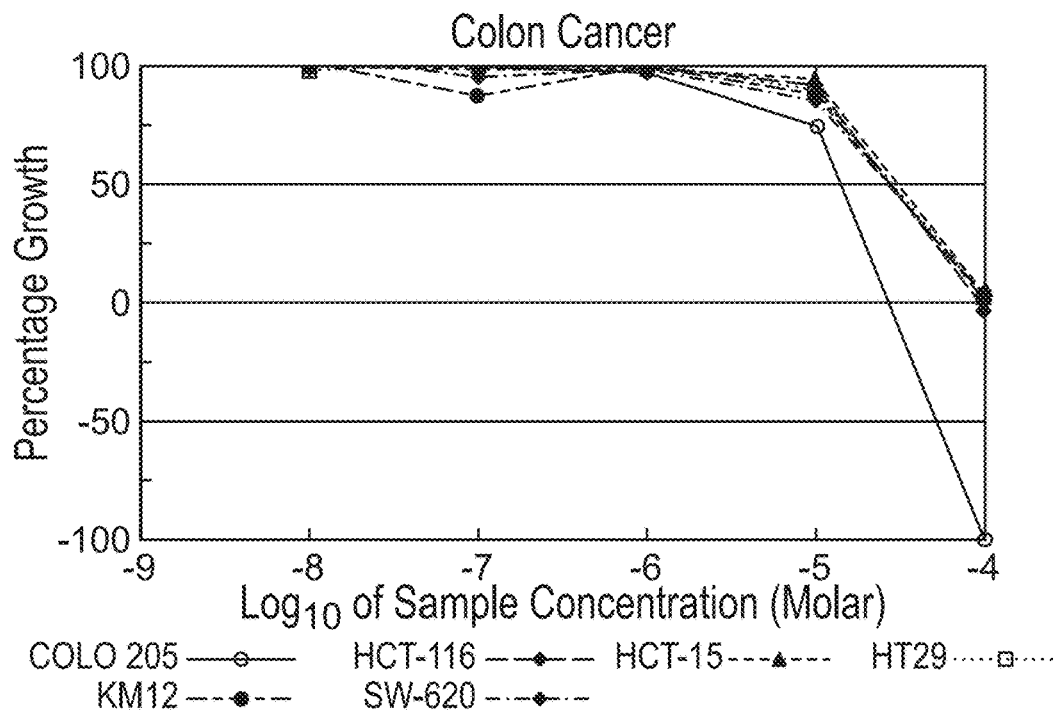
FIG. 23 shows percentage growth of colon cancer cell lines incubated at different concentrations of the pentaaza macrocyclic ring complex M40403 (GC4403), to provide in vitro screening for the anti-proliferative effects of the pentaaza macrocyclic ring complex in the cancerous cell lines.
Figure 24:
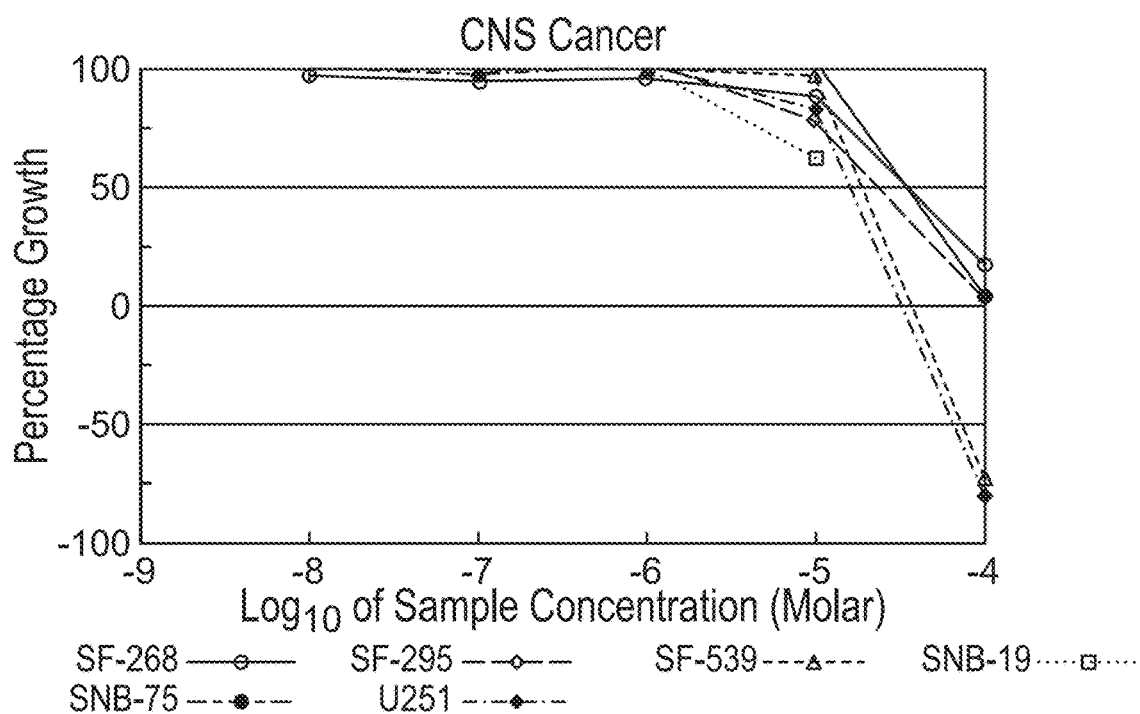
FIG. 24 shows percentage growth of CNS cancer cell lines incubated at different concentrations of the pentaaza macrocyclic ring complex M40403 (GC4403), to provide in vitro screening for the anti-proliferative effects of the pentaaza macrocyclic ring complex in the cancerous cell lines.
Figure 25:
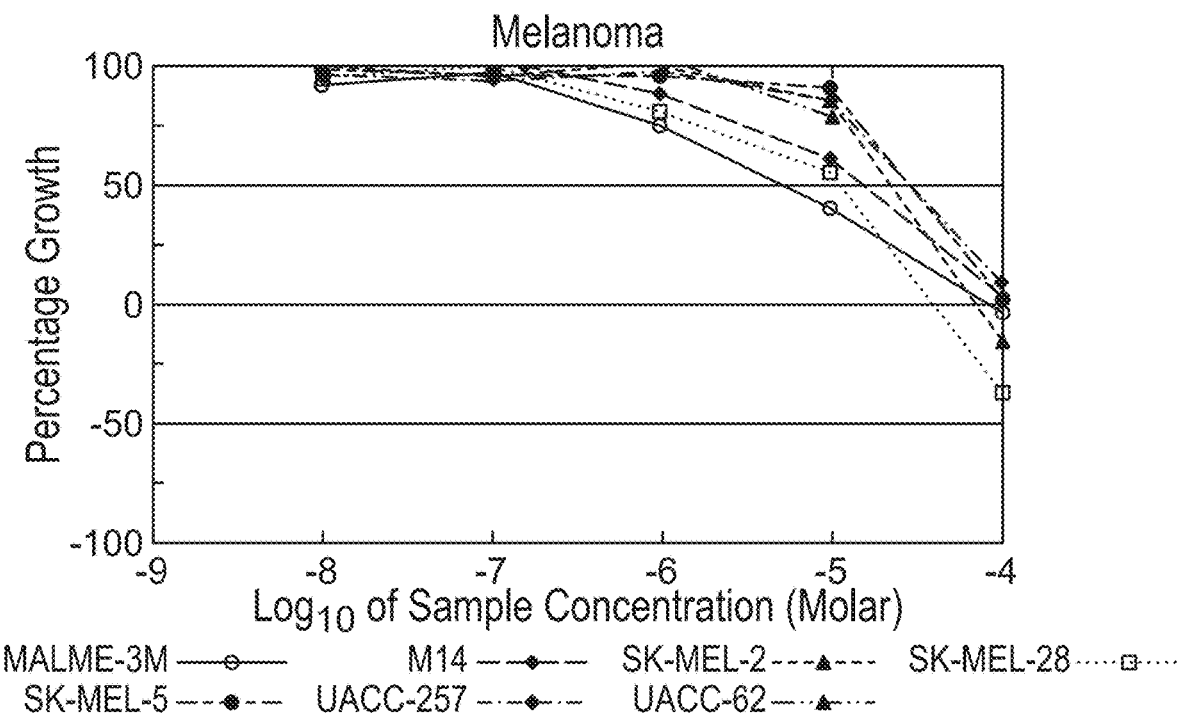
FIG. 25 shows percentage growth of melanoma cancer cell lines incubated at different concentrations of the pentaaza macrocyclic ring complex M40403 (GC4403), to provide in vitro screening for the anti-proliferative effects of the pentaaza macrocyclic ring complex in the cancerous cell lines.
Figure 26:
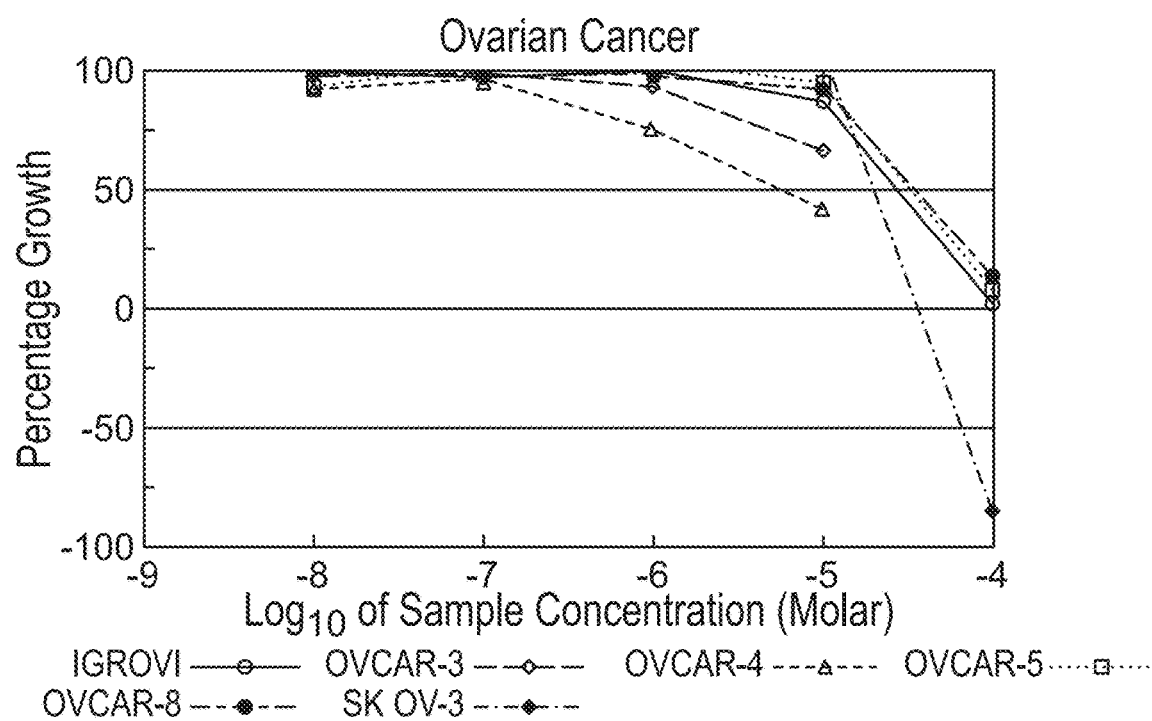
FIG. 26 shows percentage growth of ovarian cancer cell lines incubated at different concentrations of the pentaaza macrocyclic ring complex M40403 (GC4403), to provide in vitro screening for the anti-proliferative effects of the pentaaza macrocyclic ring complex in the cancerous cell lines.
Figure 27:
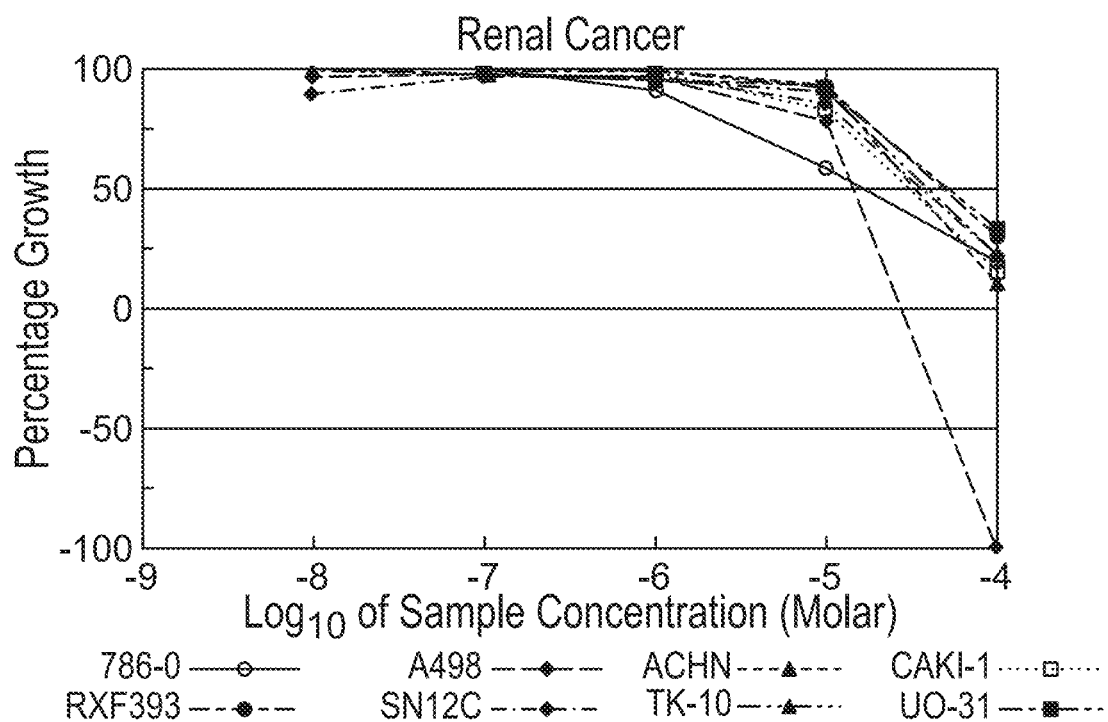
FIG. 27 shows percentage growth of renal cancer cell lines incubated at different concentrations of the pentaaza macrocyclic ring complex M40403 (GC4403), to provide in vitro screening for the anti-proliferative effects of the pentaaza macrocyclic ring complex in the cancerous cell lines.
Figure 28:
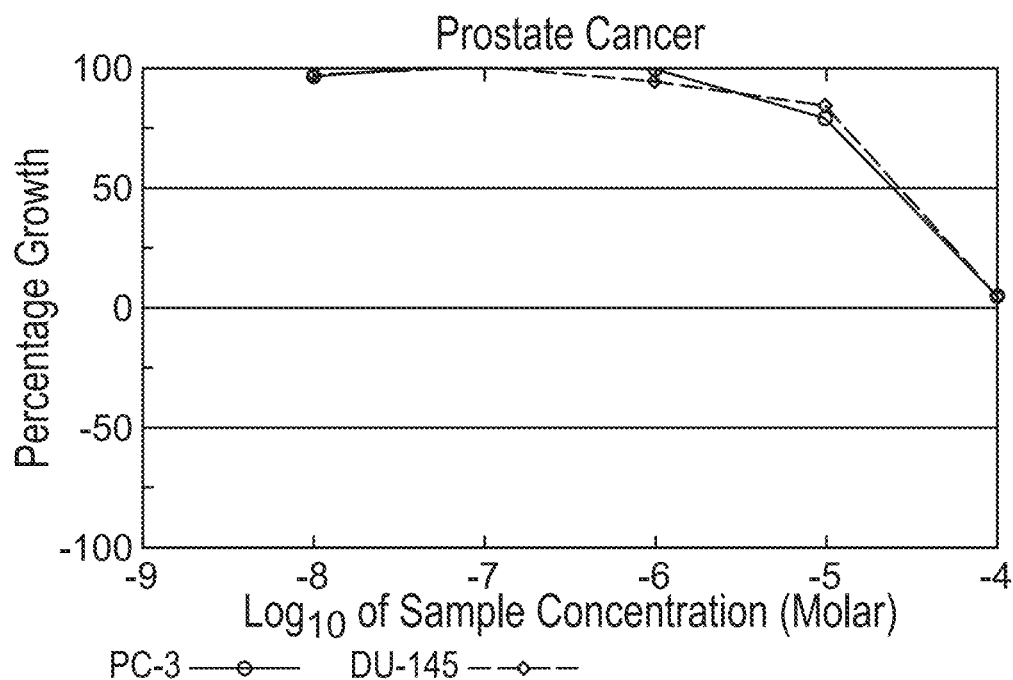
FIG. 28 shows percentage growth of prostate cancer cell lines incubated at different concentrations of the pentaaza macrocyclic ring complex M40403 (GC4403), to provide in vitro screening for the anti-proliferative effects of the pentaaza macrocyclic ring complex in the cancerous cell lines.
Figure 29:
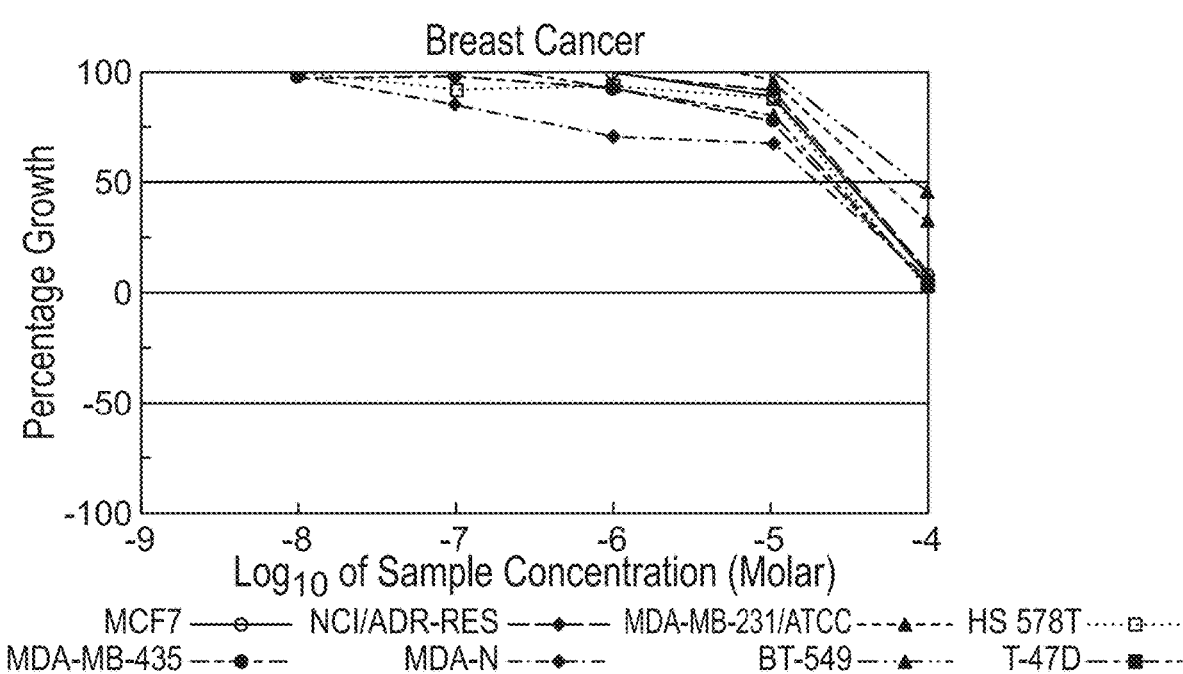
FIG. 29 shows percentage growth of breast cancer cell lines incubated at different concentrations of the pentaaza macrocyclic ring complex M40403 (GC4403), to provide in vitro screening for the anti-proliferative effects of the pentaaza macrocyclic ring complex in the cancerous cell lines.
Figure 30:
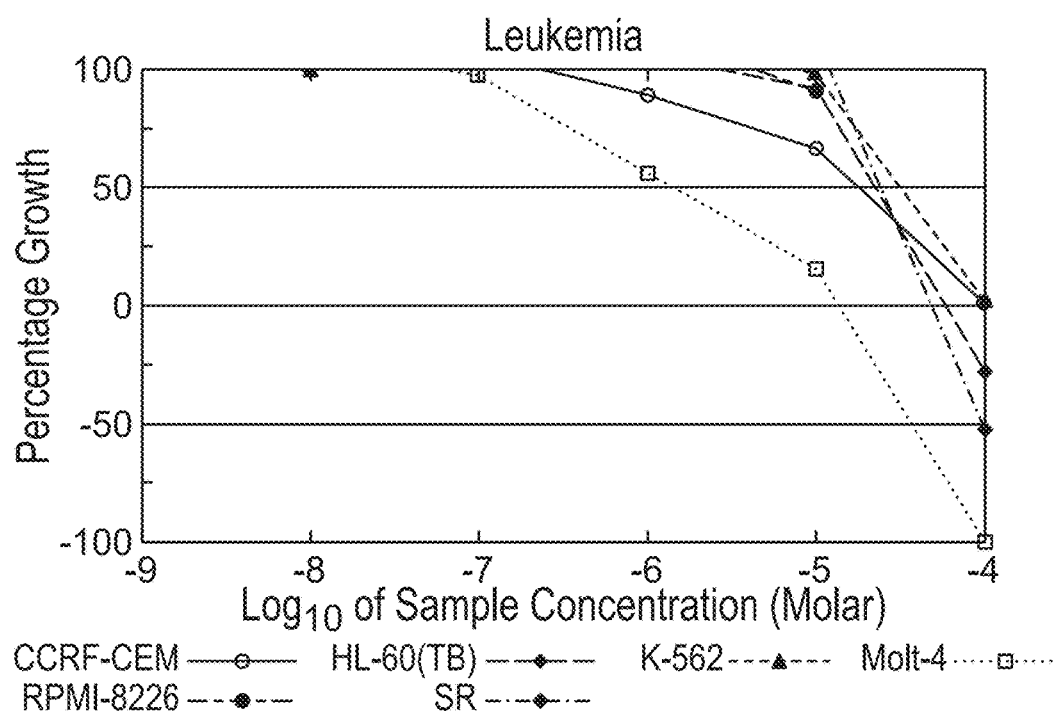
FIG. 30 shows percentage growth of leukemia cancer cell lines incubated at different concentrations of the pentaaza macrocyclic ring complex M40432 (GC4432), to provide in vitro screening for the anti-proliferative effects of the pentaaza macrocyclic ring complex in the cancerous cell lines.
Figure 31:
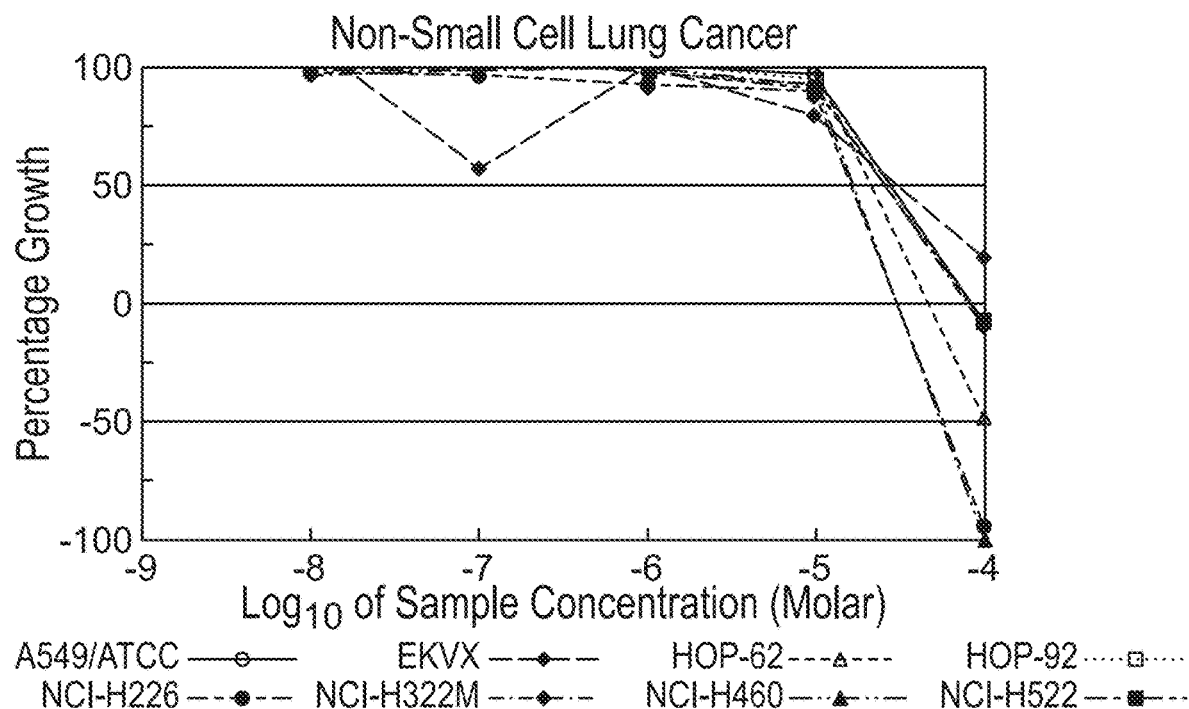
FIG. 31 shows percentage growth of non-small cell lung cancer cell lines incubated at different concentrations of the pentaaza macrocyclic ring complex M40432 (GC4432), to provide in vitro screening for the anti-proliferative effects of the pentaaza macrocyclic ring complex in the cancerous cell lines.
Figure 32:
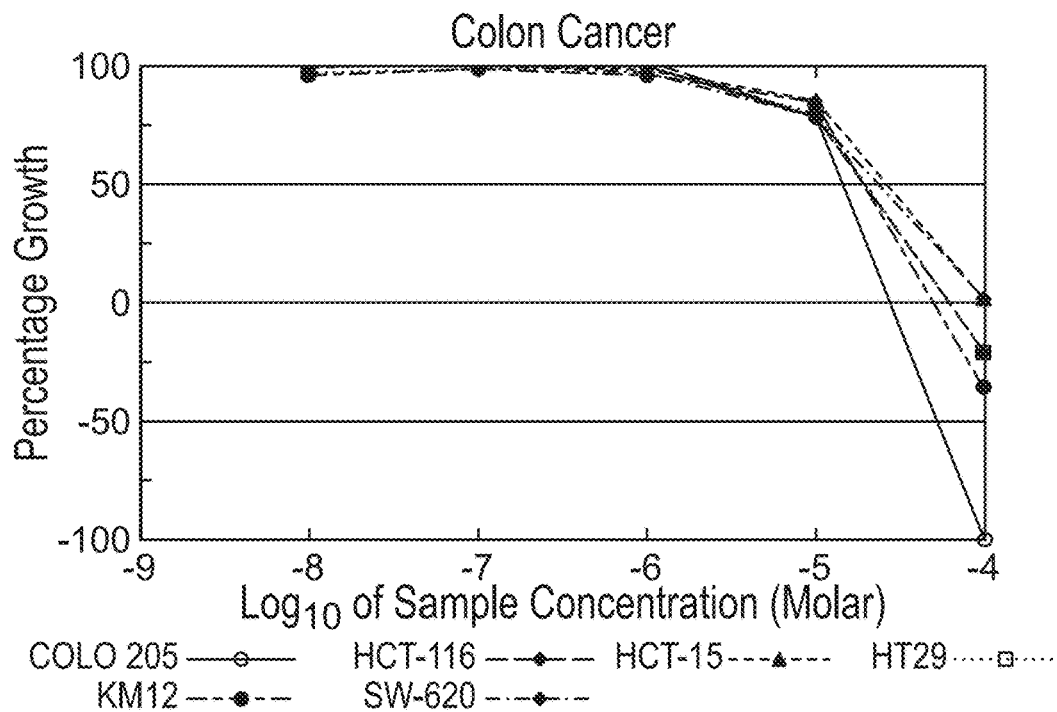
FIG. 32 shows percentage growth of colon cancer cell lines incubated at different concentrations of the pentaaza macrocyclic ring complex M40432 (GC4432), to provide in vitro screening for the anti-proliferative effects of the pentaaza macrocyclic ring complex in the cancerous cell lines.
Figure 33:
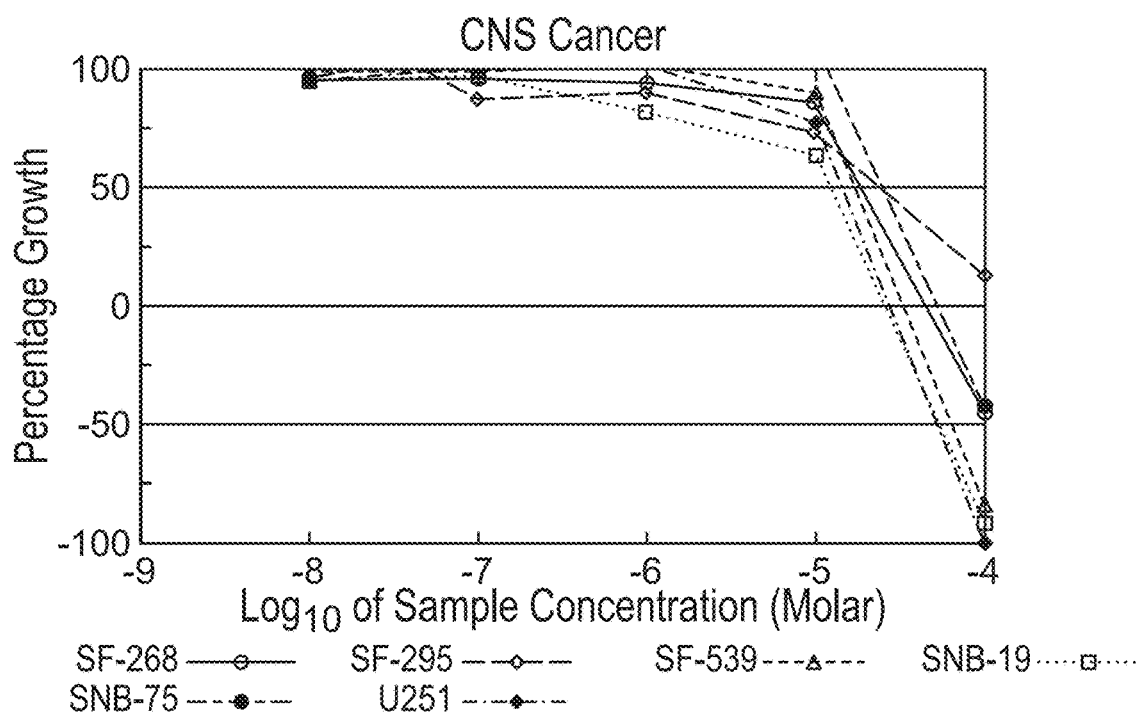
FIG. 33 shows percentage growth of CNS cancer cell lines incubated at different concentrations of the pentaaza macrocyclic ring complex M40432 (GC4432), to provide in vitro screening for the anti-proliferative effects of the pentaaza macrocyclic ring complex in the cancerous cell lines.
Figure 34:
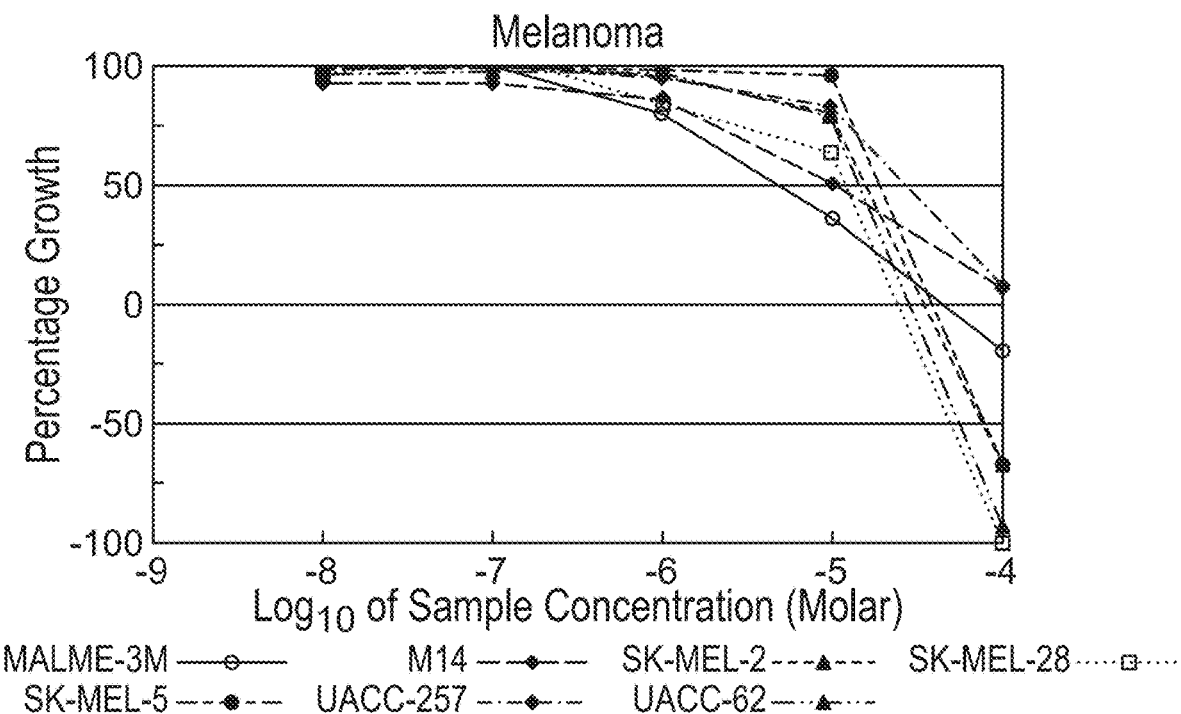
FIG. 34 shows percentage growth of melanoma cancer cell lines incubated at different concentrations of the pentaaza macrocyclic ring complex M40432 (GC4432), to provide in vitro screening for the anti-proliferative effects of the pentaaza macrocyclic ring complex in the cancerous cell lines.
Figure 35:
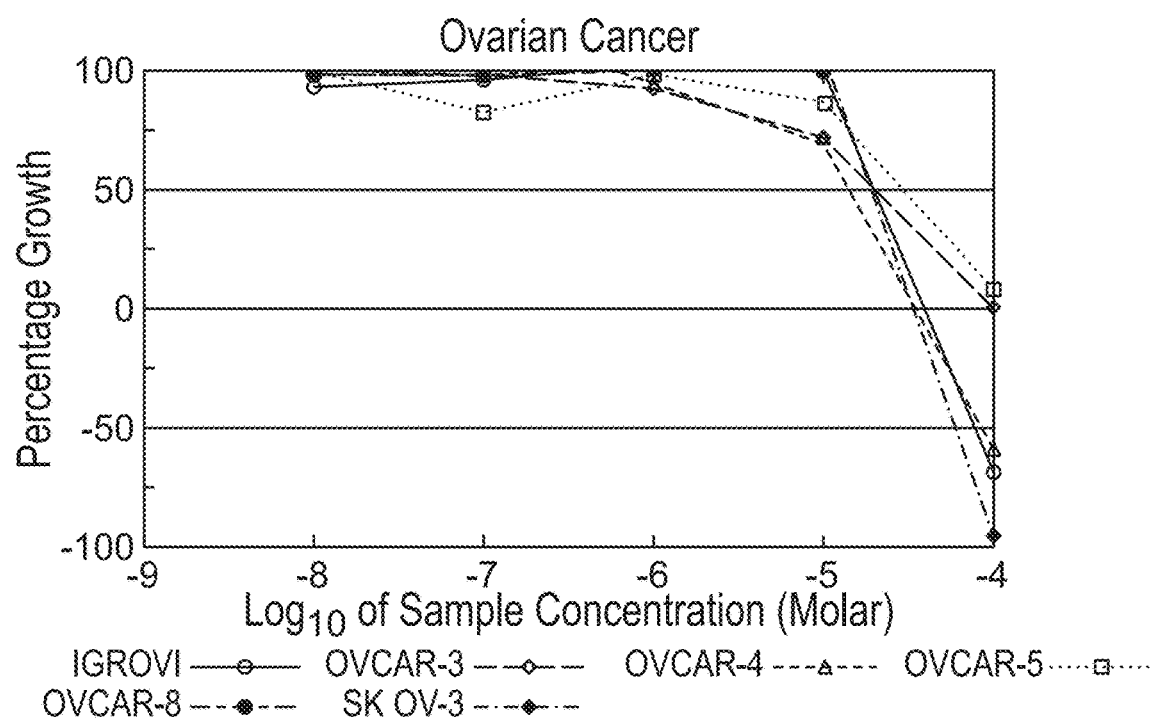
FIG. 35 shows percentage growth of ovarian cancer cell lines incubated at different concentrations of the pentaaza macrocyclic ring complex M40432 (GC4432), to provide in vitro screening for the anti-proliferative effects of the pentaaza macrocyclic ring complex in the cancerous cell lines.
Figure 36:
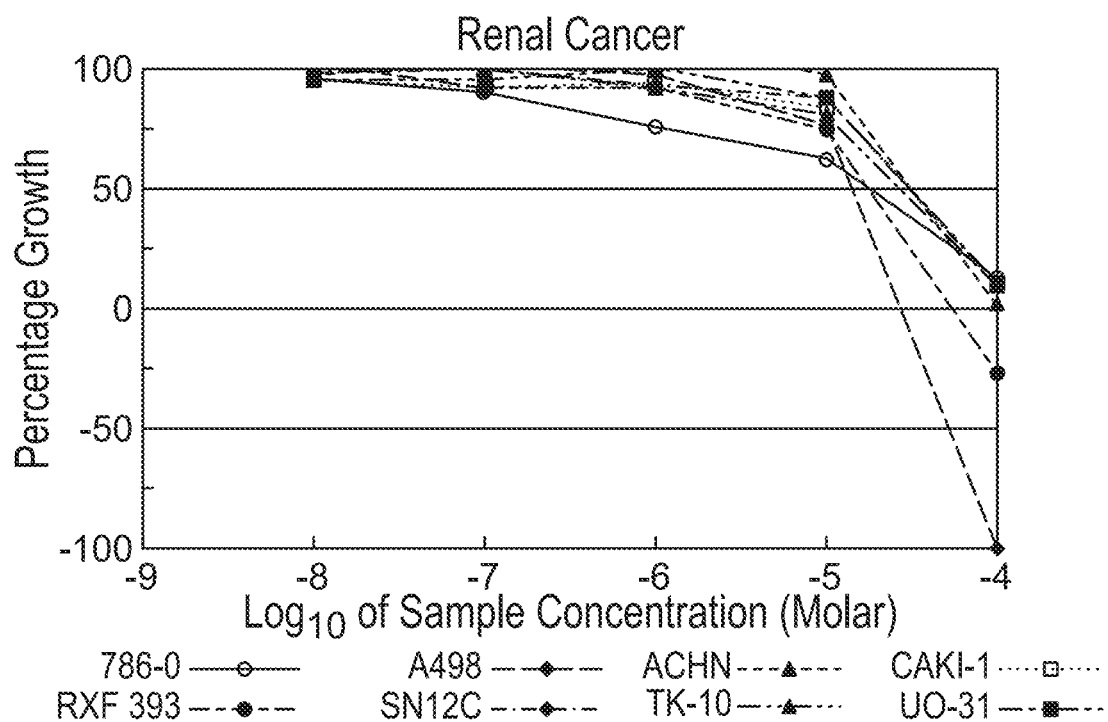
FIG. 36 shows percentage growth of renal cancer cell lines incubated at different concentrations of the pentaaza macrocyclic ring complex M40432 (GC4432), to provide in vitro screening for the anti-proliferative effects of the pentaaza macrocyclic ring complex in the cancerous cell lines.
Figure 37:
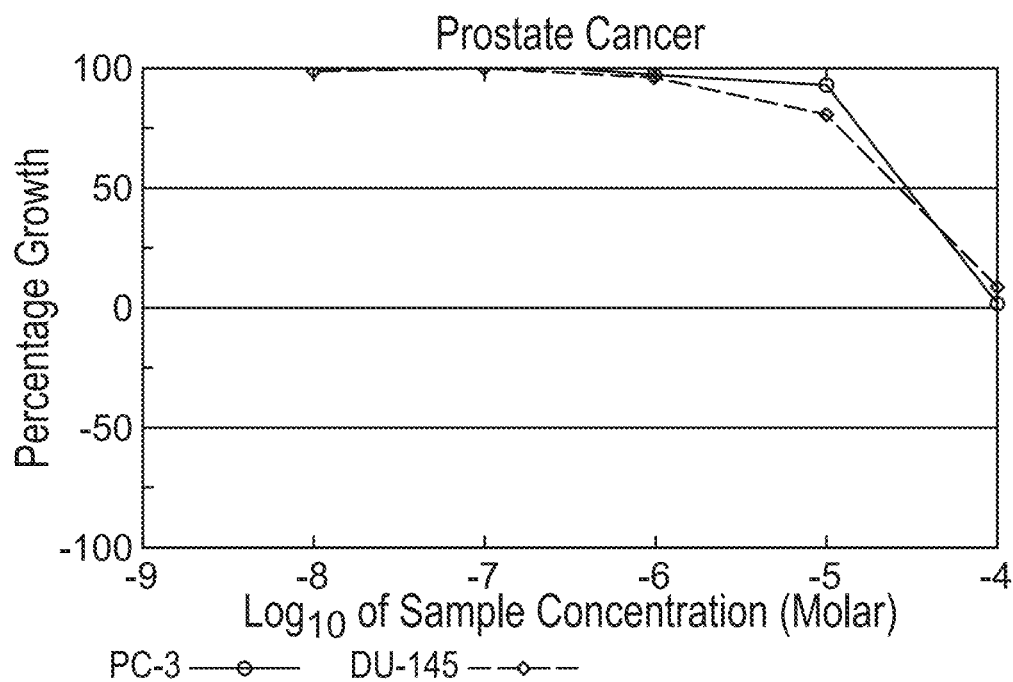
FIG. 37 shows percentage growth of prostate cancer cell lines incubated at different concentrations of the pentaaza macrocyclic ring complex M40432 (GC4432), to provide in vitro screening for the anti-proliferative effects of the pentaaza macrocyclic ring complex in the cancerous cell lines.
Figure 38:
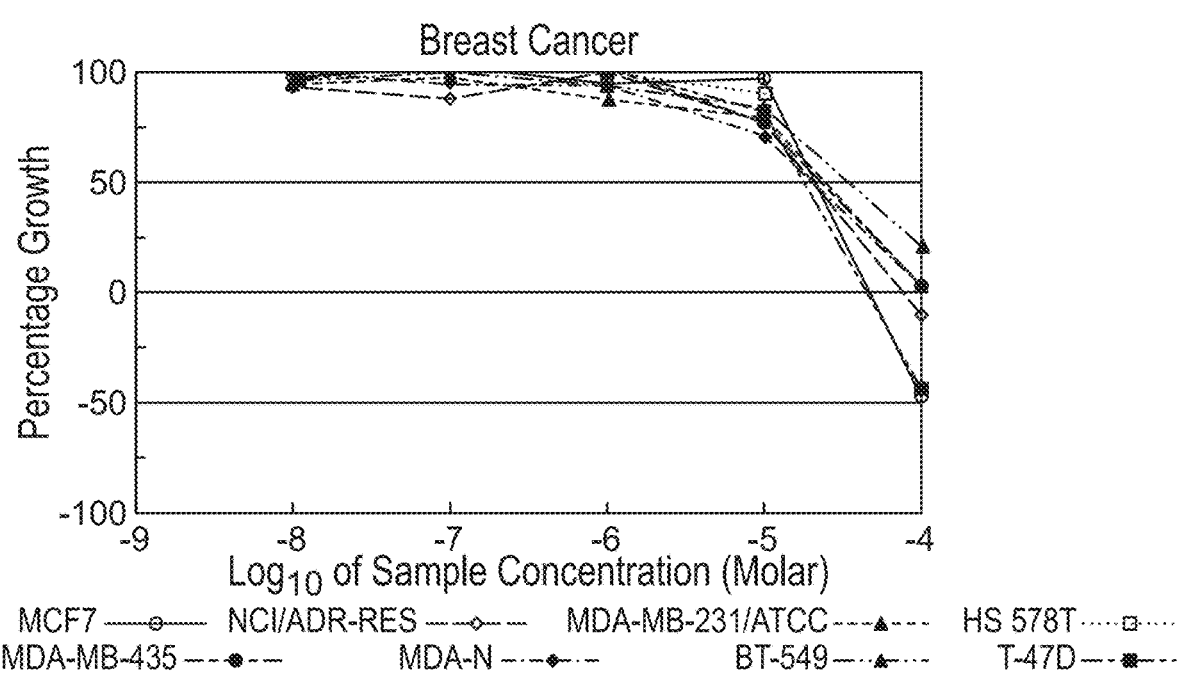
FIG. 38 shows percentage growth of breast cancer cell lines incubated at different concentrations of the pentaaza macrocyclic ring complex M40432 (GC4432), to provide in vitro screening for the anti-proliferative effects of the pentaaza macrocyclic ring complex in the cancerous cell lines.

The effect of GC4419 was tested in vivo on animal models of squamous cell carcinoma of the head and neck (HNSCC). GC4419 was delivered as a 24 mg/kg daily dose delivered as an ip bolus on 5 consecutive days starting 1 hour prior to irradiation. Radiation was delivered as a single dose of 12 Gy using a 10 mm collimated beam aimed at the center of the tumor. The results are shown in FIG. 10. The data shows that GC4419 treatment induces a significant growth delay to HN5 (HNSCC) tumors in vivo. Not only does the administration of GC4419 result in reduced tumor volumes as compared to a control, but the combination of GC4419 with radiation provides even greater growth delays, indicating that the GC4419 increases the response of the cancerous cells to the ionizing radiation.

Example 11

In this example, in vitro screening for the anti-proliferative effects of the pentaaza macrocyclic ring complex M40401 (GC4401) were conducted. Cancerous cell lines were incubated with M40401 (GC4401) for 6 days, at 5 different dosages from $1\times10^{-8}$ to $1\times10^{-4}$ M. Anti-proliferative effects were observed.

The structure of M40401 (GC4401) is below:

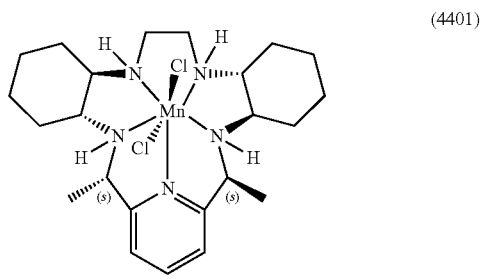

(4401)

The compound was tested in vitro against cancers including leukemia (including lines CCRF-CEM, HB-60(TB), K-562, MOLT-4, RPMI-8226, SR), non-small cell lung cancer (including lines A549/ATCC, EKVX, HOP-62, HOP-92, NCI-H226, NCI-H23, NCI-H322M, NCI-H460, NCI-H522), colon cancer (including lines COLO 205, HCC-2998, HCT-116, HCT-15, HJ29, KM12, SW-620), CNS cancer (including lines SF 268, SF-295, SF-539, SNB-19, SNB-75, U251), melanoma (including lines MALME-3M, M14, SK-MEL-2, SK-MEL-28, SK-MEL-5, UACC-257, ACC-62), ovarian cancer (IGROV1, OVCAR-3, OVCAR-4, OVCAR-5, OVCAR-8, SK-OV-3), renal cancer (including lines 786-0, A498, ACHN, CAKI-J, RXF 393, SN12C, TK 10, UO-31), prostate cancer (including lines PC-3, DU-145) and breast cancer (including lines MCF7, NCVADR-RES, MDA-M8-231/ATCC, HS 578T, MDA-MB-435, MDA-N, BT-549, T-47D). FIGS. 12-20 show the anti-proliferative effects of the compound in the various different cell lines.

Example 12

In this example, in vitro screening for the anti-proliferative effects of the pentaaza macrocyclic ring complex M40403 (G4403) were conducted. Cancerous cell lines were incubated with M40403 (GC4403) for 6 days, at 5 different dosages from $1\times10^{-8}$ to $1\times10^{-4}$ M. Anti-proliferative effects were observed.

The structure of M40403 (GC4403) is below:

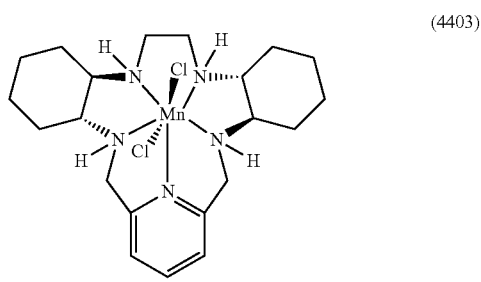

(4403)

The compound was tested in vitro against cancers including leukemia (including lines CCRF-CEM, HB-60(TB), K-562, MOLT-4, RPMI-8226, SR), non-small cell lung cancer (including lines A549/ATCC, EKVX, HOP-62, HOP-92, NCI-H226, NCI-H23, NCI-H322M, NCI-H460, NCI-H522), colon cancer (including lines COLO 205, HCC- 2998, HCT-116, HCT-15, HJ29, KM12, SW-620), CNS cancer (including lines SF 268, SF-295, SF-539, SNB-19, SNB-75, U251), melanoma (including lines MALME-3M, M14, SK-MEL-2, SK-MEL-28, SK-MEL-5, UACC-257, ACC-62), ovarian cancer (IGROV1, OVCAR-3, OVCAR-4, OVCAR-5, OVCAR-8, SK-OV-3), renal cancer (including lines 786-0, A498, ACHN, CAKI-J, RXF 393, SN12C, TK 10, UO-31), prostate cancer (including lines PC-3, DU-145) and breast cancer (including lines MCF7, NCVADR-RES, MDA-M8-231/ATCC, HS 578T, MDA-MB-435, MDA-N, BT-549, T-47D). FIGS. 21-29 show the anti-proliferative effects of the compound in the various different cell lines.

Example 13

In this example, in vitro screening for the anti-proliferative effects of the pentaaza macrocyclic ring complex M40432 (GC4432) were conducted. Cancerous cell lines were incubated with M40432 (G4432) for 6 days, at 5 different dosages from $1\times10^{-8}$ to $1\times10^{-4}$ M. Anti-proliferative effects were observed.

The structure of M40432 (GC4432) is below:

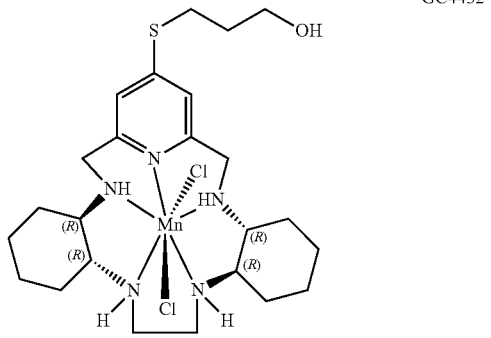

GC4432

The compound was tested in vitro against cancers including leukemia (including lines CCRF-CEM, HB-60(TB), K-562, MOLT-4, RPMI-8226, SR), non-small cell lung cancer (including lines A549/ATCC, EKVX, HOP-62, HOP-92, NCI-H226, NCI-H23, NCI-H322M, NCI-H460, NCI-H522), colon cancer (including lines COLO 205, HCC-2998, HCT-116, HCT-15, HJ29, KM12, SW-620), CNS cancer (including lines SF 268, SF-295, SF-539, SNB-19, SNB-75, U251), melanoma (including lines MALME-3M, M14, SK-MEL-2, SK-MEL-28, SK-MEL-5, UACC-257, ACC-62), ovarian cancer (IGROV1, OVCAR-3, OVCAR-4, OVCAR-5, OVCAR-8, SK-OV-3), renal cancer (including lines 786-0, A498, ACHN, CAKI-J, RXF 393, SN12C, TK 10, UO-31), prostate cancer (including lines PC-3, DU-145) and breast cancer (including lines MCF7, NCVADR-RES, MDA-M8-231/ATCC, HS 578T, MDA-MB-435, MDA-N, BT-549, T-47D). FIGS. 30-38 show the anti-proliferative effects of the compound in the various different cell lines.

Embodiments according to aspects of the disclosure are provided below, although the disclosure is not limited thereto.

Embodiment 1. A method of treating a cancer in a mammalian subject afflicted with the cancer, the method comprising:

administering to the subject at least one active agent comprising one or more of a thioredoxin reductase inhibitor and a glutathione depleting agent; and administering to the subject a pentaaza macrocyclic ring complex corresponding to formula (I) below:

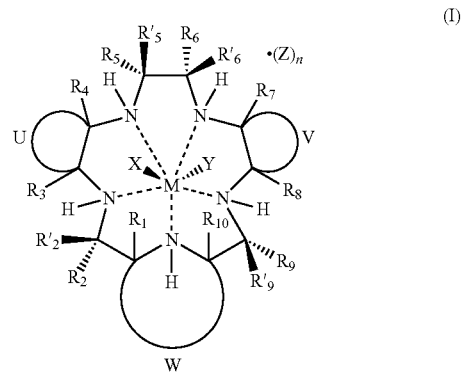

(I)

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Embodiment 2. A method in accordance with Embodiment 1, wherein $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are each hydrogen.

Embodiment 3. A method in accordance with any preceding Embodiment, wherein W is an unsubstituted pyridine moiety.

Embodiment 4. A method in accordance with any preceding Embodiment, wherein U and V are trans-cyclohexanyl fused rings.

Embodiment 5. A method in accordance with any preceding Embodiment, wherein the pentaaza macrocyclic ring complex is a complex selected from the group consisting of the complexes of formula (2)-(7) below:

2

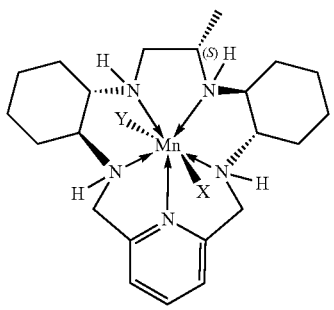

3

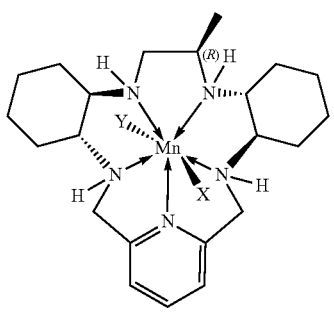

4

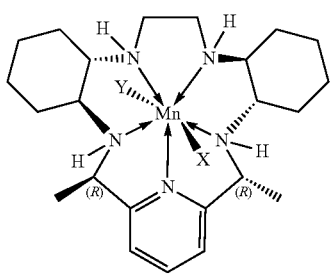

5

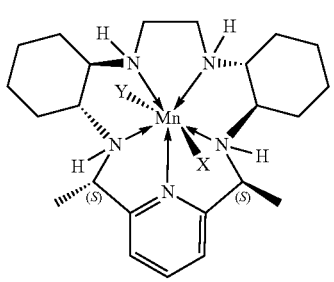

6

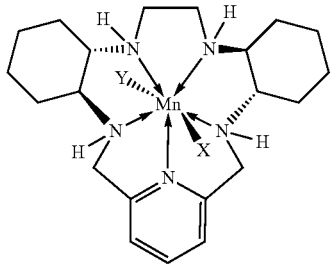

7

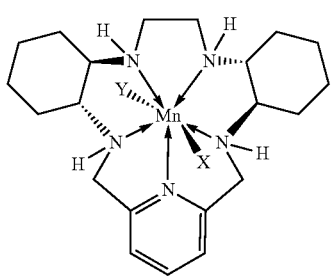

Embodiment 6. A method in accordance with any preceding Embodiment, wherein X and Y, are independently selected from the group consisting of fluoro, chloro, bromo and iodo anions.

Embodiment 7. A method in accordance with any preceding Embodiment, wherein X and Y correspond to —O—C(O)—$X_1$, where each $X_1$ is —C($X_2$)($X_3$)($X_4$), and each —C($X_2$)($X_3$)($X_4$) corresponds to any of combinations 1 to 7 appearing in the following table:

| Combination | $X_2$ | $X_3$ | $X_4$ |
|---|---|---|---|
| 1 | Ph | H | H |
| 2 | Ph | OH | H |
| 3 | Ph | $NH_2$ | H |
| 4 | Ph | =O ($X_3$ and $X_4$ in combination) | |
| 5 | Ph | $CH_3$ | H |
| 6 | $CH_3$ | H | H |
| 7 | $CH_3$ | OH | H |

Embodiment 8. A method in accordance with any preceding Embodiment, wherein the pentaaza macrocyclic ring complex is at least one of the following:

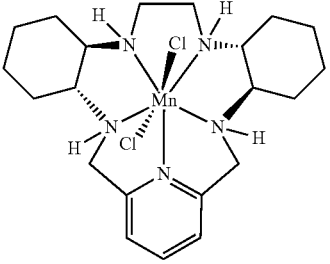

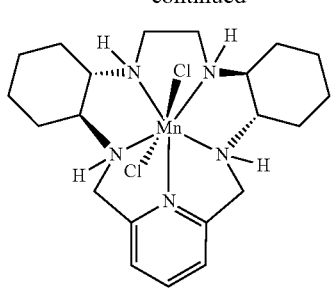
(4419)

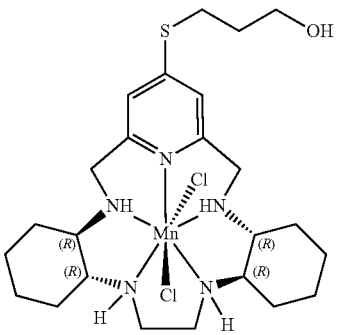
(4432)

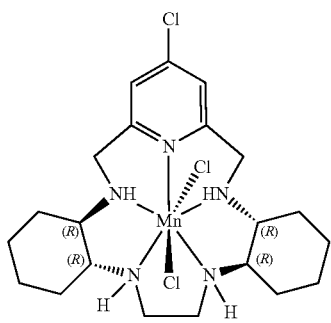
(4409)

Embodiment 9. A method in accordance with any preceding Embodiment, wherein the at least one active agent is one that increases intracellular $H_2O_2$ levels in cancerous cells, when provided to such cancerous cells in vitro in combination with the pentaaza macrocyclic ring complex.

Embodiment 10. A method in accordance with any preceding Embodiment, wherein the combination of the at least one active agent and pentaaza macrocyclic ring complex selectively kills cancer cells over normal cells when administered for the cancer treatment.

Embodiment 11. A method in accordance with any preceding Embodiment, wherein the thioredoxin reductase inhibitor is at least one of auranofin, auro-thio-glucose, chloro(triethylphosphine)gold(I), aurothiomalate, gold sodium thiomalate, sodium aurothiosulfate, gold acetate, 1,2,5-selenadiazole and derivatives thereof, metal complexes with 2-acetylpyridine-N(4)-orthochlorophenylthiosemicarbazone and/or a pharmaceutically acceptable salt thereof.

Embodiment 12. A method in accordance with Embodiment 10, wherein the thioredoxin reductase inhibitor is auranofin.

Embodiment 13. A method in accordance with any preceding Embodiment, wherein the glutathione depleting agent is at least one of a glutathione synthesis inhibitor, an inhibitor of $x_c^-$ cysteine/glutamate antiporter, and a glutathione reductase inhibitor, Embodiment 14. A method in accordance with Embodiment 13, wherein the glutathione-depleting agent is at least one of buthionine sulfoximine (BSO), sulfasalazine, piperlongumine, N-ethylmaleimide, N-pyrenylmaleimide, 2-AAPA, erastin, sorafenib, 1S,3R-RSL3, DPI19, DPI18, DPI17, DPI13, DPI12, DPI10 (ML210), DPI7(ML162), and altretamine, and/or pharmaceutically acceptable salts thereof Embodiment 15. A method in accordance with Embodiment 14, wherein the glutathione-depleting agent is at least one of buthionine sulfoximine and sulfasalazine.

Embodiment 16. A method in accordance with any preceding Embodiment, comprising administering both a thioredoxin reductase inhibitor and a glutathione depleting agent in combination with the pentaaza macrocyclic ring complex.

Embodiment 17. A method in accordance with any preceding Embodiment, wherein the mammal is a human patient.

Embodiment 18. A method in accordance with any preceding Embodiment, wherein the cancer is selected from the group consisting of cancer of the breast, heart, lung, small intestine, colon, spleen, kidney, bladder, head and neck, ovary, prostate, brain, pancreas, skin, bone, bone marrow, blood, thymus, uterus, testicles, cervix, and liver.

Embodiment 19. A method in accordance with Embodiment 18, wherein the subject is afflicted with cancer selected from the group consisting of breast cancer, lung cancer, renal cell carcinoma, spindle cell carcinoma, colorectal cancer, and head and neck cancer.

Embodiment 20. A method in accordance with Embodiment 19, wherein the subject is afflicted with cancer selected from the group consisting of breast cancer and lung cancer.

Embodiment 21. A method in accordance with any preceding Embodiment, wherein the active agent is administered substantially simultaneously with the pentaaza macrocyclic ring complex.

Embodiment 22. A method in accordance with any preceding Embodiment, wherein the active agent is administered before the pentaaza macrocyclic ring complex.

Embodiment 23. A method in accordance with any preceding Embodiment, wherein the active agent is administered after the pentaaza macrocyclic ring complex.

Embodiment 24. A method in accordance with any preceding Embodiment, wherein the active agent and pentaaza macrocyclic ring complex are administered within 24 hours of each other.

Embodiment 25. A method in accordance with any preceding Embodiment, wherein the active agent and pentaaza macrocyclic ring complex are administered within 1 hour of each other.

Embodiment 26. A method in accordance with any preceding Embodiment, wherein the active agent and pentaaza macrocyclic ring complex are administered by an administration route selected from the group consisting of oral, parenteral, intravenous, intraarterial, subcutaneous, rectal, subcutaneous, intramuscular, intraorbital, intracapsular, intraspinal, intraperitoneal, intrasternal, topical, nasal, transdermal, intraocular, intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Embodiment 27. A method in accordance with any preceding Embodiment, wherein the method further comprises administering a cancer therapy comprising at least one of a radiation therapy and a chemotherapeutic therapy to the subject.

Embodiment 28. A method in accordance with Embodiment 27, wherein the active agent and pentaaza macrocyclic ring complex are administered prior to the cancer therapy.

Embodiment 29. A method in accordance with any of Embodiments 27-28, wherein the active agent and pentaaza macrocyclic ring complex are administered within 24 hours of the cancer therapy.

Embodiment 30. A method in accordance with any of Embodiments 27-29, wherein the active agent and pentaaza macrocyclic ring complex are administered within 1 hour of the cancer therapy.

Embodiment 31. A method in accordance with Embodiment 27, wherein at least one of the active agent and pentaaza macrocyclic ring complex are administered after the cancer therapy.

Embodiment 32. A method in accordance with any of Embodiments 27-30, wherein the cancer therapy comprises the administration of a series of multiple doses of radiation, and wherein the active agent and pentaaza macrocyclic ring complex are administered before one or more radiation dose in the series.

Embodiment 33. A method in accordance with any of Embodiments 27-30, wherein the chemotherapy dose comprises administration of a chemotherapeutic agent selected from the group consisting of all-trans retinoic acid, azacitidine, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tiguanine, valrubicin, vinblastine, vincristine, vindesine, and vinorelbine.

Embodiment 34. A method of treating a cancer in a mammalian subject afflicted with the cancer, the method comprising:
administering to the subject at least one active agent comprising at least one of a thioredoxin reductase inhibitor and a glutathione-depleting agent;
administering to the subject a pentaaza macrocyclic ring complex; and
administering to the subject a cancer therapy comprising at least one of radiation therapy and chemotherapy;
wherein the pentaaza macrocyclic ring complex corresponds to the formula (I) below:

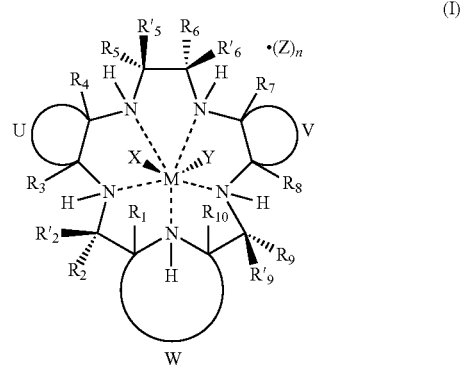

(I)

wherein
M is $Mn^{2+}$ or $Mn^{3+}$;
$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

What is claimed is:

1. A method of treating a cancer in a mammalian subject afflicted therewith, the cancer being selected from the group consisting of breast cancer, and lung cancer, the method comprising:
administering to the subject at least one active agent comprising a thioredoxin reductase inhibitor;
wherein the thioredoxin reductase inhibitor is auranofin; and
administering to the subject a pentaaza macrocyclic ring complex corresponding to formulae (II), (III) or (IV) below:

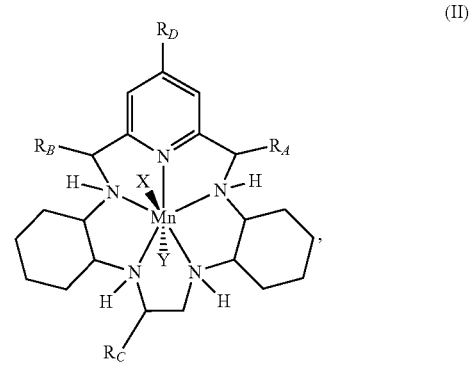

(II)

-continued (III)

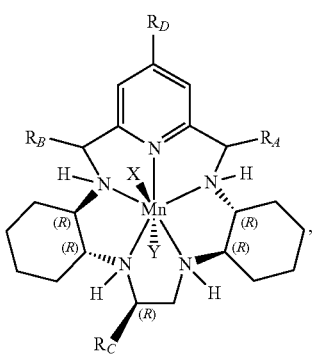

(IV)

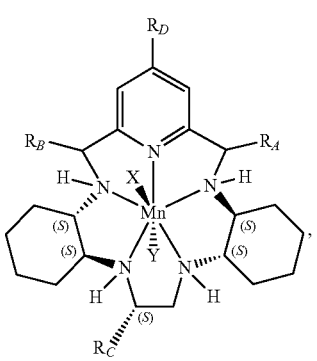

wherein
X and Y are independently selected from any one or more of: (i) the group consisting of fluoro, chloro, bromo, and iodo anions; (ii) the group consisting of alkyl carboxylates, aryl carboxylates and arylalkyl carboxylates; and (iii) amino acids; and
$R_A$, $R_B$, $R_C$, and $R_D$ are independently hydrogen or hydrocarbyl.

2. The method according to claim 1, wherein the pentaaza macrocyclic ring complex is a compound represented by a formula selected from the group consisting of the complexes of formulae (V)-(XVI) below:

(V)

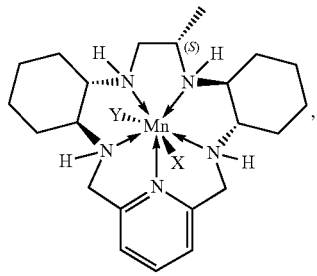

(VI)

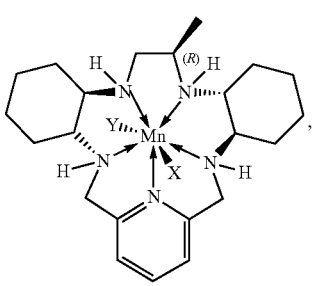

-continued (VII)

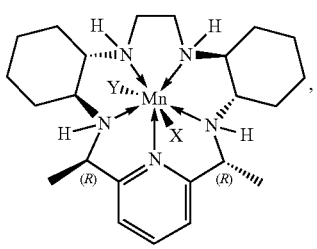

(VIII)

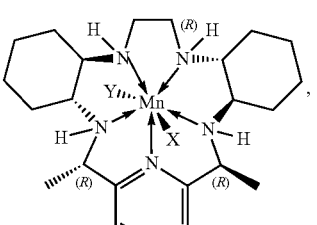

(IX)

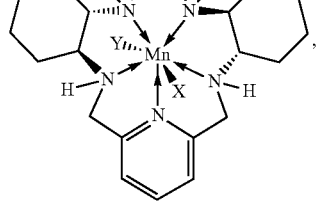

(X)

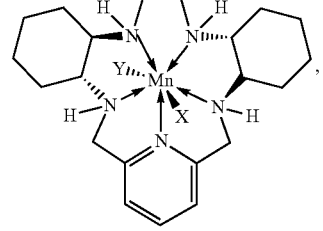

(XV)

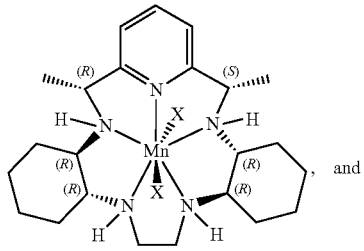
, and (XVI)

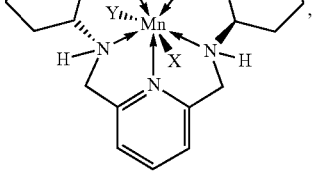

3. The method according to claim 1, wherein X and Y are chloro anions.

4. The method according to claim 1, wherein X and Y are independently selected from the group consisting of alkyl carboxylates, aryl carboxylates and arylalkyl carboxylates.

5. The method according to claim 1, wherein X and Y are independently amino acids.

6. The method according to claim 1, wherein the pentaaza macrocyclic ring complex is a compound represented by the formula:

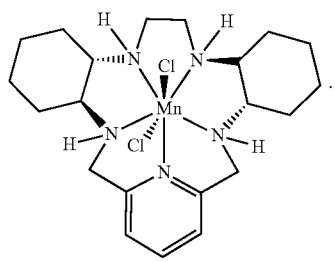
(4419)

7. The method according to claim 1, wherein the pentaaza macrocyclic ring complex is a compound represented by the formula:

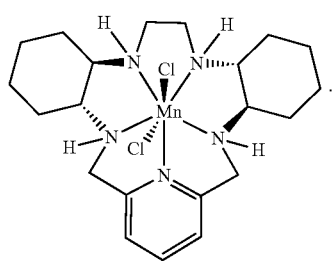
(4403)

8. The method according to claim 1, wherein the pentaaza macrocyclic ring complex is a compound represented by the formula:

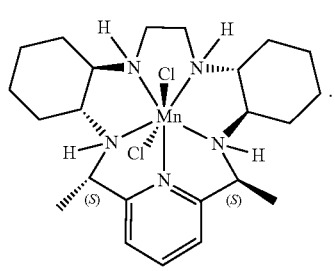
(4401)

9. The method according to claim 1, wherein the pentaaza macrocyclic ring complex is represented by the formula:

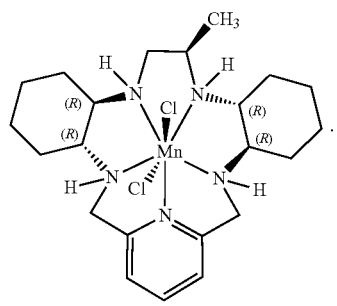
(4444)

10. The method according to claim 1, wherein the pentaaza macrocyclic ring complex is represented by the formula:

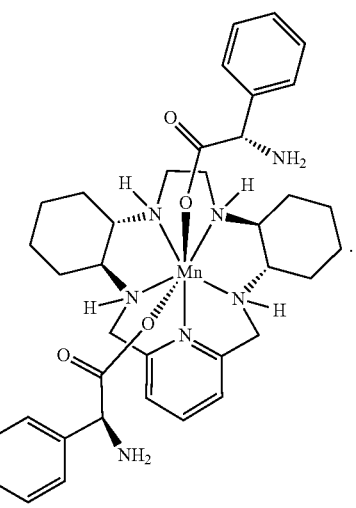
(4702)

11. The method according to claim 1, wherein the pentaaza macrocyclic ring complex is represented by the formula:

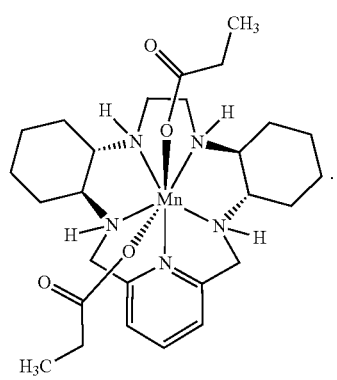
(4711)

12. The method according to claim 1, wherein the thioredoxin reductase inhibitor increases intracellular $H_2O_2$ levels in cancerous cells, when provided to such cancerous cells in vitro in combination with the pentaaza macrocyclic ring complex.

13. The method according to claim 1, wherein the combination of the at least one active agent and pentaaza macrocyclic ring complex selectively kills cancer cells over normal cells when administered for the cancer treatment.

14. The method according to claim 1, further comprising administering to the subject a glutathione depleting agent in combination with the thioredoxin reductase inhibitor and the pentaaza macrocyclic ring complex.

15. The method according to claim 1, wherein the mammal is a human patient.

16. The method according to claim 1, wherein the method further comprises administering a cancer therapy comprising at least one of a radiation therapy and a chemotherapeutic therapy to the subject.

17. The method according to claim 16, wherein the cancer therapy comprises the administration of a series of multiple doses of radiation, and wherein the active agent and pentaaza macrocyclic ring complex are administered before one or more radiation dose in the series.

18. The method according to claim 16, wherein the chemotherapy dose comprises administration of a chemotherapeutic agent selected from the group consisting of all-trans retinoic acid, azacitidine, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tiguanine, valrubicin, vinblastine, vincristine, vindesine, and vinorelbine.

19. The method according to claim 14, wherein the glutathione-depleting agent is at least one of a glutathione synthesis inhibitor, an inhibitor of $x_c^-$ cysteine/glutamate antiporter, and a glutathione reductase inhibitor.

20. The method according to claim 19, wherein the glutathione-depleting agent is at least one of buthionine sulfoximine (BSO), sulfasalazine, piperlongumine, N-ethylmaleimide, N-pyrenylmaleimide, 2-AAPA, erastin, sorafenib, 1S,3R-RSL3, DPI19, DPI18, DPI17, DPI13, DPI12, DPI10 (ML210), DPI7 (ML162), and altretamine, and/or pharmaceutically acceptable salts thereof.

21. The method according to claim 20, wherein the glutathione-depleting agent is at least one of buthionine sulfoximine and sulfasalazine.

* * * * *